(12) United States Patent
Van Alstyne et al.

(10) Patent No.: US 8,071,102 B1
(45) Date of Patent: Dec. 6, 2011

(54) METHODS TO CLEAR MENINGITIS CAUSING AGENTS USING ANTIBODIES TO PEPTIDES REPRESENTING EPITOPIC SITES FOR BACTERIAL AND VIRAL MENINGITIS CAUSING AGENTS

(76) Inventors: Diane Van Alstyne, Vancouver (CA); Lawrence R. Sharma, Spring, TX (US)

( * ) Notice: Subject to any disclaimer, the term of this patent is extended or adjusted under 35 U.S.C. 154(b) by 0 days.

(21) Appl. No.: 09/489,850

(22) Filed: Jan. 24, 2000

Related U.S. Application Data

(63) Continuation of application No. 08/988,444, filed on Dec. 11, 1997, now abandoned, which is a continuation of application No. 08/486,050, filed on Jun. 7, 1995, now abandoned, which is a continuation-in-part of application No. 08/127,499, filed on Sep. 28, 1993, now Pat. No. 5,510,264.

(51) Int. Cl.
*A61K 39/40* (2006.01)
(52) U.S. Cl. .................................. 424/163.1; 424/165.1
(58) Field of Classification Search .......................... None
See application file for complete search history.

(56) References Cited

U.S. PATENT DOCUMENTS 6,248,329 B1 * 6/2001 Chandrashekar et al. . 424/191.1

OTHER PUBLICATIONS

Feng et al (Infection and Immunity, 64(1):363-365, 1996).*
Ellis, R.W. (Chapter 29 of "VACCINES" [Plotkin, S.A. et al. (eds) published by W. B. Saunders company (Philadelphia) in 1988, especially p. 571, 2nd full paragraph].*
Fahey et al. (Clin. Exp. Immunol. 88: 1-5, 1991).*
Daar et al. (PNAS 87: 6574-6578, 1990).*
Haynes et al. (Science 271: 324-328, 1996).*
Fox (Biotechnology 12: 128, 1994).*
Sommerfelt et al. (J. Gen. Virol. 76: 1345-1352, 1995).*
MSN Encarta Dictionary; definition of treatment and bacteremia.*
Public Health agency of Canada Vaccine Preventable Diseases Rubella, p. 5-15, 2002.*

* cited by examiner

*Primary Examiner* — Patricia A Duffy
(74) *Attorney, Agent, or Firm* — Michael D. Eisenberg

(57) ABSTRACT

Novel vaccines include polypeptides that comprise regions corresponding to a chemokine and a hapten. The hapten can be an amino acid sequence corresponding to the Meningitis Related Homologous Antigenic Sequences (MRHAS) of bacterial and viral agents known to cause meningitis. Protective immunity in a host susceptible to meningitis can be induced by inoculating the host with immunogenic amount of such a vaccine.

3 Claims, 11 Drawing Sheets

FIG. 1

```
              10         20         30         40         50
  1  MASTTPITME DLQKALEAQS RALRAGLAAG ASQSRRPRPP RHARLQHLPE     50
              60         70         80         90        100
 51  MTPAVTPEGP APPRTGAMQR KDNSRAPPPP EERQESRSQT PAPKPSRAPP    100
             110        120        130        140        150
101  QQPQPPRMQT GRGGSAPRPE LGPPTNPFQA AVARGLRPPL HDPDTEAPTE    150
             160        170        180        190        200
151  ACVTSWLWSE GEGAVFYRVD LHFINLGTPP LDEDGRWDPA LMYNPCGPEP    200
             210        220        230        240        250
201  PAHVVRAYNQ PAGDVRGVWG KGERTYAEQD FRVGGTRWHR LLRMPVRGLD    250
             260        270        280        290        300
251  GDTAPLPPHT TERIETRSAR HPWRIRFGAP QAFLAGLLLA AVAVGTARAG    300
             310        320        330        340        350
301  LQPRADMAAP PMPPQPPRAH GQHYGHHHHQ LPFLGHDGHH GGTLRVGQHH    350
             360        370        380        390        400
351  RNASDVLPGH WLQGGWGCYN LSDWHQGTHV CHTKHMDFWC VEHDRPPPAT    400
             410        420        430        440        450
401  PTSLTTAANY IAAATPATAP PPCHAGLNDS CGGFLSGCGP MRLPTALTPG    450
             460        470        480        490        500
451  AVGDLRAVHH RPVPAYPVCC AMRWGLPPWE LVILTARPED GWTCRGVPAH    500
             510        520        530        540        550
501  PGTRCPELVS PMGRATCSPA SALWLATANA LSLDHAFAAF VLLYPWVLIF    550
             560        570        580        590        600
551  MVCRRACRRP APPPPSPQSS CRGTTPPAYG EEAFTYLCTA PGCATQTPVP    600
             610        620        630        640        650
601  VRLAGVGFES KIVDGGCFAP WDLEATGACI CEIPTDVSCE GLGAMVPTAP    650
             660        670        680        690        700
651  CARIWNGTQR ACTFWAVNAY SSGGYAQLAS YFNPGGSYYK QYHPTACEVE    700
             710        720        730        740        750
701  PAFGHSDAAC WGFPTDTVMS VFALASYVQH PHKTVRVKFH TETRTVWQLS    750
             760        770        780        790        800
751  VAGVSCNVTT EHPFCNTPHG QLEVQVPPDP GDLVEYIMNY TGNQQSRMGL    800
             810        820        830        840        850
801  GSPNCHGPDW ASPYCQRHSP DCSRLVGATP ERPRLRLVDA DDPLLRTAPG    850
             860        870        880        890        900
851  PGEVWVTPVI GSQARKCGLH IRAGPYGHAT YEMPEWIHAH TTSDPWHPPG    900
             910        920        930        940        950
901  PLGLKFKTVR PVALPRALAP PRNVRVTGCY QCGTPALVEG LAPGGGNCHL    950
             960        970        980        990       1000
951  TVNGEDVGAF PPGKFVTAAL LNTPPPYQVS CGGESDRASA GH........   1000
```

```
         10         20         30         40         50
  1 MGARASVLSG GELDRWEKIR LRPGGKKKYK LKHIVWASRE LERFAVNPGL    50
         60         70         80         90        100
 51 LETSEGCRQI LGQLQPSLQT GSEELRSLYN TVATLYCVHQ RIEIKDTKEA   100
        110        120        130        140        150
101 LDKIEEEQNK SKKKAQQAAA DTGHSSQVSQ NYPIVQNIQG QMVHQAISPR   150
        160        170        180        190        200
151 TLNAWVKVVE EKAFSPEVIP MFSALSEGAT PQDLNTMLNT VGGHQAAMQM   200
        210        220        230        240        250
201 LKETINEEAA EWDRVHPVHA GPIAPGQMRE PRGSDIAGTT STLQEQIGWM   250
        260        270        280        290        300
251 TNNPPIPVGE IYKRWIILGL NKIVRMYSPT SILDIRQGPK EPFRDYVDRF   300
        310        320        330        340        350
301 YKTLRAEQAS QEVKNWMTET LLVQNANPDC KTILKALGPA ATLEEMMTAC   350
        360        370        380        390        400
351 QGVGGPGHKA RVLAEAMSQV TNTATIMMQR GNFRNQRKMV KCFNCGKEGH   400
        410        420        430        440        450
401 TARNCRAPRK KGCWKCGKEG HQMKDCTERQ ANFLGKICLP TREGQGIFFR   450
        460        470        480        490        500
451 ADQSQQPHHF FRADQSQQPH QKRASGLG..  ..........  ..........   500
```

FIG. 4

```
         10         20         30         40         50
  1 MRVKEKYQHL WRNGWKWGTM LLGILMICSA TEKLWVTVYY GVPVWKEATT      50
         60         70         80         90        100
 51 TLFCASDAKA YDTEVHNVWA THACVPTDPN PQEVVLVNVT ENFNMWKNDM     100
        110        120        130        140        150
101 VEQMHEDIIS LWDQSLKPCV KLTPLCVSLK CTDLGNATNT NSSNTNSSSG     150
        160        170        180        190        200
151 EMMMEKGEIK NCSFNISTSI RGKVQKEYAF FYKLDIIPID NDTTSYTLTS     200
        210        220        230        240        250
201 CNTSVITQAC PKVSFEPIPI HYCAPAGFAI LKCNNKTFNG TGPCTNVSTV     250
        260        270        280        290        300
251 QCTHGIRPVV STQLLLNGSL AEEEVVIRSA NFTDNAKTII VQLNQSVEIN     300
        310        320        330        340        350
301 CTRPNNNTRK SIRIQRGPGR AFVTIGKIGN MRQAHCNISR AKWNATLKQI     350
        360        370        380        390        400
351 ASKLREQFGN NKTIIFKQSS GGDPEIVTHS FNCGGEFFYC NSTQLFNSTW     400
        410        420        430        440        450
401 FNSTWSTEGS NNTEGSDTIT LPCRIKQFIN MWQEVGKAMY APPISGQIRC     450
        460        470        480        490        500
451 SSNITGLLLT RDGGNNNNGS EIFRPGGGDM RDNWRSELYK YKVVKIEPLG     500
        510        520        530        540        550
501 VAPTKAKRRV VQREKRAVGI GALFLGFLGA AGSTMGARSM TLTVQARQLL     550
        560        570        580        590        600
551 SGIVQQQNNL LRAIEAQQHL LQLTVWGIKQ LQARILAVER YLKDQQLLGI     600
        610        620        630        640        650
601 WGCSGKLICT TAVPWNASWS NKSLEQIWNN MTWMEWDREI NNYTSLIHSL     650
        660        670        680        690        700
651 IEESQNQQEK NEQELLELDK WASLWNWFNI TNWLWYIKIF IMIVGGLVGL     700
        710        720        730        740        750
701 RIVFAVLSIV NRVRQGYSPL SFQTHLPTPR GPDRPEGIEE EGGERDRDRS     750
        760        770        780        790        800
751 IRLVNGSLAL IWDDLRSLCL FSYHRLRDLL LIVTRIVELL GRRGWEALKY     800
        810        820        830        840        850
801 WWNLLQYWSQ ELKNSAVSLL NATAIAVAEG TDRVIEVVQG ACRAIRHIPR     850
        860        870        880        890        900
851 RIRQGLERIL L.........  .........  .........  .........    900
```

FIG. 5

```
            10         20         30         40         50
    1 MKTTLKMTAL AALSAFVLAG CGSHQMKSEE HANMQLQQQA VLGLNWMQDS      50
            60         70         80         90        100
   51 GEYKALAYQA YNAAKVAFDH AKVAKGKKKA VVADLDETML DNSPYAGWQV     100
           110        120        130        140        150
  101 QNNKPFDGKD WTRWVDARQS RAVPGAVEFN NYVNSHNGKV FYVTNRKDST     150
           160        170        180        190        200
  151 EKSGTIDDMK RLGFNGVEES AFYLKKDKSA KAARFAEIEK QGYEIVLYVG     200
           210        220        230        240        250
  201 DNLDDFGNTV YGKLNADRRA FVDQNQGKFG KTFIHLPNAN YGGWEGGLAE     250
           260        270        280        290        300
  251 GYFKKDTQGQ IKARLDAVQA WDGK......                          300
```

FIG. 6

```
           10         20         30         40         50
  1  IQPPKNLLFS SLLFSSLLFS SAAQAASEDR RSPYYVQADL AYAAERITHD   50
           60         70         80         90        100
 51  YPQATGANNT STVSDYFRNI RAHSIHPRVS VGYDFGGWRI AADYASYRKW  100
          110        120        130        140        150
101  NNNKYSVNTK ELENKHNNKK DLKTENQENG TFHAASSLGL SAIYDFKLKG  150
          160        170        180        190        200
151  KFKPYIGARV AYGHVRHSID                                   200
```

FIG. 9

```
           10         20         30         40         50
  1  MKVSAALLCL LLIAATFIPQ GLAQPDAINA PVTCCYNFTN RKISVQRLAS   50
           60         70         80         90        100
 51  YRRITSSKCP KEAVIFKTIV AKEICADPKQ KWVQDSMDHL DKQTQTPKT.  100
```

FIG. 10

```
           10         20         30         40         50
  1  KSTTCCYRFI NKKIPKQRLE SYRRTTSSHC PREAVIFKDK EICADPTQKW   50
           60         70         80         90        100
 51  VQDFMKHLDK KTQTPKL...                                   100
```

FIG. 7

```
                                         -11            -1
                                          ............
                                          ....KLMI*K                    6
           10          20          30          40          50
      ............  ............  ............  ............  ............
  7   FVTKM*YKTL  DKYLRRRLIL  NISIV*K*LS  EKR*I*MNKK  KMILTSLASV        56

60          70          80          90         100
      ............  ............  ............  ............  ............
 57   AILGAGFVAS  QPTVVRAEES  PVASQSKAEK  DYDAAKKDAK  NAKKAVEDAQ       106

110         120         130         140         150
      ............  ............  ............  ............  ............
107   KALDDAKAAQ  KKYDEDQKKT  EEKAALEKAA  SEEMDKAVAA  VQQAYLAYQQ       156

160         170         180         190         200
      ............  ............  ............  ............  ............
157   ATDKAAKDAA  DKMIDEAKKR  EEEAKTKFNT  VRAMVVPEPE  QLAETKKKSE       206

210         220         230         240         250
      ............  ............  ............  ............  ............
207   EAKQKAPELT  KKLEEAKAKL  EEAEKKATEA  KQKVDAEEVA  PQAKIAELEN       256

260         270         280         290         300
      ............  ............  ............  ............  ............
257   QVHRLEQELK  EIDESESEDY  AKEGFRAPLQ  SKLDAKKAKL  SKLEELSDKI       306

310         320         330         340         350
      ............  ............  ............  ............  ............
307   DELDAEIAKL  EDQLKAAEEN  NNVEDYFKEG  LEKTIAAKKA  ELEKTEADLK       356

360         370         380         390         400
      ............  ............  ............  ............  ............
357   KAVNEPEKPA  PAPETPAPEA  PAEQPKPAPA  PQPAPAPKPE  KPAEQPKPEK       406

410         420         430         440         450
      ............  ............  ............  ............  ............
407   TDDQQAEEDY  ARRSEEEYNR  LTQQQPPKAE  KPAPAPKTGW  KQENGMWYFY       456

460         470         480         490         500
      ............  ............  ............  ............  ............
457   NTDGSMATGW  LQNNGSWYYL  NSHGAMATGW  LQYNGSWYYL  NANGAMATGW       506

510         520         530         540         550
      ............  ............  ............  ............  ............
507   AKVNGSWYYL  NANGAMATGW  LQYNGSWYYL  NANGAMATGW  AKVNGSWYYL       556

560         570         580         590         600
      ............  ............  ............  ............  ............
557   NANGAMATGW  LQYNGSWYYL  NANGAMATGW  AKVNGSWYYL  NANGAMATGW       606

610         620         630         640         650
      ............  ............  ............  ............  ............
607   VKDGDTWYYL  EASGAMKASQ  WFKVSDKWYY  VNGLGALAVN  TTVDGYKVNA       656

660         670         680         690         700
      ............  ............  ............  ............  ............
657   NGEWV*AD*I  KAC*EHLTF*  F*NKDKVRLN  RFMFVFFRY.  ............      706
```

FIG. 8

```
              10          20          30          40          50
  1  MNMKKATIAA  TAGIAVTAFR  APTIRSASTV  VVEAGDTLWG  IAQSKGTTVD        50
              60          70          80          90         100
 51  AIKKANNLTT  DKIVPGQKLQ  VHNEVAAAEK  TEKSVSATWL  NVRSGAGVDN       100
             110         120         130         140         150
101  SIITSIKGGT  KVTVETTESN  GWHKITYNDG  KTGFVNGKYL  TDKAVSTPVA       150
             160         170         180         190         200
151  PTQEVKKETT  TQQAAPAAET  KTEVKQTTQA  TTPAPKVAET  KETPVVDQNA       200
             210         220         230         240         250
201  TTHAVKSGDT  IWALSVKYGV  SVQDIMSWNN  LSSSSIYVGQ  KLAIKQTANT       250
             260         270         280         290         300
251  ATPKAEVKTE  APAAEKQAAP  VVKENTNTNT  ATTEKKETAT  QQQTAPKAPT       300
             310         320         330         340         350
301  EAAKPAPAPS  TNTNANKTNT  NTNTNTNTNN  TNTNTPSKNT  NTNSNTNTNT       350
             360         370         380         390         400
351  NSNTNANQGS  SNNNSNSSAS  AIIAEAQKHL  GKAYSWGGNG  PTTFDCSGYT       400
             410         420         430         440         450
401  KYVFAKAGIS  LPRTSGAQYA  STTRISESQA  KPGDLVFFDY  GSGISHVGIY       450
             460         470         480         490         500
451  VGNGQMINAQ  DNGVKYDNIH  GSGWGKYLVG  FGRV......  ..........       500
```

Immunoblots of RV antigens reacted with Mab's RV1, RV2, RV3 and RV4. RV antigen: Strain MPV-77 (lot# 50678, Catalogue# EL-05-04) cultured in Vero cells. Purchased from Microbix Biosystems Inc., Toronto, Ontario). All Mab used as tissue culture fluid diluted 1/500.
Lane 1 - Molecular weight Markers of 97, 66, 45, 31, 21, and 14 kD.
Lane 2/3 - RV4; Lane 4/5/6 - RV3; Lane7/8 - RV2; Lane 9/10 - RV1
Lanes 2-9 all illustrate two proteins, 31 kD (major) and 45 kD (minor), identified by reaction with Mab's 1-4

FIG. 12

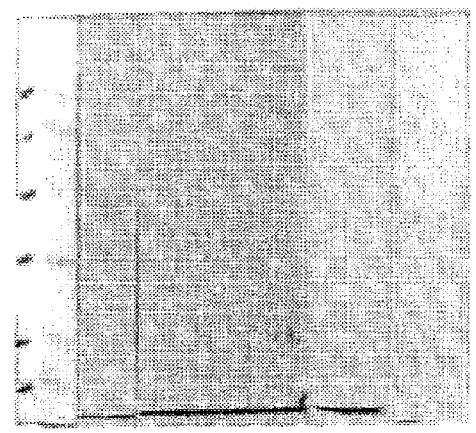

1   2   3   4/5   6/7

Immunoblots of bacterial antigens reacted with RV Mab RV1.
H.influenzae b antigen from ATCC (#10211); L.monocytogenes from ATCC (#7644); S.pneumoniae from the Caribbean Regional Epidemiology Centre, CAREC, Trinidad; N.meningitidis A from ATCC (#13077).
Lane 1 - Molecular weight markers of 97, 66, 45, 31, 21, and 14 kD.
Lane 2 - H.influenzae b - proteins of approximate weights of 50, 45, 40, and 25 kD.
Lane 3 - L.monocytogenes - proteins of approximate weights of 60 kD (major) and 66 kD (minor).
Lane 4/5 - S.pneumoniae - proteins of approximate weights of 60 kD and 66 kD.
Lane 6/7 - N.meningitidis - a protein of an approximate weight of 18 kD. All proteins identified by reaction with Mab RV1.

1  2  3/4

Immunoblots of HIV1 antigens reacted with RV Mab RV1.
HTLV-IIIB viral lysate, lot #54-040, purchased from Applied Biotechnologies, Inc., Md., USA.
Lane 1 - Molecular weight markers of 97, 66, 45, 31, 21, and 14 kD.
Lane 2 - Control RV antigens, 31 and 45 kD, reacting with RV1 Mab.
Lane 3/4 - HIV1 proteins of approximate weights of 24 kD and 61 kD, identified by reaction with Mab RV1.

```
                              SEQUENCE LISTING (1) GENERAL INFORMATION:

(iii) NUMBER OF SEQUENCES: 75

(2) INFORMATION FOR SEQ ID NO: 1:

(i) SEQUENCE CHARACTERISTICS:
          (A) LENGTH: 992 amino acids
          (B) TYPE: amino acid
          (C) STRANDEDNESS: <Unknown>
          (D) TOPOLOGY: unknown (xi) SEQUENCE DESCRIPTION: SEQ ID NO: 1:

Met Ala Ser Thr Thr Pro Ile Thr Met Glu Asp Leu Gln Lys Ala Leu
1               5                   10                  15

Glu Ala Gln Ser Arg Ala Leu Arg Ala Gly Leu Ala Ala Gly Ala Ser
            20                  25                  30

Gln Ser Arg Arg Pro Arg Pro Pro Arg His Ala Arg Leu Gln His Leu
        35                  40                  45

Pro Glu Met Thr Pro Ala Val Thr Pro Glu Gly Pro Ala Pro Pro Arg
    50                  55                  60

Thr Gly Ala Trp Gln Arg Lys Asp Trp Ser Arg Ala Pro Pro Pro Pro
65                  70                  75                  80

Glu Glu Arg Gln Glu Ser Arg Ser Gln Thr Pro Ala Pro Lys Pro Ser
                85                  90                  95

Arg Ala Pro Pro Gln Gln Pro Gln Pro Pro Arg Met Gln Thr Gly Arg
            100                 105                 110

Gly Gly Ser Ala Pro Arg Pro Glu Leu Gly Pro Pro Thr Asn Pro Phe
        115                 120                 125

Gln Ala Ala Val Ala Arg Gly Leu Arg Pro Pro Leu His Asp Pro Asp
    130                 135                 140

Thr Glu Ala Pro Thr Glu Ala Cys Val Thr Ser Trp Leu Trp Ser Glu
145                 150                 155                 160
```

-continued

```
Gly Glu Gly Ala Val Phe Tyr Arg Val Asp Leu His Phe Ile Asn Leu
                165                 170                 175
Gly Thr Pro Pro Leu Asp Glu Asp Gly Arg Trp Asp Pro Ala Leu Met
            180                 185                 190
Tyr Asn Pro Cys Gly Pro Glu Pro Pro Ala His Val Val Arg Ala Tyr
        195                 200                 205
Asn Gln Pro Ala Gly Asp Val Arg Gly Val Trp Gly Lys Gly Glu Arg
    210                 215                 220
Thr Tyr Ala Glu Gln Asp Phe Arg Val Gly Thr Arg Trp His Arg
225                 230                 235                 240
Leu Leu Arg Met Pro Val Arg Gly Leu Asp Gly Asp Thr Ala Pro Leu
                245                 250                 255
Pro Pro His Thr Thr Glu Arg Ile Glu Thr Arg Ser Ala Arg His Pro
            260                 265                 270
Trp Arg Ile Arg Phe Gly Ala Pro Gln Ala Phe Leu Ala Gly Leu Leu
        275                 280                 285
Leu Ala Ala Val Ala Val Gly Thr Ala Arg Ala Gly Leu Gln Pro Arg
    290                 295                 300
Ala Asp Met Ala Ala Pro Pro Met Pro Gln Pro Pro Arg Ala His
305                 310                 315                 320
Gly Gln His Tyr Gly His His His Gln Leu Pro Phe Leu Gly His
                325                 330                 335
Asp Gly His His Gly Gly Thr Leu Arg Val Gly Gln His His Arg Asn
            340                 345                 350
Ala Ser Asp Val Leu Pro Gly His Trp Leu Gln Gly Trp Gly Cys
        355                 360                 365
Tyr Asn Leu Ser Asp Trp His Gln Gly Thr His Val Cys His Thr Lys
    370                 375                 380
His Met Asp Phe Trp Cys Val Glu His Asp Arg Pro Pro Ala Thr
385                 390                 395                 400
Pro Thr Ser Leu Thr Thr Ala Ala Asn Tyr Ile Ala Ala Ala Thr Pro
                405                 410                 415
Ala Thr Ala Pro Pro Pro Cys His Ala Gly Leu Asn Asp Ser Cys Gly
            420                 425                 430
Gly Phe Leu Ser Gly Cys Gly Pro Met Arg Leu Pro Thr Ala Leu Thr
        435                 440                 445
Pro Gly Ala Val Gly Asp Leu Arg Ala Val His His Arg Pro Val Pro
    450                 455                 460
Ala Tyr Pro Val Cys Cys Ala Met Arg Trp Gly Leu Pro Trp Glu
465                 470                 475                 480
Leu Val Ile Leu Thr Ala Arg Pro Glu Asp Gly Trp Thr Cys Arg Gly
                485                 490                 495
Val Pro Ala His Pro Gly Thr Arg Cys Pro Glu Leu Val Ser Pro Met
            500                 505                 510
Gly Arg Ala Thr Cys Ser Pro Ala Ser Ala Leu Trp Leu Ala Thr Ala
        515                 520                 525
Asn Ala Leu Ser Leu Asp His Ala Phe Ala Ala Phe Val Leu Leu Val
    530                 535                 540
Pro Trp Val Leu Ile Phe Met Val Cys Arg Arg Ala Cys Arg Arg Pro
545                 550                 555                 560
Ala Pro Pro Pro Ser Pro Gln Ser Ser Cys Arg Gly Thr Thr Pro
                565                 570                 575
Pro Ala Tyr Gly Glu Glu Ala Phe Thr Tyr Leu Cys Thr Ala Pro Gly
            580                 585                 590
```

```
Cys Ala Thr Gln Thr Pro Val Pro Val Arg Leu Ala Gly Val Gly Phe
            595                 600                 605

Glu Ser Lys Ile Val Asp Gly Gly Cys Phe Ala Pro Trp Asp Leu Glu
            610                 615                 620

Ala Thr Gly Ala Cys Ile Cys Glu Ile Pro Thr Asp Val Ser Cys Glu
625                 630                 635                 640

Gly Leu Gly Ala Trp Val Pro Thr Ala Pro Cys Ala Arg Ile Trp Asn
                645                 650                 655

Gly Thr Gln Arg Ala Cys Thr Phe Trp Ala Val Asn Ala Tyr Ser Ser
            660                 665                 670

Gly Gly Tyr Ala Gln Leu Ala Ser Tyr Phe Asn Pro Gly Gly Ser Tyr
            675                 680                 685

Tyr Lys Gln Tyr His Pro Thr Ala Cys Glu Val Glu Pro Ala Phe Gly
            690                 695                 700

His Ser Asp Ala Ala Cys Trp Gly Phe Pro Thr Asp Thr Val Met Ser
705                 710                 715                 720

Val Phe Ala Leu Ala Ser Tyr Val Gln His Pro His Lys Thr Val Arg
                725                 730                 735

Val Lys Phe His Thr Glu Thr Arg Thr Val Trp Gln Leu Ser Val Ala
            740                 745                 750

Gly Val Ser Cys Asn Val Thr Thr Glu His Pro Phe Cys Asn Thr Pro
            755                 760                 765

His Gly Gln Leu Glu Val Gln Val Pro Pro Asp Pro Gly Asp Leu Val
            770                 775                 780

Glu Tyr Ile Met Asn Tyr Thr Gly Asn Gln Gln Ser Arg Trp Gly Leu
785                 790                 795                 800

Gly Ser Pro Asn Cys His Gly Pro Asp Trp Ala Ser Pro Val Cys Gln
                805                 810                 815

Arg His Ser Pro Asp Cys Ser Arg Leu Val Gly Ala Thr Pro Glu Arg
            820                 825                 830

Pro Arg Leu Arg Leu Val Asp Ala Asp Pro Leu Leu Arg Thr Ala
            835                 840                 845

Pro Gly Pro Gly Glu Val Trp Val Thr Pro Val Ile Gly Ser Gln Ala
            850                 855                 860

Arg Lys Cys Gly Leu His Ile Arg Ala Gly Pro Tyr Gly His Ala Thr
865                 870                 875                 880

Val Glu Met Pro Glu Trp Ile His Ala His Thr Thr Ser Asp Pro Trp
                885                 890                 895

His Pro Pro Gly Pro Leu Gly Leu Lys Phe Lys Thr Val Arg Pro Val
            900                 905                 910

Ala Leu Pro Arg Ala Leu Ala Pro Pro Arg Asn Val Arg Val Thr Gly
            915                 920                 925

Cys Tyr Gln Cys Gly Thr Pro Ala Leu Val Glu Gly Leu Ala Pro Gly
            930                 935                 940

Gly Gly Asn Cys His Leu Thr Val Asn Gly Glu Asp Val Gly Ala Phe
945                 950                 955                 960

Pro Pro Gly Lys Phe Val Thr Ala Ala Leu Leu Asn Thr Pro Pro Pro
                965                 970                 975

Tyr Gln Val Ser Cys Gly Gly Glu Ser Asp Arg Ala Ser Ala Gly His
            980                 985                 990
```

(2) INFORMATION FOR SEQ ID NO: 2:

(i) SEQUENCE CHARACTERISTICS:

```
        (A) LENGTH: 21 amino acids
        (B) TYPE: amino acid
        (C) STRANDEDNESS: <Unknown>
        (D) TOPOLOGY: unknown (xi) SEQUENCE DESCRIPTION: SEQ ID NO: 2:

Pro Ser Arg Ala Pro Pro Gln Gln Pro Gln Pro Pro Arg Met Gln Thr
1               5                   10                  15

Gly Arg Gly Gly Ser
            20

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 3:

Gln Pro Gln Pro Pro Arg Met
1               5

(2) INFORMATION FOR SEQ ID NO: 4:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (xi) SEQUENCE DESCRIPTION: SEQ ID NO: 4:

Glu Arg Gln Glu Ser Arg Ser Gln Thr Pro Ala Pro Lys Pro Ser Arg
1               5                   10                  15

Ala Pro Pro Gln Gln
            20

(2) INFORMATION FOR SEQ ID NO: 5:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 5:

Gln Thr Pro Ala Pro Lys Pro
1               5

(2) INFORMATION FOR SEQ ID NO: 6:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (xi) SEQUENCE DESCRIPTION: SEQ ID NO: 6:

Asp Met Ala Ala Pro Pro Met Pro Pro Gln Pro Pro Arg Ala His Gly
1               5                   10                  15

Gln His Tyr Gly His
            20

(2) INFORMATION FOR SEQ ID NO: 7:

(i) SEQUENCE CHARACTERISTICS:
        (A) LENGTH: 7 amino acids
```

(B) TYPE: amino acid
        (C) STRANDEDNESS: <Unknown>
        (D) TOPOLOGY: unknown (xi) SEQUENCE DESCRIPTION: SEQ ID NO: 7:

Pro Pro Gln Pro Pro Arg Ala
1               5

(2) INFORMATION FOR SEQ ID NO: 8:

(i) SEQUENCE CHARACTERISTICS:
        (A) LENGTH: 1063 amino acids
        (B) TYPE: amino acid
        (C) STRANDEDNESS: <Unknown>
        (D) TOPOLOGY: unknown (xi) SEQUENCE DESCRIPTION: SEQ ID NO: 8:

Met Ala Ser Thr Thr Pro Ile Thr Met Glu Asp Leu Gln Lys Ala Leu
1               5                   10                  15

Glu Ala Gln Ser Arg Ala Leu Arg Ala Glu Leu Ala Ala Gly Ala Ser
            20                  25                  30

Gln Ser Arg Arg Pro Arg Pro Pro Arg Gln Arg Asp Ser Ser Thr Ser
        35                  40                  45

Gly Asp Asp Ser Gly Arg Asp Ser Gly Gly Pro Arg Arg Arg Arg Gly
50                  55                  60

Asn Arg Gly Arg Gly Gln Arg Arg Asp Trp Ser Arg Ala Pro Pro Pro
65                  70                  75                  80

Pro Glu Glu Arg Gln Glu Ser Arg Ser Gln Thr Pro Ala Pro Lys Pro
            85                  90                  95

Ser Arg Ala Pro Pro Gln Gln Pro Gln Pro Pro Arg Met Gln Thr Gly
            100                 105                 110

Arg Gly Gly Ser Ala Pro Arg Pro Glu Leu Gly Pro Pro Thr Asn Pro
            115                 120                 125

Phe Gln Ala Ala Val Ala Arg Gly Leu Arg Pro Leu His Asp Pro
            130             135                 140

Asp Thr Glu Ala Pro Thr Glu Ala Cys Val Thr Ser Trp Leu Trp Ser
145                 150                 155                 160

Glu Gly Gln Gly Ala Val Phe Tyr Arg Val Asp Leu His Phe Thr Asn
            165                 170                 175

Leu Gly Thr Pro Pro Leu Asp Glu Asp Gly Arg Trp Asp Pro Ala Leu
            180                 185                 190

Met Tyr Asn Pro Cys Gly Pro Glu Pro Pro Ala His Val Val Arg Ala
            195                 200                 205

Tyr Asn Gln Pro Ala Gly Asp Val Arg Gly Val Trp Gly Lys Gly Glu
            210                 215                 220

Arg Thr Tyr Ala Glu Gln Asp Phe Arg Val Gly Gly Thr Arg Trp His
225                 230                 235                 240

Arg Leu Leu Arg Met Pro Val Arg Gly Leu Asp Gly Asp Ser Ala Pro
            245                 250                 255

Leu Pro Pro His Thr Thr Glu Arg Ile Glu Thr Arg Ser Ala Arg His
            260                 265                 270

Pro Trp Arg Ile Arg Phe Gly Ala Pro Gln Ala Phe Leu Ala Gly Leu
            275                 280                 285

Leu Leu Ala Thr Val Ala Val Gly Thr Ala Arg Ala Gly Leu Gln Pro
            290                 295                 300

Arg Ala Asp Met Ala Ala Pro Pro Thr Leu Pro Gln Pro Pro Cys Ala
305                 310                 315                 320

-continued

```
His Gly Gln His Tyr Gly His His His Gln Leu Pro Phe Leu Gly
                325                 330                 335

His Asp Gly His His Gly Gly Thr Leu Arg Val Gly Gln His Tyr Arg
            340                 345                 350

Asn Ala Ser Asp Val Leu Pro Gly His Trp Leu Gln Gly Gly Trp Gly
        355                 360                 365

Cys Tyr Asn Leu Ser Asp Trp His Gln Gly Thr His Val Cys His Thr
    370                 375                 380

Lys His Met Asp Phe Trp Cys Val Glu His Ala Arg Pro Pro Pro Ala
385                 390                 395                 400

Thr Pro Thr Pro Leu Thr Thr Ala Ala Asn Ser Thr Ala Ala Thr
                405                 410                 415

Pro Ala Thr Ala Pro Ala Pro Cys His Ala Gly Leu Asn Asp Ser Cys
            420                 425                 430

Gly Gly Phe Leu Ser Gly Cys Gly Pro Met Arg Leu Arg His Gly Ala
        435                 440                 445

Asp Thr Arg Cys Gly Arg Leu Ile Cys Gly Leu Ser Thr Thr Ala Gln
    450                 455                 460

Tyr Pro Pro Thr Arg Phe Gly Cys Ala Met Arg Trp Gly Leu Pro Pro
465                 470                 475                 480

Trp Glu Leu Val Val Leu Thr Ala Arg Pro Glu Asp Gly Trp Thr Cys
                485                 490                 495

Arg Gly Val Pro Ala His Pro Gly Ala Arg Cys Pro Glu Leu Val Ser
            500                 505                 510

Pro Met Gly Arg Ala Thr Cys Ser Pro Ala Ser Ala Leu Trp Leu Ala
        515                 520                 525

Thr Ala Asn Ala Leu Ser Leu Asp His Ala Leu Ala Ala Phe Val Leu
    530                 535                 540

Ser Val Pro Trp Val Leu Ile Phe Met Val Cys Arg Arg Ala Cys Arg
545                 550                 555                 560

Arg Arg Gly Ala Ala Ala Ala Leu Thr Ala Val Val Leu Gln Gly Tyr
                565                 570                 575

Asn Pro Pro Ala Tyr Gly Glu Glu Ala Phe Thr Tyr Leu Cys Thr Ala
            580                 585                 590

Pro Gly Cys Ala Thr Gln Ala Pro Val Pro Val Arg Leu Ala Gly Val
        595                 600                 605

Arg Phe Glu Ser Lys Ile Val Asp Gly Gly Cys Phe Ala Pro Trp Asp
    610                 615                 620

Leu Glu Ala Thr Gly Ala Cys Ile Cys Glu Ile Pro Thr Asp Val Ser
625                 630                 635                 640

Cys Glu Gly Leu Gly Ala Trp Val Pro Ala Ala Pro Cys Ala Arg Ile
                645                 650                 655

Trp Asn Gly Thr Gln Arg Ala Cys Thr Phe Trp Ala Val Asn Ala Tyr
            660                 665                 670

Ser Ser Gly Gly Tyr Ala Gln Leu Ala Ser Tyr Phe Asn Pro Gly Gly
        675                 680                 685

Ser Tyr Tyr Lys Gln Tyr His Pro Thr Ala Cys Glu Val Glu Pro Ala
    690                 695                 700

Phe Gly His Ser Asp Ala Ala Cys Trp Gly Phe Pro Thr Asp Thr Val
705                 710                 715                 720

Met Ser Val Phe Ala Leu Ala Ser Tyr Val Gln His Pro His Lys Thr
                725                 730                 735

Val Arg Val Lys Phe His Thr Glu Thr Arg Thr Val Trp Gln Leu Ser
            740                 745                 750
```

-continued

```
Val Ala Gly Val Ser Cys Asn Val Thr Thr Glu His Pro Phe Cys Asn
            755                 760                 765

Thr Pro His Gly Gln Leu Glu Val Gln Val Pro Pro Asp Pro Gly Asp
770                 775                 780

Leu Val Glu Tyr Ile Met Asn Tyr Thr Gly Asn Gln Ser Arg Trp
785                 790                 795                 800

Gly Leu Gly Ser Pro Asn Cys His Gly Pro Asp Trp Ala Ser Pro Val
            805                 810                 815

Cys Gln Arg His Ser Pro Asp Cys Ser Arg Leu Val Gly Ala Thr Pro
            820                 825                 830

Glu Arg Pro Arg Leu Arg Leu Val Asp Ala Asp Pro Leu Leu Arg
            835                 840                 845

Thr Ala Pro Gly Pro Gly Glu Val Trp Val Thr Pro Val Ile Gly Ser
            850                 855                 860

Gln Ala Arg Lys Cys Gly Leu His Ile Arg Ala Gly Pro Tyr Gly His
865                 870                 875                 880

Ala Thr Val Glu Met Pro Glu Trp Ile His Ala His Thr Thr Ser Asp
                885                 890                 895

Pro Trp His Pro Pro Gly Pro Leu Gly Leu Lys Phe Lys Thr Val Arg
            900                 905                 910

Pro Val Ala Leu Pro Arg Thr Leu Ala Pro Pro Arg Asn Val Arg Val
            915                 920                 925

Thr Gly Cys Tyr Gln Cys Gly Thr Pro Ala Leu Val Glu Gly Leu Ala
930                 935                 940

Pro Gly Gly Gly Asn Cys His Leu Thr Val Asn Gly Glu Asp Val Gly
945                 950                 955                 960

Ala Val Pro Pro Gly Lys Phe Val Thr Ala Ala Leu Leu Asn Thr Pro
                965                 970                 975

Pro Pro Tyr Gln Val Ser Cys Gly Gly Glu Ser Asp Arg Ala Ser Ala
            980                 985                 990

Arg Val Ile Asp Pro Ala Ala Gln Ser Phe Thr Gly Val Val Tyr Gly
            995                 1000                1005

Thr His Thr Thr Ala Val Ser Glu Thr Arg Gln Thr Trp Ala Glu Trp
    1010                1015                1020

Ala Ala Ala His Trp Trp Gln Leu Thr Leu Gly Ala Thr Cys Ala Leu
1025                1030                1035                1040

Pro Leu Ala Gly Leu Leu Ala Cys Cys Ala Lys Cys Leu Tyr Tyr Leu
                1045                1050                1055

Arg Gly Ala Ile Ala Pro Arg
            1060

(2) INFORMATION FOR SEQ ID NO: 9:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (xi) SEQUENCE DESCRIPTION: SEQ ID NO: 9:

Asp Met Ala Ala Pro Pro Thr Leu Pro Gln Pro Pro Arg Ala His Gly
1               5                   10                  15

Gln His Tyr Gly His
            20

(2) INFORMATION FOR SEQ ID NO: 10:
```

```
        (i) SEQUENCE CHARACTERISTICS:
            (A) LENGTH: 7 amino acids
            (B) TYPE: amino acid
            (C) STRANDEDNESS: <Unknown>
            (D) TOPOLOGY: unknown (xi) SEQUENCE DESCRIPTION: SEQ ID NO: 10:

Leu Pro Gln Pro Pro Cys Ala
1                5

(2) INFORMATION FOR SEQ ID NO: 11:

(i) SEQUENCE CHARACTERISTICS:
            (A) LENGTH: 478 amino acids
            (B) TYPE: amino acid
            (C) STRANDEDNESS: <Unknown>
            (D) TOPOLOGY: unknown (xi) SEQUENCE DESCRIPTION: SEQ ID NO: 11:

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300
```

```
Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Thr Ala Thr Ile Met Met Gln Arg Gly Asn Phe Arg
370                 375                 380

Asn Gln Arg Lys Met Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Cys Leu Pro Thr Arg Glu Gly Gln Gly Ile Phe
        435                 440                 445

Phe Arg Ala Asp Gln Ser Gln Gln Pro His His Phe Phe Arg Ala Asp
    450                 455                 460

Gln Ser Gln Gln Pro His Gln Lys Arg Ala Ser Gly Leu Gly
465                 470                 475
```

(2) INFORMATION FOR SEQ ID NO: 12:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (xi) SEQUENCE DESCRIPTION: SEQ ID NO: 12:

```
Ile Gln Gly Gln Met Val His Gln Ala Ile Ser Pro Arg Thr Leu Asn
1               5                   10                  15

Ala Trp Val Lys Val
            20
```

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 13:

```
Gln Ala Ile Ser Pro Arg Thr
1               5
```

(2) INFORMATION FOR SEQ ID NO: 14:

(i) SEQUENCE CHARACTERISTICS:
        (A) LENGTH: 861 amino acids
        (B) TYPE: amino acid
        (C) STRANDEDNESS: <Unknown>
        (D) TOPOLOGY: unknown (xi) SEQUENCE DESCRIPTION: SEQ ID NO: 14:

```
Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30
```

```
Lys Leu Trp Val Thr Val Tyr Tyr Gly Val Pro Val Trp Lys Glu Ala
             35                  40                  45

Thr Thr Thr Leu Phe Cys Ala Ser Asp Ala Lys Ala Tyr Asp Thr Glu
     50                  55                  60

Val His Asn Val Trp Ala Thr His Ala Cys Val Pro Thr Asp Pro Asn
 65                  70                  75                  80

Pro Gln Glu Val Val Leu Val Asn Val Thr Glu Asn Phe Asn Met Trp
                 85                  90                  95

Lys Asn Asp Met Val Glu Gln Met His Glu Asp Ile Ile Ser Leu Trp
             100                 105                 110

Asp Gln Ser Leu Lys Pro Cys Val Lys Leu Thr Pro Leu Cys Val Ser
             115                 120                 125

Leu Lys Cys Thr Asp Leu Gly Asn Ala Thr Asn Thr Asn Ser Ser Asn
         130                 135                 140

Thr Asn Ser Ser Ser Gly Glu Met Met Met Glu Lys Gly Glu Ile Lys
145                 150                 155                 160

Asn Cys Ser Phe Asn Ile Ser Thr Ser Ile Arg Gly Lys Val Gln Lys
                 165                 170                 175

Glu Tyr Ala Phe Phe Tyr Lys Leu Asp Ile Ile Pro Ile Asp Asn Asp
             180                 185                 190

Thr Thr Ser Tyr Thr Leu Thr Ser Cys Asn Thr Ser Val Ile Thr Gln
         195                 200                 205

Ala Cys Pro Lys Val Ser Phe Glu Pro Ile Pro Ile His Tyr Cys Ala
         210                 215                 220

Pro Ala Gly Phe Ala Ile Leu Lys Cys Asn Asn Lys Thr Phe Asn Gly
225                 230                 235                 240

Thr Gly Pro Cys Thr Asn Val Ser Thr Val Gln Cys Thr His Gly Ile
                 245                 250                 255

Arg Pro Val Val Ser Thr Gln Leu Leu Leu Asn Gly Ser Leu Ala Glu
             260                 265                 270

Glu Glu Val Val Ile Arg Ser Ala Asn Phe Thr Asp Asn Ala Lys Thr
         275                 280                 285

Ile Ile Val Gln Leu Asn Gln Ser Val Glu Ile Asn Cys Thr Arg Pro
         290                 295                 300

Asn Asn Asn Thr Arg Lys Ser Ile Arg Ile Gln Arg Gly Pro Gly Arg
305                 310                 315                 320

Ala Phe Val Thr Ile Gly Lys Ile Gly Asn Met Arg Gln Ala His Cys
                 325                 330                 335

Asn Ile Ser Arg Ala Lys Trp Asn Ala Thr Leu Lys Gln Ile Ala Ser
             340                 345                 350

Lys Leu Arg Glu Gln Phe Gly Asn Asn Lys Thr Ile Ile Phe Lys Gln
         355                 360                 365

Ser Ser Gly Gly Asp Pro Glu Ile Val Thr His Ser Phe Asn Cys Gly
     370                 375                 380

Gly Glu Phe Phe Tyr Cys Asn Ser Thr Gln Leu Phe Asn Ser Thr Trp
385                 390                 395                 400

Phe Asn Ser Thr Trp Ser Thr Glu Gly Ser Asn Asn Thr Glu Gly Ser
                 405                 410                 415

Asp Thr Ile Thr Leu Pro Cys Arg Ile Lys Gln Phe Ile Asn Met Trp
             420                 425                 430

Gln Glu Val Gly Lys Ala Met Tyr Ala Pro Pro Ile Ser Gly Gln Ile
         435                 440                 445

Arg Cys Ser Ser Asn Ile Thr Gly Leu Leu Leu Thr Arg Asp Gly Gly
```

```
                    450                 455                 460
Asn Asn Asn Asn Gly Ser Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
                500                 505                 510

Arg Glu Lys Arg Ala Val Gly Ile Gly Ala Leu Phe Leu Gly Phe Leu
                515                 520                 525

Gly Ala Ala Gly Ser Thr Met Gly Ala Arg Ser Met Thr Leu Thr Val
530                 535                 540

Gln Ala Arg Gln Leu Leu Ser Gly Ile Val Gln Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Ile Leu Ala Val Glu Arg Tyr Leu
                580                 585                 590

Lys Asp Gln Gln Leu Leu Gly Ile Trp Gly Cys Ser Gly Lys Leu Ile
                595                 600                 605

Cys Thr Thr Ala Val Pro Trp Asn Ala Ser Trp Ser Asn Lys Ser Leu
610                 615                 620

Glu Gln Ile Trp Asn Asn Met Thr Trp Met Glu Trp Asp Arg Glu Ile
625                 630                 635                 640

Asn Asn Tyr Thr Ser Leu Ile His Ser Leu Ile Glu Glu Ser Gln Asn
                645                 650                 655

Gln Gln Glu Lys Asn Glu Gln Glu Leu Leu Glu Leu Asp Lys Trp Ala
                660                 665                 670

Ser Leu Trp Asn Trp Phe Asn Ile Thr Asn Trp Leu Trp Tyr Ile Lys
                675                 680                 685

Ile Phe Ile Met Ile Val Gly Gly Leu Val Gly Leu Arg Ile Val Phe
                690                 695                 700

Ala Val Leu Ser Ile Val Asn Arg Val Arg Gln Gly Tyr Ser Pro Leu
705                 710                 715                 720

Ser Phe Gln Thr His Leu Pro Thr Pro Arg Gly Pro Asp Arg Pro Glu
                725                 730                 735

Gly Ile Glu Glu Glu Gly Gly Glu Arg Asp Arg Asp Arg Ser Ile Arg
                740                 745                 750

Leu Val Asn Gly Ser Leu Ala Leu Ile Trp Asp Asp Leu Arg Ser Leu
                755                 760                 765

Cys Leu Phe Ser Tyr His Arg Leu Arg Asp Leu Leu Leu Ile Val Thr
770                 775                 780

Arg Ile Val Glu Leu Leu Gly Arg Arg Gly Trp Glu Ala Leu Lys Tyr
785                 790                 795                 800

Trp Trp Asn Leu Leu Gln Tyr Trp Ser Gln Glu Leu Lys Asn Ser Ala
                805                 810                 815

Val Ser Leu Leu Asn Ala Thr Ala Ile Ala Val Ala Glu Gly Thr Asp
                820                 825                 830

Arg Val Ile Glu Val Val Gln Gly Ala Cys Arg Ala Ile Arg His Ile
                835                 840                 845

Pro Arg Arg Ile Arg Gln Gly Leu Glu Arg Ile Leu Leu
850                 855                 860
```

(2) INFORMATION FOR SEQ ID NO: 15:

```
       (i) SEQUENCE CHARACTERISTICS:
           (A) LENGTH: 21 amino acids
           (B) TYPE: amino acid
           (C) STRANDEDNESS: <Unknown>
           (D) TOPOLOGY: unknown (xi) SEQUENCE DESCRIPTION: SEQ ID NO: 15:

His Ser Leu Ile Glu Glu Ser Gln Asn Gln Gln Lys Asn Glu Gln
1               5                  10                  15

Glu Leu Leu Glu Leu
            20

(2) INFORMATION FOR SEQ ID NO: 16:

(i) SEQUENCE CHARACTERISTICS:
           (A) LENGTH: 7 amino acids
           (B) TYPE: amino acid
           (C) STRANDEDNESS: <Unknown>
           (D) TOPOLOGY: unknown (xi) SEQUENCE DESCRIPTION: SEQ ID NO: 16:

Gln Asn Gln Gln Glu Lys Asn
1               5

(2) INFORMATION FOR SEQ ID NO: 17:

(i) SEQUENCE CHARACTERISTICS:
           (A) LENGTH: 274 amino acids
           (B) TYPE: amino acid
           (C) STRANDEDNESS: <Unknown>
           (D) TOPOLOGY: unknown (xi) SEQUENCE DESCRIPTION: SEQ ID NO: 17:

Met Lys Thr Thr Leu Lys Met Thr Ala Leu Ala Ala Leu Ser Ala Phe
1               5                  10                  15

Val Leu Ala Gly Cys Gly Ser His Gln Met Lys Ser Glu Glu His Ala
            20                  25                  30

Asn Met Gln Leu Gln Gln Ala Val Leu Gly Leu Asn Trp Met Gln
            35                  40                  45

Asp Ser Gly Glu Tyr Lys Ala Leu Ala Tyr Gln Ala Tyr Asn Ala Ala
50                  55                  60

Lys Val Ala Phe Asp His Ala Lys Val Ala Lys Gly Lys Lys Lys Ala
65                  70                  75                  80

Val Val Ala Asp Leu Asp Glu Thr Met Leu Asp Asn Ser Pro Tyr Ala
                85                  90                  95

Gly Trp Gln Val Gln Asn Asn Lys Pro Phe Asp Gly Lys Asp Trp Thr
                100                 105                 110

Arg Trp Val Asp Ala Arg Gln Ser Arg Ala Val Pro Gly Ala Val Glu
            115                 120                 125

Phe Asn Asn Tyr Val Asn Ser His Asn Gly Lys Val Phe Tyr Val Thr
130                 135                 140

Asn Arg Lys Asp Ser Thr Glu Lys Ser Gly Thr Ile Asp Asp Met Lys
145                 150                 155                 160

Arg Leu Gly Phe Asn Gly Val Glu Glu Ser Ala Phe Tyr Leu Lys Lys
                165                 170                 175

Asp Lys Ser Ala Lys Ala Ala Arg Phe Ala Glu Ile Glu Lys Gln Gly
            180                 185                 190

Tyr Glu Ile Val Leu Tyr Val Gly Asp Asn Leu Asp Asp Phe Gly Asn
                195                 200                 205

Thr Val Tyr Gly Lys Leu Asn Ala Asp Arg Arg Ala Phe Val Asp Gln
            210                 215                 220
```

```
Asn Gln Gly Lys Phe Gly Lys Thr Phe Ile Met Leu Pro Asn Ala Asn
225                 230                 235                 240

Tyr Gly Gly Trp Glu Gly Gly Leu Ala Glu Gly Tyr Phe Lys Lys Asp
                245                 250                 255

Thr Gln Gly Gln Ile Lys Ala Arg Leu Asp Ala Val Gln Ala Trp Asp
            260                 265                 270

Gly Lys (2) INFORMATION FOR SEQ ID NO: 18:

(i) SEQUENCE CHARACTERISTICS:
           (A) LENGTH: 21 amino acids
           (B) TYPE: amino acid
           (C) STRANDEDNESS: <Unknown>
           (D) TOPOLOGY: unknown (xi) SEQUENCE DESCRIPTION: SEQ ID NO: 18:

Asn Ser Pro Tyr Ala Gly Trp Gln Val Gln Asn Asn Lys Pro Phe Asp
1               5                   10                  15

Gly Lys Asp Trp Thr
            20

(2) INFORMATION FOR SEQ ID NO: 19:

(i) SEQUENCE CHARACTERISTICS:
           (A) LENGTH: 7 amino acids
           (B) TYPE: amino acid
           (C) STRANDEDNESS: <Unknown>
           (D) TOPOLOGY: unknown (xi) SEQUENCE DESCRIPTION: SEQ ID NO: 19:

Gln Val Gln Asn Asn Lys Pro
1               5

(2) INFORMATION FOR SEQ ID NO: 20:

(i) SEQUENCE CHARACTERISTICS:
           (A) LENGTH: 170 amino acids
           (B) TYPE: amino acid
           (C) STRANDEDNESS: <Unknown>
           (D) TOPOLOGY: unknown (xi) SEQUENCE DESCRIPTION: SEQ ID NO: 20:

Ile Gln Pro Pro Lys Asn Leu Leu Phe Ser Ser Leu Leu Phe Ser Ser
1               5                   10                  15

Leu Leu Phe Ser Ser Ala Ala Gln Ala Ala Ser Glu Asp Arg Arg Ser
                20                  25                  30

Pro Tyr Tyr Val Gln Ala Asp Leu Ala Tyr Ala Ala Glu Arg Ile Thr
                35                  40                  45

His Asp Tyr Pro Gln Ala Thr Gly Ala Asn Asn Thr Ser Thr Val Ser
            50                  55                  60

Asp Tyr Phe Arg Asn Ile Arg Ala His Ser Ile His Pro Arg Val Ser
65                  70                  75                  80

Val Gly Tyr Asp Phe Gly Gly Trp Arg Ile Ala Ala Asp Tyr Ala Ser
                85                  90                  95

Tyr Arg Lys Trp Asn Asn Asn Lys Tyr Ser Val Asn Thr Lys Glu Leu
                100                 105                 110

Glu Asn Lys His Asn Asn Lys Lys Asp Leu Lys Thr Glu Asn Gln Glu
            115                 120                 125

Asn Gly Thr Phe His Ala Ala Ser Ser Leu Gly Leu Ser Ala Ile Tyr
        130                 135                 140
```

```
Asp Phe Lys Leu Lys Gly Lys Phe Lys Pro Tyr Ile Gly Ala Arg Val
145                 150                 155                 160

Ala Tyr Gly His Val Arg His Ser Ile Asp
                165                 170

(2) INFORMATION FOR SEQ ID NO: 21:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: unknown (xi) SEQUENCE DESCRIPTION: SEQ ID NO: 21:

Ile Gln Pro Pro Lys Asn Leu Leu Phe Ser Ser Leu Leu
1               5                   10

(2) INFORMATION FOR SEQ ID NO: 22:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: unknown (xi) SEQUENCE DESCRIPTION: SEQ ID NO: 22:

Ile Gln Pro Pro Lys Asn
1               5

(2) INFORMATION FOR SEQ ID NO: 23:

(i) SEQUENCE CHARACTERISTICS:
        (A) LENGTH: 695 amino acids
        (B) TYPE: amino acid
        (C) STRANDEDNESS: <Unknown>
        (D) TOPOLOGY: unknown (xi) SEQUENCE DESCRIPTION: SEQ ID NO: 23:

Lys Leu Met Ile Xaa Lys Phe Val Thr Lys Met Xaa Tyr Lys Thr Leu
1               5                   10                  15

Asp Lys Tyr Leu Arg Arg Arg Leu Ile Leu Asn Ile Ser Ile Val Xaa
                20                  25                  30

Lys Xaa Leu Ser Glu Lys Arg Xaa Ile Xaa Met Asn Lys Lys Lys Met
        35                  40                  45

Ile Leu Thr Ser Leu Ala Ser Val Ala Ile Leu Gly Ala Gly Phe Val
50                  55                  60

Ala Ser Gln Pro Thr Val Val Arg Ala Glu Glu Ser Pro Val Ala Ser
65                  70                  75                  80

Gln Ser Lys Ala Glu Lys Asp Tyr Asp Ala Ala Lys Lys Asp Ala Lys
                85                  90                  95

Asn Ala Lys Lys Ala Val Glu Asp Ala Gln Lys Ala Leu Asp Asp Ala
                100                 105                 110

Lys Ala Ala Gln Lys Lys Tyr Asp Glu Asp Gln Lys Lys Thr Glu Glu
                115                 120                 125

Lys Ala Ala Leu Glu Lys Ala Ala Ser Glu Glu Met Asp Lys Ala Val
                130                 135                 140

Ala Ala Val Gln Gln Ala Tyr Leu Ala Tyr Gln Gln Ala Thr Asp Lys
145                 150                 155                 160

Ala Ala Lys Asp Ala Ala Asp Lys Met Ile Asp Glu Ala Lys Lys Arg
                165                 170                 175

Glu Glu Glu Ala Lys Thr Lys Phe Asn Thr Val Arg Ala Met Val Val
```

-continued

```
            180                 185                 190
Pro Glu Pro Glu Gln Leu Ala Glu Thr Lys Lys Ser Glu Glu Ala
            195                 200                 205
Lys Gln Lys Ala Pro Glu Leu Thr Lys Lys Leu Glu Glu Ala Lys Ala
210                 215                 220
Lys Leu Glu Glu Ala Glu Lys Lys Ala Thr Glu Ala Lys Gln Lys Val
225                 230                 235                 240
Asp Ala Glu Glu Val Ala Pro Gln Ala Lys Ile Ala Glu Leu Glu Asn
                245                 250                 255
Gln Val His Arg Leu Glu Gln Glu Leu Lys Glu Ile Asp Glu Ser Glu
            260                 265                 270
Ser Glu Asp Tyr Ala Lys Glu Gly Phe Arg Ala Pro Leu Gln Ser Lys
            275                 280                 285
Leu Asp Ala Lys Lys Ala Lys Leu Ser Lys Leu Glu Glu Leu Ser Asp
            290                 295                 300
Lys Ile Asp Glu Leu Asp Ala Glu Ile Ala Lys Leu Glu Asp Gln Leu
305                 310                 315                 320
Lys Ala Ala Glu Glu Asn Asn Asn Val Glu Asp Tyr Phe Lys Glu Gly
                325                 330                 335
Leu Glu Lys Thr Ile Ala Ala Lys Lys Ala Glu Leu Glu Lys Thr Glu
            340                 345                 350
Ala Asp Leu Lys Lys Ala Val Asn Glu Pro Glu Lys Pro Ala Pro Ala
            355                 360                 365
Pro Glu Thr Pro Ala Pro Glu Ala Pro Ala Glu Gln Pro Lys Pro Ala
            370                 375                 380
Pro Ala Pro Gln Pro Ala Pro Ala Pro Lys Pro Glu Lys Pro Ala Glu
385                 390                 395                 400
Gln Pro Lys Pro Glu Lys Thr Asp Asp Gln Gln Ala Glu Glu Asp Tyr
                405                 410                 415
Ala Arg Arg Ser Glu Glu Glu Tyr Asn Arg Leu Thr Gln Gln Gln Pro
            420                 425                 430
Pro Lys Ala Glu Lys Pro Ala Pro Ala Pro Lys Thr Gly Trp Lys Gln
            435                 440                 445
Glu Asn Gly Met Trp Tyr Phe Tyr Asn Thr Asp Gly Ser Met Ala Thr
450                 455                 460
Gly Trp Leu Gln Asn Asn Gly Ser Trp Tyr Tyr Leu Asn Ser Asn Gly
465                 470                 475                 480
Ala Met Ala Thr Gly Trp Leu Gln Tyr Asn Gly Ser Trp Tyr Tyr Leu
                485                 490                 495
Asn Ala Asn Gly Ala Met Ala Thr Gly Trp Ala Lys Val Asn Gly Ser
            500                 505                 510
Trp Tyr Tyr Leu Asn Ala Asn Gly Ala Met Ala Thr Gly Trp Leu Gln
            515                 520                 525
Tyr Asn Gly Ser Trp Tyr Tyr Leu Asn Ala Asn Gly Ala Met Ala Thr
            530                 535                 540
Gly Trp Ala Lys Val Asn Gly Ser Trp Tyr Tyr Leu Asn Ala Asn Gly
545                 550                 555                 560
Ala Met Ala Thr Gly Trp Leu Gln Tyr Asn Gly Ser Trp Tyr Tyr Leu
                565                 570                 575
Asn Ala Asn Gly Ala Met Ala Thr Gly Trp Ala Lys Val Asn Gly Ser
            580                 585                 590
Trp Tyr Tyr Leu Asn Ala Asn Gly Ala Met Ala Thr Gly Trp Val Lys
            595                 600                 605
```

```
Asp Gly Asp Thr Trp Tyr Tyr Leu Glu Ala Ser Gly Ala Met Lys Ala
            610                 615                 620

Ser Gln Trp Phe Lys Val Ser Asp Lys Trp Tyr Tyr Val Asn Gly Leu
625                 630                 635                 640

Gly Ala Leu Ala Val Asn Thr Thr Val Asp Gly Tyr Lys Val Asn Ala
                645                 650                 655

Asn Gly Glu Trp Val Xaa Ala Asp Xaa Ile Lys Ala Cys Xaa Glu His
            660                 665                 670

Leu Thr Phe Xaa Phe Xaa Asn Lys Asp Lys Val Arg Leu Asn Arg Phe
            675                 680                 685

Met Phe Val Phe Phe Arg Tyr
            690                 695

(2) INFORMATION FOR SEQ ID NO: 24:

(i) SEQUENCE CHARACTERISTICS:
          (A) LENGTH: 21 amino acids
          (B) TYPE: amino acid
          (C) STRANDEDNESS: <Unknown>
          (D) TOPOLOGY: unknown (xi) SEQUENCE DESCRIPTION: SEQ ID NO: 24:

Glu Glu Tyr Asn Arg Leu Thr Gln Gln Gln Pro Pro Lys Ala Glu Lys
1               5                   10                  15

Pro Ala Pro Ala Pro
                20

(2) INFORMATION FOR SEQ ID NO: 25:

(i) SEQUENCE CHARACTERISTICS:
          (A) LENGTH: 7 amino acids
          (B) TYPE: amino acid
          (C) STRANDEDNESS: <Unknown>
          (D) TOPOLOGY: unknown (xi) SEQUENCE DESCRIPTION: SEQ ID NO: 25:

Gln Gln Gln Pro Pro Lys Ala
1               5

(2) INFORMATION FOR SEQ ID NO: 26:

(i) SEQUENCE CHARACTERISTICS:
          (A) LENGTH: 484 amino acids
          (B) TYPE: amino acid
          (C) STRANDEDNESS: <Unknown>
          (D) TOPOLOGY: unknown (xi) SEQUENCE DESCRIPTION: SEQ ID NO: 26:

Met Asn Met Lys Lys Ala Thr Ile Ala Ala Thr Ala Gly Ile Ala Val
1               5                   10                  15

Thr Ala Phe Arg Ala Pro Thr Ile Arg Ser Ala Ser Thr Val Val Val
                20                  25                  30

Glu Ala Gly Asp Thr Leu Trp Gly Ile Ala Gln Ser Lys Gly Thr Thr
            35                  40                  45

Val Asp Ala Ile Lys Lys Ala Asn Asn Leu Thr Thr Asp Lys Ile Val
        50                  55                  60

Pro Gly Gln Lys Leu Gln Val Asn Asn Glu Val Ala Ala Glu Lys
65                  70                  75                  80

Thr Glu Lys Ser Val Ser Ala Thr Trp Leu Asn Val Arg Ser Gly Ala
                85                  90                  95

Gly Val Asp Asn Ser Ile Ile Thr Ser Ile Lys Gly Gly Thr Lys Val
                100                 105                 110
```

```
Thr Val Glu Thr Thr Glu Ser Asn Gly Trp His Lys Ile Thr Tyr Asn
            115                 120                 125

Asp Gly Lys Thr Gly Phe Val Asn Gly Lys Tyr Leu Thr Asp Lys Ala
        130                 135                 140

Val Ser Thr Pro Val Ala Pro Thr Gln Glu Val Lys Lys Glu Thr Thr
145                 150                 155                 160

Thr Gln Gln Ala Ala Pro Ala Ala Glu Thr Lys Thr Glu Val Lys Gln
            165                 170                 175

Thr Thr Gln Ala Thr Thr Pro Ala Pro Lys Val Ala Glu Thr Lys Glu
            180                 185                 190

Thr Pro Val Val Asp Gln Asn Ala Thr Thr His Ala Val Lys Ser Gly
        195                 200                 205

Asp Thr Ile Trp Ala Leu Ser Val Lys Tyr Gly Val Ser Val Gln Asp
        210                 215                 220

Ile Met Ser Trp Asn Asn Leu Ser Ser Ser Ile Tyr Val Gly Gln
225                 230                 235                 240

Lys Leu Ala Ile Lys Gln Thr Ala Asn Thr Ala Thr Pro Lys Ala Glu
            245                 250                 255

Val Lys Thr Glu Ala Pro Ala Ala Glu Lys Gln Ala Ala Pro Val Val
            260                 265                 270

Lys Glu Asn Thr Asn Thr Asn Thr Ala Thr Glu Lys Lys Glu Thr
            275                 280                 285

Ala Thr Gln Gln Gln Thr Ala Pro Lys Ala Pro Thr Glu Ala Ala Lys
            290                 295                 300

Pro Ala Pro Ala Pro Ser Thr Asn Thr Asn Ala Asn Lys Thr Asn Thr
305                 310                 315                 320

Asn Thr Asn Thr Asn Thr Asn Thr Asn Thr Asn Thr Asn Thr Pro
            325                 330                 335

Ser Lys Asn Thr Asn Thr Asn Ser Asn Thr Asn Thr Asn Thr Asn Ser
            340                 345                 350

Asn Thr Asn Ala Asn Gln Gly Ser Ser Asn Asn Asn Ser Asn Ser Ser
            355                 360                 365

Ala Ser Ala Ile Ile Ala Glu Ala Gln Lys His Leu Gly Lys Ala Tyr
            370                 375                 380

Ser Trp Gly Gly Asn Gly Pro Thr Thr Phe Asp Cys Ser Gly Tyr Thr
385                 390                 395                 400

Lys Tyr Val Phe Ala Lys Ala Gly Ile Ser Leu Pro Arg Thr Ser Gly
            405                 410                 415

Ala Gln Tyr Ala Ser Thr Thr Arg Ile Ser Glu Ser Gln Ala Lys Pro
            420                 425                 430

Gly Asp Leu Val Phe Phe Asp Tyr Gly Ser Gly Ile Ser His Val Gly
            435                 440                 445

Ile Tyr Val Gly Asn Gly Gln Met Ile Asn Ala Gln Asp Asn Gly Val
        450                 455                 460

Lys Tyr Asp Asn Ile His Gly Ser Gly Trp Gly Lys Tyr Leu Val Gly
465                 470                 475                 480

Phe Gly Arg Val (2) INFORMATION FOR SEQ ID NO: 27:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown
```

(xi) SEQUENCE DESCRIPTION: SEQ ID NO: 27:

Ala Val Ser Thr Pro Val Ala Pro Thr Gln Glu Val Lys Lys Glu Thr
1               5                   10                  15

Thr Thr Gln Gln Ala
            20

(2) INFORMATION FOR SEQ ID NO: 28:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 28:

Pro Thr Gln Glu Val Lys Lys
1               5

(2) INFORMATION FOR SEQ ID NO: 29:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (xi) SEQUENCE DESCRIPTION: SEQ ID NO: 29:

Val Lys Gln Thr Thr Gln Ala Thr Thr Pro Ala Pro Lys Val Ala Glu
1               5                   10                  15

Thr Lys Glu Thr Pro
            20

(2) INFORMATION FOR SEQ ID NO: 30:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 30:

Thr Thr Pro Ala Pro Lys Val
1               5

(2) INFORMATION FOR SEQ ID NO: 31:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (xi) SEQUENCE DESCRIPTION: SEQ ID NO: 31:

Leu Ala Ile Lys Gln Thr Ala Asn Thr Ala Thr Pro Lys Ala Glu Val
1               5                   10                  15

Lys Thr Glu Ala Pro
            20

(2) INFORMATION FOR SEQ ID NO: 32:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 32:

Asn Thr Ala Thr Pro Lys Ala
1               5

(2) INFORMATION FOR SEQ ID NO: 33:

(i) SEQUENCE CHARACTERISTICS:
        (A) LENGTH: 21 amino acids
        (B) TYPE: amino acid
        (C) STRANDEDNESS: <Unknown>
        (D) TOPOLOGY: unknown (xi) SEQUENCE DESCRIPTION: SEQ ID NO: 33:

Lys Lys Glu Thr Ala Thr Gln Gln Gln Thr Ala Pro Lys Ala Pro Thr
1               5                   10                  15

Glu Ala Ala Lys Pro
            20

(2) INFORMATION FOR SEQ ID NO: 34:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 34:

Gln Gln Thr Ala Pro Lys Ala
1               5

(2) INFORMATION FOR SEQ ID NO: 35:

(i) SEQUENCE CHARACTERISTICS:
        (A) LENGTH: 99 amino acids
        (B) TYPE: amino acid
        (C) STRANDEDNESS: <Unknown>
        (D) TOPOLOGY: unknown (xi) SEQUENCE DESCRIPTION: SEQ ID NO: 35:

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr (2) INFORMATION FOR SEQ ID NO: 36:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (xi) SEQUENCE DESCRIPTION: SEQ ID NO: 36:

Ser Met Asp His Leu Asp Lys Gln Thr Gln Thr Pro Lys Thr
1               5                   10

(2) INFORMATION FOR SEQ ID NO: 37:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 37:

Gln Thr Gln Thr Pro Lys Thr
1               5

(2) INFORMATION FOR SEQ ID NO: 38:

(i) SEQUENCE CHARACTERISTICS:
        (A) LENGTH: 67 amino acids
        (B) TYPE: amino acid
        (C) STRANDEDNESS: <Unknown>
        (D) TOPOLOGY: unknown (xi) SEQUENCE DESCRIPTION: SEQ ID NO: 38:

Lys Ser Thr Thr Cys Cys Tyr Arg Phe Ile Asn Lys Lys Ile Pro Lys
1               5                   10                  15

Gln Arg Leu Glu Ser Tyr Arg Arg Thr Thr Ser Ser His Cys Pro Arg
            20                  25                  30

Glu Ala Val Ile Phe Lys Asp Lys Glu Ile Cys Ala Asp Pro Thr Gln
            35                  40                  45

Lys Trp Val Gln Asp Phe Met Lys His Leu Asp Lys Lys Thr Gln Thr
    50                  55                  60

Pro Lys Leu
65

(2) INFORMATION FOR SEQ ID NO: 39:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: unknown (xi) SEQUENCE DESCRIPTION: SEQ ID NO: 39:

Phe Met Lys His Leu Asp Lys Lys Thr Gln Thr Pro Lys Leu
1               5                   10

(2) INFORMATION FOR SEQ ID NO: 40:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 40:

Lys Thr Gln Thr Pro Lys Leu
1               5

(2) INFORMATION FOR SEQ ID NO: 41:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 41:

-continued

```
Gln Gln Gln Gln Pro Ala Ala
1               5
```

(2) INFORMATION FOR SEQ ID NO: 42:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 42:

```
Gln Thr Ile Pro Ile Lys Thr
1               5
```

(2) INFORMATION FOR SEQ ID NO: 43:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 43:

```
Gln Ala Gln Thr Asn Ala Arg
1               5
```

(2) INFORMATION FOR SEQ ID NO: 44:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 44:

```
Tyr Thr Thr Val Pro Lys Tyr
1               5
```

(2) INFORMATION FOR SEQ ID NO: 45:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 45:

```
Leu Thr Gly Thr Ser Lys Ser
1               5
```

(2) INFORMATION FOR SEQ ID NO: 46:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 46:

```
Leu Gln Gln Thr Ala Gly Leu
1               5
```

(2) INFORMATION FOR SEQ ID NO: 47:

(i) SEQUENCE CHARACTERISTICS:
        (A) LENGTH: 7 amino acids
        (B) TYPE: amino acid
        (C) STRANDEDNESS: <Unknown>

(D) TOPOLOGY: unknown (xi) SEQUENCE DESCRIPTION: SEQ ID NO: 47:

Gln Thr Gln Phe Ser Arg Thr
1               5

(2) INFORMATION FOR SEQ ID NO: 48:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 48:

Gln Thr Gln Gly Pro Tyr Ser
1               5

(2) INFORMATION FOR SEQ ID NO: 49:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 49:

Pro Pro Gln Thr Pro Pro Thr
1               5

(2) INFORMATION FOR SEQ ID NO: 50:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 50:

Gln Ala Gln Pro Asn Lys Ser
1               5

(2) INFORMATION FOR SEQ ID NO: 51:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 51:

Gln Thr Gln Pro Ser Lys Pro
1               5

(2) INFORMATION FOR SEQ ID NO: 52:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 52:

Gln Ser Gln Thr Pro Leu Asn
1               5

(2) INFORMATION FOR SEQ ID NO: 53:

```
    (i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 53:

Glu Thr Ser Val Pro Lys Cys
1               5

(2) INFORMATION FOR SEQ ID NO: 54:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 54:

Gln Thr Arg Asp Thr Lys Glu
1               5

(2) INFORMATION FOR SEQ ID NO: 55:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 55:

Gln Val Ser Thr Gln Lys Thr
1               5

(2) INFORMATION FOR SEQ ID NO: 56:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 56:

Trp Thr Lys Asp Pro Lys Asn
1               5

(2) INFORMATION FOR SEQ ID NO: 57:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 57:

Pro Asn Gln Lys Pro Lys Val
1               5

(2) INFORMATION FOR SEQ ID NO: 58:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 58:

Gln Ser Leu Thr Thr Lys Pro
1               5
```

(2) INFORMATION FOR SEQ ID NO: 59:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 59:

Gln Thr Gln Thr Asp Pro Ile
1               5

(2) INFORMATION FOR SEQ ID NO: 60:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 60:

Gln Leu Gln Asp Gly Lys Thr
1               5

(2) INFORMATION FOR SEQ ID NO: 61:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 61:

Gln Glu Glu Gly Pro Lys Ile
1               5

(2) INFORMATION FOR SEQ ID NO: 62:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 62:

Asn Thr Asn Thr Ser Lys Ser
1               5

(2) INFORMATION FOR SEQ ID NO: 63:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown (xi) SEQUENCE DESCRIPTION: SEQ ID NO: 63:

Ala Thr Ala Ala Pro Lys Thr
1               5

(2) INFORMATION FOR SEQ ID NO: 64:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: unknown

```
        (xi) SEQUENCE DESCRIPTION: SEQ ID NO: 64:

Gln Gly Glu Thr His Lys Ala
1               5

(2) INFORMATION FOR SEQ ID NO: 65:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: unknown (xi) SEQUENCE DESCRIPTION: SEQ ID NO: 65:

Gln Gln Pro Ala Pro Ala Thr
1               5

(2) INFORMATION FOR SEQ ID NO: 66:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: unknown (xi) SEQUENCE DESCRIPTION: SEQ ID NO: 66:

Ser Thr Gln Ser Ala Lys Asn
1               5

(2) INFORMATION FOR SEQ ID NO: 67:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: unknown (xi) SEQUENCE DESCRIPTION: SEQ ID NO: 67:

Gln Thr Thr Thr Pro Thr Ala
1               5

(2) INFORMATION FOR SEQ ID NO: 68:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: unknown (xi) SEQUENCE DESCRIPTION: SEQ ID NO: 68:

Gln Thr Gln Thr Pro Val Asn
1               5

(2) INFORMATION FOR SEQ ID NO: 69:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: unknown (xi) SEQUENCE DESCRIPTION: SEQ ID NO: 69:

Gln Pro Ala Ser Ser Lys Thr
1               5

(2) INFORMATION FOR SEQ ID NO: 70:

(i) SEQUENCE CHARACTERISTICS:
            (A) LENGTH: 7 amino acids
```

```
            (B) TYPE: amino acid
            (C) STRANDEDNESS: <Unknown>
            (D) TOPOLOGY: unknown (xi) SEQUENCE DESCRIPTION: SEQ ID NO: 70:

Arg Pro Asp Thr Pro Arg Thr
1               5

(2) INFORMATION FOR SEQ ID NO: 71:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: unknown (xi) SEQUENCE DESCRIPTION: SEQ ID NO: 71:

Val Thr His Pro Pro Lys Val
1               5

(2) INFORMATION FOR SEQ ID NO: 72:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: unknown (xi) SEQUENCE DESCRIPTION: SEQ ID NO: 72:

Ile Gln Pro Pro Lys Asn
1               5

(2) INFORMATION FOR SEQ ID NO: 73:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: unknown (xi) SEQUENCE DESCRIPTION: SEQ ID NO: 73:

Ile Gln Pro Pro Lys Thr
1               5

(2) INFORMATION FOR SEQ ID NO: 74:

(i) SEQUENCE CHARACTERISTICS:
            (A) LENGTH: 7 amino acids
            (B) TYPE: amino acid
            (C) STRANDEDNESS: <Unknown>
            (D) TOPOLOGY: unknown (xi) SEQUENCE DESCRIPTION: SEQ ID NO: 74:

Gln Thr Gln Val Ala Ala Thr
1               5

(2) INFORMATION FOR SEQ ID NO: 75:

(i) SEQUENCE CHARACTERISTICS:
            (A) LENGTH: 39 amino acids
            (B) TYPE: amino acid
            (C) STRANDEDNESS: <Unknown>
            (D) TOPOLOGY: unknown (xi) SEQUENCE DESCRIPTION: SEQ ID NO: 75:

Lys Glu Ala Val Val Phe Val Thr Lys Leu Lys Arg Glu Val Cys Ala
1               5                   10                  15

Asp Pro Lys Lys Glu Trp Val Gln Thr Tyr Ile Lys Asn Leu Asp Arg
```

```
                  20                  25                  30
Gln Gln Gln Pro Pro Lys Ala
            35
```

METHODS TO CLEAR MENINGITIS CAUSING AGENTS USING ANTIBODIES TO PEPTIDES REPRESENTING EPITOPIC SITES FOR BACTERIAL AND VIRAL MENINGITIS CAUSING AGENTS

CROSS REFERENCE TO RELATED APPLICATIONS

This is a continuation application of Ser. No. 08/988,444 filed Dec. 11, 1997, now abandoned, which is a continuation application of Ser. No. 08/486,050 filed Jun. 7, 1995, now abandoned, which is a continuation in part of application Ser. No. 08/127,499 filed Sep. 28, 1993, now U.S. Pat. No. 5,510,264.

BACKGROUND OF THE INVENTION

1. Field of the Invention

The present invention relates to polypeptides comprising amino acid sequences corresponding to a chemokine and a hapten that are useful as vaccines. The polypeptides of the present invention may include a hapten that is a Meningitis Related Homologous Antigenic 10 Sequences (MRHAS) from a bacterial or viral agent known to cause meningitis. These peptides induce protective immunity in a host susceptible to meningitis. The present invention also relates to materials useful in the diagnosis of diseases, including meningitis, by providing monoclonal antibodies, peptides, and mixtures and combinations thereof, that are useful in detection of disease-causing organisms.

2. Meningitis

The term "meningitis" is a general one, referring to the inflammatory response to infection of the meninges and the cerebrospinal fluid (CSF). See Roos, "Chapter 16", in Scheld, et al., eds., 1991, Infections of the Central Nervous System: 335-403.

The fact that the inflammatory response occurs in the proximity of the brain and in the space limited by a rigid cranium, makes these infections serious and life threatening. Most patients exhibit nonspecific clinical signs and symptoms such as fever, irritability, altered mental status usually accompanied by vomiting and loss of appetite. In children one year of age and older, photophobia and headache are common complaints. Specific clinical signs indicative of meningitis are neck rigidity and pain on neck flexion. Brudzinski's sign (neck flexion producing knee and hip flexion) and Kernig's sign (difficulty and pain in raising extended leg) are other Useful clinical signs.

In infants less than 6 months old, early diagnosis of meningitis is difficult because signs of meningitis are not prominent and neck rigidity is often absent. Such patients commonly exhibit fever, respiratory distress, other signs of sepsis, and convulsions. Bulging anterior fontanelle due to increased intracranial pressure may be the only specific sign.

Petechiae (or rash) is, most commonly present in meningococcal infections. In severe meningococcal infections, bacteremia, petechiae and shock may develop with alarming rapidity. Convulsions at some point in the illness occur in about 30% of the cases. This number is 20 often higher in neonates and infants under one year of age. Other acute complications include septic shock, disseminated intravascular coagulation, syndrome of inappropriate antidiuretic hormone, increased intracranial pressure, and diabetes ins ipidus. 25 Convulsions and coma appearing with 24 hours accompanied by high fever indicates serious infection. Stutman & Marks, 1987, Clin. Ped., 26:432-438.

A diverse array of both bacteria and viruses cause meningitis, the infectivity of which is dependent on a complex array of factors, including virulence of the organisms, the carrier state, and the host's humoral immune response.

Viral Causes of Meningitis

Viruses generally cause milder forms of meningitis 35 (e.g. meningomyelitis and aseptic meningitis) with a short clinical course and reduced mortality. Agents most commonly associated are coxsackievirus A (types 2,4,7,9,10), B (types 1-6), polio virus, echoviruses (types 1-34, except, 12, 24, 26, 29, 32-34), enteroviruses (types 70, 71), human immunodeficiency virus-1 (HIV-1), and rubella virus (RV). See Melnick, "Chapter 33" and Cooper, "Chapter 42" in Fields, et al., eds., 1985 5 Virology: 739-794 and 1005-1032, respectively; and Rotbart, "Chapter 3", in Scheld et al., 1991, infra: 19-33.

Rubella is possibly the most common cause of viral meningitis. Rubella is a highly contagious disease, usually associated with childhood, and is characterized by a general rash and a mild fever. Sub-clinical infections are also common. Its clinical aspects have been confused with measles, which it closely resembles. The infection of a pregnant woman poses the greatest risk when infection of the fetus can lead to spontaneous abortion or an array of abnormalities called the Congenital Rubella Syndrome in the newborn. Damage most frequently involves cardiac abnormalities, deafness, cataracts, blindness and Central Nervous System (CNS) 20 disorders including microencephaly.

The rubella virion is a spherical, enveloped virus, approximately 60 rim in diameter, and is a member of the Togaviridae. The RV genome is a 10 Kb plus single-stranded RNA. The outer envelope is comprised of 25 lipoproteins derived from the infected host cell, and it appears to have two viral encoded glycoproteins, E1 (58 Kd) and E2 (42-47 Kd), responsible for the hemagglutination activity of the virus. Its core protein is a non-glycosylated nucleocapsid protein with an 30 approximate weight of 33 Kd. It appears that the core; E1, and E2 are all derived from the same parent protein or structural polyprotein. See Clark et al., 1987, Nucl. Acids Res., 15:3041-3057; Dominguez, et al., 1990, Virology, 177: 225-238. Three strains of wild type RV 35 (M33, Therien, Judith) and a vaccine strain (TPV77) of RV have been identified and sequenced (Zheng et al., 1988, Arch, Viral., 98:189-197). Between these different wild type strains, there exists minor variations in the amino acid sequence of the structural polyprotein.

The detection of RV in diagnosis has in the past proven difficult, largely because the virus grows to low titers in the tissue cultures and is highly labile, making it technically difficult to isolate and purify (Ho-Terry et al., 1986, Arch. Virol., 87:219-228).

The detection of RV in the CNS presents additional technical problems. It has been known since 1941 that the RV can infect cells of the CNS (Gregg, 1941, Trans. Ophthalmol. Soc. Aust., 3:3546). However, it has proven difficult to reliably demonstrate the presence of the RV in infected brain tissue. Persistent infection of the CNS has been well documented in the congenital rubella syndrome (Desmond et al., 1967, J. Pediat., 7:311-331), and in the neuropathology of progressive rubella panencephalitis of late onset occurs where the virus has been isolated from brain biopsy material (Townsend et al., 1975, N. Engl. J. Med., 292:990-993; Cremer et al., 1979, J. Gen. Virol., 29:143-153). Less commonly documented are the wide range of neuropathies known to follow exposure to V. These include encephalitis, meningomyelitis, and bilateral optic neuritis (Connolly et al., 1975, Brain, 98:583-594). Moreover, the report of a diffuse myelitis following RV in cells of the nervous system requires further investigation (Holt et al. 1975, Brit. Med. J., 7:1037-1038).

RV-directed polypeptide synthesis in normal rat glial cells in continuous tissue culture has been studied •(Singh & Van Alstyne, 1978, Brain Res., 155:418-421). Unlike a productive rubella virus infection in permissive murine L (muscle) cells, infection of normal glial cells resulted in no detectable progeny virions in tissue culture supernatants and no detectable rubella 33 Kd core protein in infected cell lysates (Pope and Van Alstyne, 1981, Virology, 124:173-180). Furthermore, exposure of infected glial cells to dibutyryl cyclic adenine monophosphate reversed the restriction, resulting in the appearance of the 33 Kd rubella nucleocapsid protein in infected cell lysates and the appearance of mature progeny virions in tissue culture supernatants (Van Alstyne and Paty, 1983, Virology, 124:173-180).

Early diagnostic tests were based on the hemagglutinating properties of its external glycoproteins. Commonly, the hemagglutination inhibition assays relied on the presence of antibodies to the RV hemagglutinin (HA) in the serum samples to inhibit the viral-mediated hemagglutination of chick red blood cells (Herrmann, "Rubella Virus", 1979, in Diagnostic Procedures For Viral, Rickettsial And Chlamylial Infections, 725-766). The presence of high inhibition, indicated the indirect measurement of antibodies to the HA protein, and thereby, a recent rubella infection.

More recent tests employ enzyme-labelled antibodies in the enzyme-linked-immunosorbent assays (ELISA) (Voller & Biowell, 1975, Br. J. Exp. Pathol., 56:338-339), These assays are also indirect tests to measure the amount of circulating antibody to RV as an indication of infection. Indirect ELISA tests for RV employ bound viral antigens on a plastic microwells and the presence of bound antibodies linked to enzymes such as horseradish peroxidase.

There are several problems with the use of the indirect RV ELISA kits. These relate to low antibody titers observed with RV infection, the need for elaborate "cut-off" value calculations to eliminate background binding, the limited use of the test in the detection of low levels of specific viral antigens present in chronic CNS infection, and the tedious and time consuming nature of the test performance.

Furthermore, a live, attenuated rubella vaccine has been developed (Parkman et al., 1966, An. Engl. J. Med., 275:569-574). This vaccine is immunogenic in at least 95% of the recipients, and does confer protection against reinfection, in spite of the fact that it induces antibody levels which are significantly lower than those generated by wild type virus infection. However, a serious drawback associated with the administration of the attenuated vaccine is the significant proportion of adult females that go on to develop rubella-associated arthritis. Furthermore, recently immunized individuals still harbour infectious virus and are therefore infectious, proving dangerous to pregnant women with whom they may be in contact.

Another virus responsible for meningitis is the Human Immunodeficiency Virus-1 (HIV-1). HIV-1 is a human retrovirus which has been identified as the etiological agent of AIDS, an infectious and fatal disease transmitted through intimate sexual contact and exposure to contaminated blood or blood products. HIV-1 is related to the lentiviruses on the basis of its biological and in vitro characteristics, morphology and nucleotide sequences. It is also referred to as Human T cell Lymphotrophic Virus, type III, Lymphadenopathy Associated Virus, and AIDS Associated Retrovirus (Gallo, et al., 1984, Science, 224:500-503; Sarngadharan, et al., 1984, Science, 224:506-508; Barre-Sinoussi, et al., 1983, Science, 220:868-871; Levy, 1984, Science, 225:840-842; Gonda et al., 1985, Science, 227:177-179; Stephan, et al., 1986, Science, 231:589-594). Much interest has been focused on the effect of the long term, persistent infection of the immune system, by HIV-1. Recent information indicates that the virus moves from blood to the lymph nodes and thymus where it remains active, culminating in viremia, a precipitous drop in the CD4+ T-cell count, and one or more of the several symptoms known as AIDS.

However, primary HIV-1 infection itself results in an immediate set of defined clinical features. Commonly, an acute febrile illness resembling influenza or mononucleosis is noted. In addition, lymphocytic meningitis may accompany the febrile illness and the patient may then be presented with headache, stiff neck and photophobia, as well as rigors, arthralgias and myalgias, truncal maculopapular rash, urticaria, abdominal cramps and diarrhea (Ho, 1985, Ann. Internal Medicine, 103:880-883).

While some patients remain asymptomatic for up to 3 months preceding their seroconversion, indicating that HIV-1 infection may be subclinical, primary infection should be included in the differential diagnosis of prolonged febrile illnesses in persons at risk for AIDS. The presence of a maculopapular or urticarial rash, or lymphocytic meningitis is compatible with this diagnosis. Hence, early recognition of the varied syndromes associated with this virus might permit effective treatment before immunologic abnormalities become established.

Currently, one of the most commonly used direct tests for HIV-1 infection employs the following approaches: (i) direct culturing of virus from infected blood or blood cells and subsequent in vitro, propagation of the virus in lymphocyte cultures; (ii) measuring reverse transcriptase levels; (iii) immunocytochemical staining of viral proteins; (iv) electron microscopy; (v) hybridization of nucleic acid probes; and measuring HIV-1 antigens with enzyme immunoassays (Goudsmit et al., 1986, Brit. Med. 2993:1459-1462; Caruso et al., 1987, J. Virol. Methods, 17:199-210).

HIV-1 appears to have at least three core proteins (p17, p24, and p15) that are derived from a core polyprotein called gag polyprotein. See Muesing, et al., 1985, Nature, 313:450-458. The gag polyprotein in the LV isolate of HIV-1 is 478 amino acids long and the three mature core proteins appear to be derived as p17 from amino acid sequence numbers 1-132, p24 from amino acid 30 sequence numbers 133-391, and p15 from amino acid sequence numbers 392-478 (Muesing, infra). Moreover, it appears that the HIV-1 (LAV-1a isolate) also has at least one capsid transmembrane glycoprotein derived from a 861-amino acid long Envelope Polyprotein (Wain-Hobson, et al., 1985, Cell, 40:9-17).

Enzyme immunoassays have clearly shown the diagnostic importance of the presence of the p24 core protein. A correlation has been established between viremia, the decline of antibodies to p24, and the progression of symptoms from the asymptomatic seropositivity to fully expressed AIDS (Lange et al., 1986, Brit. Med. J., 293:1459-1462; Paul et al., 1987, J. Med. Virol., 22:357-363; Forster et al., 1987 AIDS, 1:235-240). A, decline in the p24 level has also been observed to occur inpatients treated with AZT (Chaisson et al., 1986, New Eng. J. Med., 315:1610-1611).

Assays for the direct detection of p24 are currently on the market (Allain, infra; Forster, infra). These assays use the same sandwich format in which serum samples are incubated with bound and enzyme-labelled anti-p24-antibodies to form an antibody/p24-antigen-antibody sandwich. Antigen levels of approximately 50 picograms/ml can be detected, when the antigen concentration is read from a, standard curve constructed with a set of p24 standards of known concentrations.

The tests are tedious and time consuming to perform, require dilutions of patients' sera, and do not provide information regarding the comparisons of rising antigen and concomitant declining antibody levels necessary to evaluate laboratory findings.

There are significant difficulties inherent in designing a vaccine which will confer protection against HIV-1. The vaccine must differentiate between HIV-1 and closely-related virus, HIV-2. The rapid rate of HIV-1 mutation requires that the antigen(s) be highly conserved. Moreover, the HIV-1 infection of a small subset of T cells requires the killing of an integral part of the immune cell network, with unknown consequences, to completely eradicate the virus. In addition, vaccinated antigens could enter lymph nodes and stimulate B cells to produce cytokines that in turn stimulate HIV-1 infection of T cells, and thereby having a reverse effect, causing a more rapid onset of AIDS.

Peptides from gp120, gp160, gp41, gp120 +gp41, p17 and p14 are currently being employed for vaccine production by several companies and universities (Spalding, 1992, Biotech., 10:24-29.) However, these peptides are being tested for their ability to solely induce B cells to produce neutralizing antibody.

Bacterial Causes of Meningitis

Bacteria are the other major cause of meningitis. Approximately 70% of all cases of bacterial meningitis. occur in children under the age of 5 years and three bacterial species cause 84% of all meningitis cases reported in the United States including Haemophilus Influenza type B, *Streptococcus pneumoniae* and *Neisseria* 10 *meningitidis*. Less prevalent bacterial species include *Pseudomonas aerugenosa*, Staphylococci, *Mycobacteria* and *Listeria* species. All strains of *Haemophilus influenzae* are divided into two groups; typeable strains which commonly have a capsule, and nontypeable strains which do not. Typing of the encapsulated strains is accomplished by serological techniques, using reference antisera. Types a to f have been identified in this way. Those strains which fail to react with any of the reference antisera are classified its nontypeable.

The most frequent cause of neonatal meningitis and other invasive infections in the United States is the encapsulated H. influenzas type b (Hib) (Fraser et al., 1974, Am. J. Epidemiol., 100:29-34). While the major 25 incidence of childhood meningitis occurs between the ages of one and five years, 60% of the meningitis cases due to Hib occur in children under the age of two years.

The nontypeable *H. influenzae* are known to cause meningitis, pneumonia, bacteremia, postpartum sepsis, and acute febrile tracheobronchitis in adults (Murphy et al., 1985, J. Infect. Diseases, 152:1300-1307). About 20 to 40% of all cases of otitis media are caused by this *H. influenzae*, which is a frequent etiologic agent of otitis media in children and young adults. Since infection confers no long lasting immunity, repeated infections of the same organism is frequently observed. These chronic otitis media infections are treated by administration of antibiotics, and drainage of the inner ear, where such a procedure is deemed necessary. *H. influenzae* strains have also been implicated as a primary cause of sinusitis (Chemy & Dudley, 1981, in Feigin & Chemy eds., Textbook of Pediatric infectious Diseases:103-105). Nontypeable H. influenzas are also known to cause neonatal sepsis.

A vaccine is currently available for protection against typeable H. influenzas, and employs the capsular polysaccharide antigen of Hib, polyribosyl ribitol phosphate (Smith et al., 1973, Pediatrics, 52:637-644; Anderson et al., 1972, J. Clin. mv., 51:31-88). However, Anti-PRP antibody is not effective in conferring protection.against non-typeable *H. influenzae* infection. Thus, all available vaccines against *H. influenzae* are all directed against Hib, and all elicit anti-PRP antibody to confer protection. Since the non-typeable *H. influenzae* lack the PRP capsule, no vaccine is efficacious against this group.

*H. influenzae* exhibits an outer membrane lipoprotein referred to as p4 (Green, et al., 1992, EMBL Bank). The p4 protein appears to be derived from the Lipoprotein E Precursor, the precursor protein being 274 amino acids in length.

*Streptococcus pneumoniae* is the leading cause of community-acquired bacterial pneumonia (pneumococcal diseases), with approximately 500,000 cases a year reported in the United States. Bacterial pneumonia is most prevalent among the very young, the elderly and immuno-compromised persons. In infants and children, pneumococci are the most common bacterial cause of pneumonia, otitis media and bacteremia and a less common cause of meningitis (causing 20-25% of reported cases).

Pneumococci are carried in the respiratory tract of a significant number of healthy individuals. But, in spite of the high carriage rate, its presence does not necessarily imply infection. However, if one of the highly pathogenic pneumococcal types, such as *S. pneumoniae*, is isolated from rusty-colored sputum (also containing a large number of polymorphonuclear leucocytes), body fluids, blood cultures, or specimens collected via transtracheal or lung puncture from the lower respiratory tract, its detection is usually significant.

*S. pneumoniae* is a gram positive bacteria. Proteins located on the cell surface of many gram positive Bacteria are frequently involved in virulence and host immunity and have, in the past, been used in typing these bacteria and in immunoprotection studies. There are a large number of *S. pneumoniae* strains, classified into serotypes based on their surface carbohydrate structures. There are also many cell surface proteins associated with *S. pneumoniae*. Surface proteins that exhibit antigenic variation (by antigenic shift or drift) make the identification of a common but exclusive cell surface antigen difficult and may provide the organism with an additional mechanism for evading the host immune response.

Detection of this bacteria at an early stage is essential to facilitate treatment of the infection. Thus, it is important to be able to quickly identify whether *S. pneumoniae* is present in a patient and to be able to follow the effect of antibiotic treatment on the bacteria. As available immunoassay for *S. pneumoniae* antigen detection are deficient for lack of specificity and/or sensitivity, there remains the need for an improved method of such detection.

Monoclonal antibody (Mab) technology has recently provided researchers with tools to reproducibly and accurately analyze the cell surface components of *S. pneumoniae*. Hence *S. pneumoniae* proteins are of interest to epidemiologists as they may provide a method of detection as well as for vaccines against the bacteria. One such cell surface protein is *Streptococcus pneumoniae* pneumonococcal surface protein A (pspA) Yother, 1992, J. Bacteriol., 174:601-609). The complete sequence of this protein is known.

It is known that one such pneumonococcal vaccine has been developed which incorporates the capsular polysaccharide antigens of 23 prevalent serotypes of pneumococci. These serotypes are responsible for 87% of pneumococcal disease in the United States. This second generation vaccine replaced a 14-valent polysaccharide vaccine available since 1977. However, the U.S. Department of Health and Human Services has stated that a more immunogenic pneumococcal vaccine is needed,. particularly for children younger than 2 years of age. This necessity exists because the 23-valent vaccine is poorly immunogenic in this age group. Consequently, the use of the vaccine is not recommended in children with recurrent• upper respiratory diseases, such as otitis media and sinusitis. Furthermore, the 23-valent vaccine is only 44-61% efficacious when administered to persons over 65 years old, and revaccination is not advised. Thus, there remains a clear need for an improved pneumococcal vaccine.

Neisseria meningitis is one of the leading causes of community-acquired bacterial meningitis, causing 10.3% of cases in the United States between 1978-1981 (Tunkel et al., 1990 Annals of Internal Medicine, 112:610-623). Meningococcal meningitis is most prevalent among infants between 6-12 months and adolescents (Larter & Paster, 1992, Am. J. Med.-Infectious Disease Symposium: 120-123). In addition to meningococcaemia, other less commonly associated diseases such as conjunctivitis, sinusitis, endocarditis, and primary pneumonia can occur (Duerden, 1988, J. Med. Microbiol., 21:161-1137). *N. meningitidis* bacterium are carried in the nasopharynx of 10-15% of healthy individuals. In spite of the high carriage rate, its presence does not necessarily imply infection. However, isolation of *N. meningitidis*; from cerebral spinal fluid or blood culture is significant (Stutnan, infra; Mendelson & Dascal, 1992, Can. J. of Diag., 9:47-57; Martin, 1983, Am. J. Med., 120-123).

*N. meningitidis* is a gram negative bacteria. Proteins located on the cell surface of many gram negative bacteria have, in the past, been used in typing and immunoprotective studies. there are a large number of *N. meningitidis* strains and there are many cell surface proteins associated with *N. meningitidis*. This has made identification of a common but exclusive cell surface antigen difficult.

Detection of this bacteria at an early stage is essential to facilitate treatment of the infection (Stutman, infra). Thus, it is important to possess the ability to identify whether *N. meningitidis* is present in a patient and to follow the effect of antibiotic treatment on the bacteria. As available immunoassay for *N. meningitidis* antigen detection have shown lack of specificity and/or sensitivity, there remains the need for an improved method of such detection.

As Mab technology has recently provided researchers with tools to accurately, analyze the cell surface components of this bacteria, *N. meningitidis* proteins are of interest to the epidemiologists as they may provide for a new method of detection as well as a vaccines against it. One such cell surface protein is the Opacity-Related Protein POPM3 (Stern, 1987, Mol. Microbiol., 1; 5-12). The complete sequence of this 170 amino acid protein is known.

Most meningococcal vaccines have been developed using capsular polysaccharides. One particularly quadravalent vaccine incorporates polyssacharide antigens of serogroups A, C, W and Y, meningococci. However, these serogroups are responsible for less than 49% of meningococcal disease in the United States. No capsular polyssachariade vaccine is available for serogroup B *N. meningitidis*, which is the most prevalent serogroup, since it is poorly immunogenic. Moreover, polysaccharide vaccines are poorly immunogenic in infants because they are T. lymphocyte independent antigens which are inefficient at inducing an immunologic memory. Furthermore, no cross protection between serogroups occurs. Thus, there remains the need for an improved meningococcal vaccine.

There remains a need for at least two products relating to *N. meningitidis*. The first being a rapid, specific, and sensitive diagnostic test for all strains of *N. meningitidis*, that does not give false positive results. What is optimally desired is an antibody that will recognize a cell surface antigen that is universally present in most, if not all, strains of *N. meningitidis*, and, at the same time does not recognize other non-meningitidis causing organisms or material which may be found in conjunction with *N. meningitidis*. Secondly, it is desirous that the Mab and said protein be used in research towards development of an improved vaccine.

In addition to the three major causes of bacterial meningitis, there are other bacterial agents responsible for the disease. One such agent is *L. monocytogenes*, a motile, gram positive, rod-shaped microorganism belonging to the genus *Listeria*. This, genus is widely distributed in nature-found in soil, water, vegetation and many animal species. See Bille & Doyle, 1990, *"Listeria* and *Erysipelothrix"* in Burbert, et al., Manual of Clinical Microbiology 5th ed., 231. Two *Listeria* species, *L. murrayl* and *L. grayd*, are rarely isolated and are presently considered nonpathogenic. However, five other species are genomically related and include three hemolytic species (*L. monocytogenes, L. seeligeri* and *L. ivanovii*) and two nonhemolytic species (*L. innocua*, and *L. welshimeri*). Of these, only *L. monocytogenes*, and sometimes *L. ivanovii* are human pathogens. *L. ivanovil* is mostly pathogenic for animals (Bille, infra).

*Listeria monocytogenes* is a facultative intracellular pathogen, capable of growth both in the external environment and inside mammalian cells. It is responsible for opportunistic infections in both humans and animals. The first cases of human listeriosis were reported in the 1930s and outbreaks have been traced to the consumption of contaminated food, most notably dairy and poultry products (Goebel et al., 1991, Infection, 19:5195-5197). Individuals at risk are the newborn, the elderly, and the immunocompromised.

Clinical features of the diseases are meningitis and meningoencephalitis. Infection with *L. monocytogenes* has also been observed as septicemia (with resulting abortion) in pregnant women, and patients with malignancies and immunosuppression. Some people, usually predisposed by an underlying cardiac illness, have been treated for endocarditis resulting from listerial infection.

Although *L. monocytogenes* is considered an uncommon adult pathogen, it is the third• most common cause of bacterial meningitis in neonates (McKay & Lul 1991, Infection & Immun., 59:4286-4290). Highest mortality and neurological sequelae among survivors is seen when the central nervous system is involved. However, underlying conditions which cause lower cell-mediated immunity, such as transplants, malignancy and AIDS, can result in increased mortality, up to 6.9%.

There has been a gradual increase in the incidence of human listeriosis since the 1960s. Presumably, this is related to the increased numbers of individuals with malignancies undergoing radiation and chemotherapy which allows for their prolonged survival but with immunosuppression as their consequence. Similarly, increases in renal transplantations has exposed increasing numbers of patients to possible infectious complications. Finally, with the rapid spread of AIDS and its suppression of immune function, it can be expected that the occurrence of human listeriosis may increase substantially in the future years.

The epithelial cells of the gastrointestinal tract may be the primary site of entry of *L. monocytogenes*. It was discovered in the 1960s that this bacterium can invade, survive and replicate within phagocytic cells, such as macrophages and 'monocytes (Michel & Cossart, 1992, J. Bacteriol., 174: 7098-7103). Nonprofessional phagocytes, which are unable to take up extracellularly growing bacteria, are also susceptible to invasion by this intracellular organism (Bubert et al., 1992, J. Bacteriol., 174:8166-8171). Apparently, *L. monocy-*

*togenes* is able to induce its own phagocytosis in these host cells. Specific virulence factors are required for this invasion and intracellular growth.

A major extracellular protein P60, named for its relative molecular weight of 60,000 daltons, is produced by all virulent *L. monocytogenes* strains. Protein P60 is derived from the Protein P60 Precursor also known as the. invasion-associated protein (iap) as described by Koehler, et al., 1990, Infect. Immun., 58:1943-1950. Moreover, the precursor protein is 484 amino acids in length and the sequence is known.

Spontaneously occurring mutants of *L. monocytogenes* that show a decreased level of the protein P60, known as R mutants, are avirulent and unable to invade nonprofessional phagocytes. R mutants are still phagocytized by macrophage with the same efficiency as wild-type bacteria and are able to replicate in these cells. Addition of partially purified P60 protein from wild-type *L. monocytogenes* restores the invasiveness of these R mutants into nonprofessional phagocytic cells. This finding has led to the conclusion that P60 is involved in the mechanism of uptake of *L. monocytogenes* by nonprofessional phagocytic cells.

The P60 protein of *L. monocytogenes* is 484 amino acids long, contains a putative N-terminal signal sequence of 27 amino acids and an extended repeat region of 19 threonine-asparagine units. The middle portion of the protein P60, consisting of about 240 amino acids, and located about 120 amino acids from both the N- and C-terminal ends, varies considerably from the deduced amino acid sequences of the related P60 proteins of *L. innocua, L. ivanovii, L. seeligeri, L. welshimeri* and *L. grayi*. From the predicted secondary structure and hydropathy studies on this protein, the hydrophilic middle portion consists of two alpha-helical regions flanking the repeat domain. Conversely, the hydrophobic N- and C-terminal ends are in predominantly B-pleated sheets, This would suggest that the middle. region is exposed on the protein's surface (Kohler, infra).

The CSF findings in *Listeria* meningitis are quite variable and often result in a negative gram stain. This means that confirmed diagnosis is dependent on culture of either blood or CSF samples, which may take up to 48 hours. Given its high mortality and morbidity, and the increasing numbers of populations at risk, it is apparent that the need exists for rapid diagnosis and for a vaccine against *L. monocytogenes* infections.

3. Mode of Central Nervous System (CNS) Infection

It is a well known feature of bacterial and viral meningitis etiological agents that they possess the ability to infect the CNS. Until recently, it was not known how these agents could pass the blood-brain barrier. The mechanism by, which circulating bacteria enter the CSF compartment has only recently been understood. Circulating organisms could invade the CSF compartment by translocation through or between vascular endothelial cells and underlying tissues before entering the CSF. In fact, vascular lesions are a feature of 20 meningitis caused by such organisms as *Salmonella choleraesuls* and *Pasteurella haeloytica*. See Wildock, 1977, Vet. Pathol., 14:113-120; and Sullivan, "The Nervous System: Inflammation", in Jubb et al., eds. 1985, Pathology of Domestic Animals, Volume 1:278-290.

However, while vascular endothelial damage may be integral to the pathogenic pathway for some bacteria, it is unlikely to be the mechanism of entry for most cases of meningitis, since vascular lesions are not a prominent early feature of meningitis caused by either *N. meningitidis, S. pneumoniae, E. coli, S. suls, parasuis, H. influenzae,* or *S. aureus* (Williams, 1990, J. Infec. Dis., 162:474-481).

It has been shown that bacteria can be carried into the CSF in association with monocytes migrating into the CSF compartment to maintain populations of resident macrophage (Cordy, 1984, Vet. Pathol., 21:593-597). This method of entry for bacteria is also analogous to the mechanism employed by some viruses (HIV, MaaediVisna-caprine arthritis encephalitis virus) when invading the CNS. See Peluso, 1985, Virology, 147:231-236; Narayan, 1985, Rev. Infec. Dis., 7:899-98; Roy, 1988, J. Leukoc. Clol., 43:91-97; and Westervelt, 1991, Vaccines, 91:71-76.

It is also known that cellular immune reactions consist of a complex series of coordinating events. In response to tissue injury, monocytes are recruited from bone marrow via the blood circulation (Robinson, 1989, PNAS, 86:1850-1854). These activated blood monocytes then differentiate into macrophage in response to several immune mediators produced at the site of inflammation (Yoshinura, et al., 1989, FEBS Letter, 244:487-493).

As macrophage normally function to protect the body from potentially toxic substances, either infectious or chemical in nature, they serve as scavengers, processing and presenting antigen to the B lymphocytes, which in turn produce antibodies. (Edington, 1993, Bib/Technology, 11:676-681), Macrophage are also known to secrete mediators that mediate systemic host defence responses and local inflammation.

The first evidence of mediators being involved in cellular immune reactions was noted in 1970 (Ward, 1970, Cell Immunol., 1:162-174). It was reported that addition of antigen to specifically sensitized lymphocytes caused release of an "activity" which attracted macrophage (Robinson, infra). It is now well known that immune mediators possess a variety of functions for cytokines such as the interleukins and interferons.

This led to the recent discovery of a family of small, secretory cytokine-like proteins called chemokines for their apparent chemotactic properties, whose complete proinflammatory functions have yet to be elucidated.• However, the size and amino acid sequence of many of these chemokines is known as illustrated in Michiel, 1993, Bio/Technology, 11:739.

4. Chemokines

The chemokines comprise a family of proteins, belonging to the superfamily of immune cytokines, wherein each member is related by a four cysteine motif. Evidence suggests chemokines function as regulators of inflammatory and immunoregulatory processes, playing key roles in physiologic and pathologic inflammation. In fact, the term "chemokine" is a contraction of chemoattractant and cytokine and has been sanctioned as the word used to describe molecules which share this four cysteine motif (see Lindley et al., 1993, lmmunol. Today 14, 24). Not all proteins belonging to the chemokine family exhibit chemoattractant activity and not all cytokines possessing chempattractant activity are considered "chemokines" if they do not possess this motif.

The family was subdivided into two subfamilies based upon whether the first two cysteines are either spaced by an intervening residue (the a or "C—X—C" branch) or adjacent (the 0 or "C—C" branch). Generally speaking, the C—X—C chemokines attract neutrophils but not monocytes, while C—C chemokines act conversely attracting monocytes but not neutrophils. Although there are fewer C—C chemokines than C—X—C chemokines, more bioactivities for C—C chemokines as a class have been reported leading to the view that these chemokines act as links between monocytes, lymphocytes, basophils and eosinophils during immune and inflammatory processes (Schall, .T. J., 1994, The Cytokine Handbook, 2nd ed., thompson A., Ed; Academic Press). Recently however, a new class of chemokines, the "C" subfamily, has been discovered, which lacks the first and third cysteine in the four cysteine chemokine motif.

It is further known that the chemokines appear to be functionally involved in cell chemotaxis. Their amino acids sequence diversity suggests that each chemokine has distinct cellular specificity, each having its own unique cellular targets. This cellular specificity appears related to seven transmembrane-domain receptors in each chemokine, but the overlapping pattern of ligand binding and their regulation has yet to be determined. (Rollins, et al., 1989, Molecular & Cellular Biol., 9:4687-4695).

The C—C chemokines have been reported to act as links between monocytes, lymphocytes, baSophils and eosinophils during immune and inflammatory processes. A few recent. reviews have been conducted of the individual C—C chemokines (Schall, T. J., 1991, Cytokine 3, 165-183; Miller and Krangel 1992a; Jose et al., 1994, J. Exp. Med., 179:881). At least eight distinct human C—C chemokines have been reported, comprising the 1 & 2) macrophage inflammatory proteins-1a and -g (MIP-1a and MIP-113); 3) T cell activation gene 3 (TCA3); 4) RANTES (an acronym for Regulated upon Activation, Normal T cell Expressed and Secreted); 5) rclonocyte chemotactic protein (MCP-1); 6) monocyte chemotactic protein-2 (MCP-2); 7) monocyte chemotactic protein-3 (MCP-3); and 8) a new eosinophil active C—C chemokine designated eotaxin.

There is a vast literature concerning the discovery, characterization, and biological activities of MCP-1, its presumed murine counterpart JE, and its related proteins MCP-2 and MCP-3. Aa with all chemokines, various names have been used to identify MCP-1. The following terms are therefore interchangeable for those skilled in the art: GDCF-2: for Glioma-Derived Monocyte Chemotactic Factor; hJE: for human JE gene product; MCAF: for Monocyte Chemotactic Factor; and MCP-1: for Monocyte chemoattractant Protein-1. As the amino acid sequences for these chemokines was found to be identical, the term MCP has been adopted for describing this particular chemokine and the other chemokines that share significant sequence homology with MCP-1. These have been named MCP-2 and MCP-3, according to the order of their discovery.

Cloning and sequencing studies have shown that human MCP-1 (hMCP-1) is highly homologous to the mouse JE gene product (Yowhimura, T. et al., 1989 FEBS Lett. 244-487; Rollins, B. J. et al., 1989, Proc. Natl. Acad. Sci. USA, 85:3738). The JE gene, originally identified in murine fibroblasts as a platelet-derived growth factor (PDGF)-inducible gene, is now considered to be the mouse homologue of MCP-1. Murine JE was initially discovered as a transcript induced rapidly in fibroblasts by PDGF was subsequently cloned and characterized by Rollins and colleagues (Rollins, B. J., et al., 1988, Proc. Natl. Acad. Sci., USA, 85:3738).

A subsequent discovery of a human monocyte-chemoattractant protein was made. Human MCP-1 was first purified on the basis of its ability to chemoattract monocytes (Miller, M. D., and Krangel, M. S., 1992, Critical Rev. Immunol., 12:17; Schall, T., 1994, The Cytokine Handbook, 2nd ed., Thompson, A., Ed., Academic. Press:New York, p. 419; Leonard, E. J. and Yoshimura, 1990, Immunol. Today, 11:97; Matsushima, K. and Oppenheim, J. J., 1989, Cytokine, 1:2). It later became clear to all investigative groups that the human factor was homologue of murine JE (Yoshimura et al., 1989c, Robinson et al., 1989, Furutani et al., 1989, Rollins et al., 1989, and Chang et al., 1989). The murine and human molecules are distinct in that the JE protein is C7 terminally extended by 49 amino acids, making it considerably larger than the hMCP-1, which is 99 amino acids long. Human MCP-1 is secreted from mammalian cells in perhaps 3 forms, each resulting from difference post-translational carbohydrate modifications (Yoshimura and Leonard, 1990a, Leonard and Yoshimura 1990, Jiang et al., 1990, Jiang et al., 1991). The biological differences, if any, between these forms are not clear.

Two additional MCP molecules have been reported and are designated MCP-2 and MCP-3 (Van Damme, et al., 1992, J. Exp. Wed., 176:59-65); their amino acid sequences were found to be 62% and 73%, respectively, homologous to MCP-1. they share MCP-1's chemoattractant specificity for monocytes in vivo (Van Damme et al., 1992). The cDNA for MCP-3 has also been isolated (Opdenakker et al., 1993), and a murine cDNA designated MARC is likely to be the murine homologue of either MCP-2 or MCP-3. Interestingly, it is not C-terminally extended like the presumed MCP-1 homologue, murine JE.

Like most secreted proteins, the chemokines are synthesized with a hydrophobic leader sequence which is cleaved to produce the mature, active chemokine. The amino acid sequence of MCP-1 shows the mature protein to be 99 amino acids long starting at what corresponds to nucleotide 70 of the gene. The functional portion of the protein is known to be the active portion with the first 23 amino acids serving as a signal sequence. MCP-1 is a secretory N-glycosylated glycoprotein of a variety of molecular weights but predominantly occurring at 13,000; 15,000; and 15,500 Daltons with post-translational modification probably accounting for the various forms, The two former isoforms have been named alpha and beta respectively but the structural differences between the two are still unknown. Yet, is known that their amino acid sequences are identical, apparently derived from a single gene product.

Many mitogenic and activating stimuli appear to cause secretion of MCP-1 by a wide variety of cells. These findings suggest that the cellular regulation of MCP-1 expression is complex, and involves circulating cytokine levels in addition to other factors. Viral and bacterial infections in turn, can affect these levels and are thus involved in the function of MCP-1.

The MCP chemokines comprise a distinct subgroup within the C—C family, the significance of the existence of the 'MCP group' within the chemokines family is not yet clear. Almost all cells or tissues examined will make MCP-1 upon stimulation by a variety of agents, but the targets of MCP-1 appear to be limited to monocytes and basophils. they act by attracting and, activating leukocytes. Therefore, 'MCP activity' is a broad term encompassing several steps which—result in the recruitment of immature monocytes and their differentiation into macrophages with specific functions. MCP activities may include: realignment of MCP structure to produce an active molecule (eg. dimer formation); chemoattraction to result in specific taxis of monocytes; binding of MCP to surface receptor of the recruited monocyte; activation of metabolic pathways in the monocyte to result in differentiation to •the mature, functional macrophage (i.e., lipid-scavenging macrophage).

Recent information has been obtained regarding active regions of the MCP-1 molecule, using a series of deletion. mutants (see Rollins, Chemotactic Chemokines, supra). These results may be summarized as follows. The N terminal 2-8 residues are essential for activity (recruitment and binding to monocytes), as their deletion results in a loss of more than 99.9% of MCP activity. Amino acids Y28 and R30 are essential for activity due to their position, emerging from one face of the beta sheet. These appear to be essential for interactions with glycosylated components.

The C-terminal septapeptide sequence of the MCP-1 molecule may be important in determining the specificity of chemoattraction of appropriate monocytes or may confer specificity on the differentiation process following chemokine binding to the immature monocyte. Such a significant functional role for the C-terminal septapeptide could make it an attractive sequence for incorporation, into infectious organisms which would benefit by acquiring this function.

Accordingly, there is a need for a rapid and a sensitive diagnostic test for the detection of the meningitis-causing organisms. Therefore, there remains a need for a diagnostic system which would detect RV protein antigens in CNS tissue in both the presence as well as the absence of an active, productive infection.

There is a need for a rapid and effective diagnostic test to screen large numbers of asymptomatic individuals for the presence of meningitis-causing organisms.

There is also a need for a non-infectious, innocuous vaccine for meningitis. No epitope has yet been identified which would induce only neutralizing antibodies, necessary for conferring effective vaccine protection against the diverse organisms that cause meningitis.

There remains a significant and urgent need to determine the mechanism used by meningitis etiological agents, as diverse as bacteria and viruses, to attract and infect monocytes and/or gain access to the CNS.

There also remains a significant and urgent need to develop a therapeutic capable of blocking such infection, of the CNS by bacterial and viral meningitis etiologic agents utilizing such a mechanism.

There remains a need for a monoclonal antibody specific for both bacterial and viral infectious agents of meningitis, where said monoclonal antibody recognizes both bacterial and viral infectious agents of meningitis and has substantial diagnostic utility.

Additionally, there is a need for a known proteinaceous region containing the epitope(s) recognized by said monoclonal antibody where said epitope or peptide could be chemically synthesized, thereby avoiding the difficulties inherent in purification and administration of larger fragments of the antigenic molecules.

An additional need for this said peptide is evident for use in diagnostic test kits to indicate meningitis infection as well as use in the development of general meningitis vaccine.

SUMMARY OF THE INVENTION

An object of the present invention is to provide a polypeptide comprising (A) a first amino acid sequence at the amino terminus of the polypeptide wherein the first amino acid sequence corresponds to an amino acid sequence of the carboxy terminus of a chemokine, and (B) a second amino acid sequence corresponding to the amino acid sequence of a hapten.

Another object of the present invention is to provide a hapten polypeptide comprising (A) as first, amino acid sequence a the amino terminus of the polypeptide wherein said amino acid sequence corresponds to the carboxy terminus of a human chemokine, and (B) a second amino acid sequence corresponding to a MRHAS.

Yet another object of the present invention is to provide a vaccine for preventing disease comprising (A) a first amino acid sequence at the amino terminus of the polypeptide wherein the first amino acid sequence corresponds to an amino acid sequence of the carboxy terminus of a chemokine, and (B) a second amino acid sequence corresponding to the amino acid sequence of a hapten polypeptide, and a pharmaceutically or veterinarilly acceptable carrier.

A further object of the present invention is to provide a vaccine for preventing disease comprising (A) a first amino acid sequence at the amino terminus of the polypeptide wherein the amino acid sequence corresponds to the carboxy terminus of a human chemokine, and (B) a second amino acid sequence corresponding to a MRHAS, and a pharmaceutically or veterinarilly acceptable carrier.

Other objects, features and advantages of the present invention will become apparent from the following detailed description. It should be understood, however, that the detailed description and the specific examples, while indicating preferred embodiments of the invention, are given by way of illustration only. Indeed, various changes and modifications within the spirit and scope of the invention will become apparent to those skilled in the art from this detailed description.

BRIEF DESCRIPTION OF THE DRAWINGS

FIG. 1 depicts the amino acid sequence A of the Structural Polyprotein protein of the M22 strain of Rubella virus with sequences of interest underlined. Amino acid sequences of all proteins described in detail in the present invention are given using the following single letter code: A=ala, C=cys, D=asp, E=glu, F=phe, G=gly, H=his, I. ile, K=lys, L=leu, M=met, N=asn, P=pro, Q=gln, R arg, S=ser, T=thr, V=val, W=trp, Y=tyr.

Figure 2:
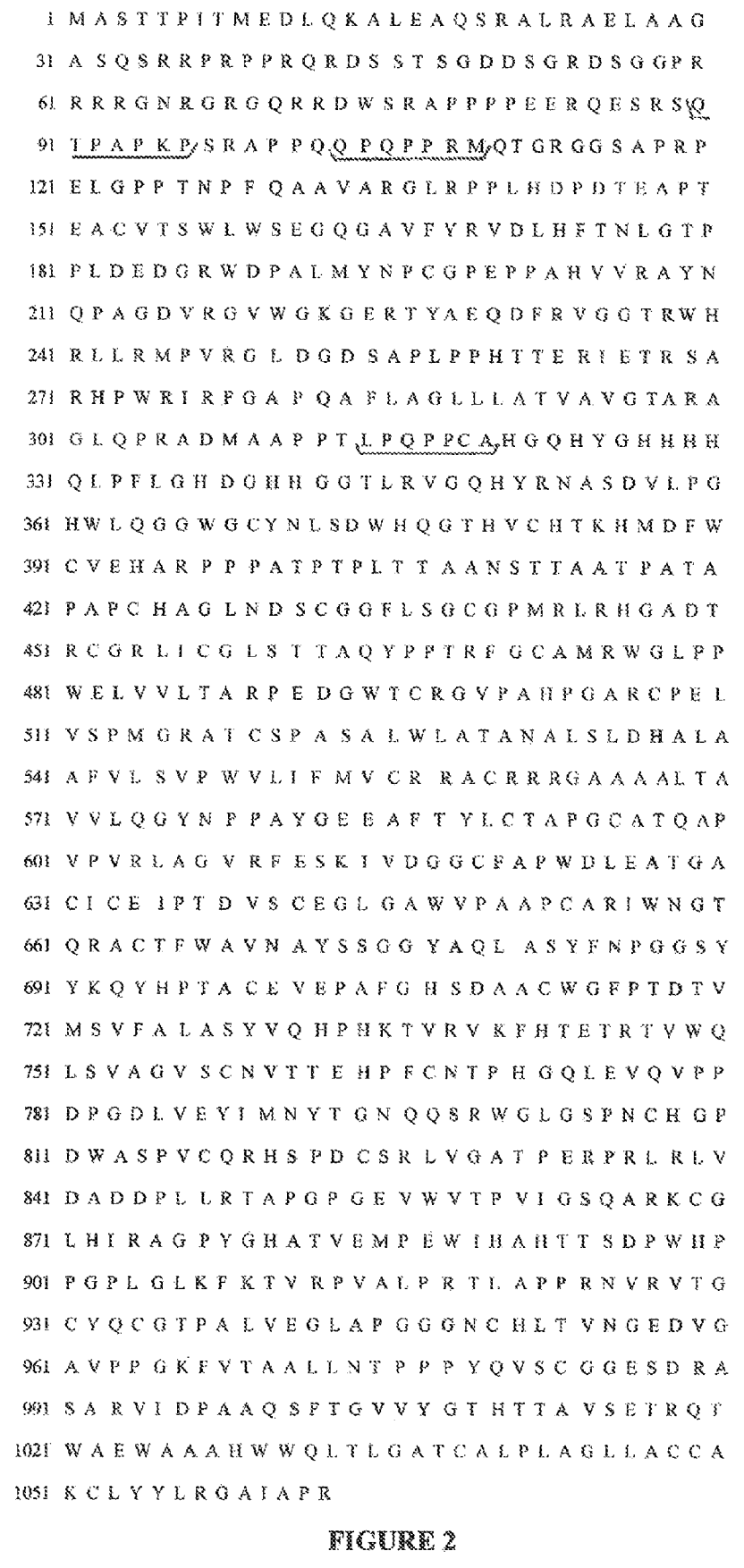

FIG. 2 depicts the amino acid sequence (Seq ID No: 8) of the Structural Polyprotein of the Therien strain of Rubella virus with sequences of interest underlined.

FIG. 3 depicts the amino acid sequences (Seq ID No: 11) of the Gag Polyprotein of the LV isolate of HIV-1 with sequences of interest underlined.

FIG. 4 depicts the amino acid sequence (Seq ID No: 14) of the Envelope Polyprotein Precursor protein of the LV-1a isolate of HIV-1 with sequences of interest underlined.

FIG. 5 depicts the amino acid sequence (Seq ID No: 17) of the Lipoprotein E Precursor of *Haemophilus influenzae* with sequences of interest underlined.

FIG. 6 depicts the amino acid sequence, (Seq ID No: 20) of the Opacity-Related Protein of *Neisseria meningitidis* with sequences of interest underlined.

FIG. 7 depicts the amino acid sequence (Seq ID No: 7) of the Pneumococcal Surface Protein A of *Streptococcus pneumoniae* with sequences of interest underlined.

FIG. 8 depicts the amino acid sequence (Seq ID No: 26) of Protein P60 Precursor of *Listeria monocytogenes* with sequences of interest underlined.

FIG. 9 depicts the amino acid sequence (Seq ID No: 35) of the chemokine hMCP-1 with sequences of interest underlined.

FIG. 10 depicts the amino acid sequence (Seq ID No: 38) uof the chemokine HMCP-3 with sequences of interest underlined.

FIG. 11 depicts the immunoblots of RV antigens reacted with Mab's RV1, RV2, RV3 and RV4. RV antigen: Strain MPV-77 (lot# 50678, Catalogue # EL-05-04) cultured in Vero cells. Purchased from Microbix Biosystems Inc., Toronto, Ontario). All Mab used as tissue culture fluid diluted 1/500. Lane 1—Molecular weight markers of 97, 66, 45, 31, 21, and 14 kD. Lane 2/3—RV4; lane 4/5/6—RV3; lane 7/8—RV2; lane 9/10—RV1. Lanes 2-9 all illustrate two proteins, 31 kD (major) and 45 kD (minor), identified by reactions with Mab's 1-4.

FIG. 12 depicts immunoblots of bacterial antigens reacted with V Mab RV1. *H. Influenzae* b antigen from ATCC (#10211); *L. monocytogenes* from ATCC (#7644); S/pneumoiae from the Caribbean Regional Epidemiology Centre, CAREC, Trinidad; *N. meningitidis* A from ATCC (#13077) Lane 1—Molecular weight markers of 97, 66, 45, 31, 21 •and 14 kD. Lane 2—*H. Influenzae* b—proteins of approximate weights of 50, 45, 40, and 25 kD. Lane 3—*L. monocytogenes*—proteins of approximate weights of 60 kD (major) and 66 kD (minor), Lane 4/5—*S. pneumoniae*—proteins of approximate weights of 60 kD and 66 KD, Lane 6/7—*N. meningitidis*—protein of approximate weights of 18 kD, identified by reaction with Mab Rv1.

DETAILED DESCRIPTION OF THE INVENTION

1. Definitions

Figure 13:
FIG. 13 depicts immunoblots of HIV1 antigens reacted with RV Mab RV1. HTLV-IIIB viral •lysate, lot #54-040, purchased from Applied Biotechnologies, Inc., Md., USA. Lane 1—Molecular weight markers of 97, 66, 45, 31, 21 and 14 kD. Lane 2—Control RV antigens, 31 and 45 kD, reacting with RV 1 Mab. Lane 3/4—HIV1 antigen of approximate weights of proteins at 24 kD and 61 kD, identified by reaction with Mab RV1.

An antibody includes polyclonal and monoclonal antibodies and denotes any naturally or non-naturally occurring polypeptide having the binding specificity. An antibody includes a half antibody molecule (a single heavy:light chain pair), or a fragment, such as the univalent fragments Fab or Fab' and the divalent fragment F(ab')2 ("FAB" meaning fragment antigen binding), that possess the same specificity as the whole antibody. A fragment, according to the present invention may also be a single chain Fv fragment produced by methods well known in the art. See Skerra et al: Science, 240: 1038-1041 (1988) and King et al. Biochemical J., 290: 723-729 (1991). The antibody of the present invention also includes a non-peptide compound which is a "mimetic," i.e. which mimics the epitope binding site of an antibody, but is water soluble, resistant to proteolysis and non-immunogenic. Conformationally restricted cyclic organic peptides which mimic an antibody can be produced in accordance with method well-known to the skilled artisan. See e.g., Saragovi, et al., Science, 253:792-795 (1991). The antibody of the present invention also includes anti-idiotypic antibodies produced by methods well-known to the art of the invention. See, e.g. Cozenza, Eur. J. Immunol., 6:114 (1976)

A conservative substitution denotes the substitution of one or more amino acids for another in which the antigenic determinant (including its secondary structure and hydropathic nature) of a given antigen is completely or partially conserved in spite of the substitution.

The term analogues of a peptide refers to amino acid insertions, deletions, substitutions, and modifications of one or more sites in the peptide chain.

The term immunogenic refers to the property that endows a substance with the capacity to provoke an immune response.

The terms corresponds and corresponding refer to the native amino acids of a defined region of a given peptide sequence, or any technically feasible modification of the given sequence. Amino acids such as cysteine, lysine, glutamic or aspartic acid, tyrosine, or the like may be introduced at the C- or N-terminus of a given peptide or oligopeptide to provide for a useful functionality for linking purposes. It will be appreciated by those skilled in the art that cysteine is particularly preferred to facilitate covalent coupling to other peptides or to form polymers by oxidation.

An immunochemical reaction denotes the specific interaction which occurs between an antigen and its corresponding antibody, regardless of the method of measurement. Such a reaction is characterized by a non-covalent binding of one or more antibody molecules to one or more antigen molecules. The immunochemical reaction may be detected by a large variety of immunoassays known in the art.

Immunogenic or antigenic are terms used hereto describe the capacity of a given substance to stimulate the production of antibodies specifically immunoreactive to that substance when that substance is administered to a suitable test animal under conditions known to elicit antibody production.

A protective antigen denotes the ability of a given immunogen to confer resistance in a suitable host, against a given pathogen.

An epitope denotes a specific antibody site on an antigen. Macromolecular antigens such as proteins typically have several epitopes with distinctive antibody binding specificities.

A hapten is a small molecule which can act as an epitope but is incapable by itself of eliciting an antibody response.

A chimeric protein or peptide is comprised of an amino acid sequence taken from two or more functionally and/or structurally distinct proteins or peptides.

A Meningitis Related Homologous Antigenic Sequence MRHAS) is an amino acid sequence that corresponds to antigenic sites on the Structural Polypeptide (within the core and E2 membrane protein portion) of Rubella virus that are recognized by a Mab from the hybridoma RV-1. More specifically, any amino acid sequence, that is. homologous to the regions extending from approximately amino acid residue 102 to 108 of the Structural Polyprotein (core protein region) and from about 313 to 319 of the Structural Polyprotein (E2 membrane protein) of the M33 strain of Rubella virus is by definition a member of the MRHAS family of sequences. The complete sequence of this Structural Polyprotein is found in FIG. 1. Representative members that are cross-reactive with the RV1-Mab and appear in bacteria and viruses known to cause meningitis are presented in Table 1. The sequences of some of the proteins listed in Table 1 are found in FIGS. 1-8.

2. Overview

The present invention provides polypeptides comprising amino acid sequences that correspond to a chemokine and a hapten and that are useful as vaccines and in the treatment of disease. The hapten can be any small molecule which can act as an epitope but is incapable by itself ct eliciting an antibody response.

The polypeptides of the present invention may include a hapten that is a "Meningitis Related Homologous Antigenic Sequence" (MRHAS) from a bacterial or viral agent known to cause meningitis. These peptides induce protective immunity in a host susceptible to meningitis. The present invention also relates to materials useful in the diagnosis of diseases, including meningitis, by providing monoclonal antibodies, peptides, and mixtures and combinations thereof, that are useful in detection of disease-causing organisms.

The present invention also provides antibodies reactive with such antigenic regions and peptides. In addition, the invention provides analogues of those peptides and mixtures and combinations of those peptides and analogues. These novel materials find use in, for example, •a wide variety of diagnostic and preventive methods, means and compositions with respect to the overall process of pathogenesis which uses chemokine function to promote disease including meningitis, and atherosclerosis.

The present invention provides novel compositions and methods for detecting, preventing and therapeutically treating disease wherein the pathogen or pathogenic mechanism includes a monoclonal antibody defined antigenic sequence. More specifically, using a monoclonal antibody defined by two rubella virus antigenic sites, a family of homologous cross-reacting antigenic sequences were, identified in proteins associated with meningitis etiologic agents. These cross reacting antigenic sequences were in turn found to be significantly homologous to the C-terminal sequence of the monocyte attracting chemokines hMCP-1 and hMCP-3.

Hence, this invention involves the use of peptides that mimic these homologous cross-reacting antigenic sequences and monoclonal antibodies reactive with such amino acid sequences to diagnose, treat and vaccinate against diseases wherein the pathogenic mechanism involves one or more members of these homologous cross-reacting sequences. An example of such a disease is meningitis.

A monoclonal antibody was used to identify two cross-reacting septapeptide antigens (QPQPPRM and PPQPPRA) contained in the Structural Polyprotein (Core and E2 outer membrane proteins portion described in greater detail) of Rubella virus. The monoclonal antibody, RV1-Mab, was also found to cross-react with the p24 Core protein and the p61 outer membrane protein of Human Immunodeficiency Virus-1 (HIV-1), known to cause meningitis during the initial stages of infection. Furthermore, the RV1-Mab was also found to cross react with proteins found in *Hemophilus influenzae, bleisseria meningitidis, Streptoccus pneumoniae* and *Listeria monocytogenes*, which together account for more than 85% of all bacterial meningitis in the United States. In this way, a family of homologous cross-reacting septapeptide antigens were discovered in viruses and bacteria known to cause meningitis. Because the RV1-Mab binds to amino acid sequences in diverse bacteria and viruses that are related only in the fact that they cause meningitis, these closely related homologous sequences have been designated Meningitis Related Homologous Antigenic Sequence (MRHAS). Representative members of the family of proteins containing MRHAS are shown in Table 1. (Seq ID Nos: 3, 5, 7, 10, 13, 16, 19, 22, 25, 28, 30, 32, 34, and 41-74, respectively)

TABLE 1

| NAME | VIRUS/BACTERIUM | PROTEIN (& POSITION) | SEQUENCE |
|---|---|---|---|
| MRHASRV-1 | Rubella Virus | Structural | QPQPPRM |
| MRHASRV-2 | | Polyprotein (Core) | QTPAPKP |
| MRHASRV-3 | | Structural | PPQPPRA |
| MRHASRV-4 | | Polvorotein (E2) | LPQPPCA |
| MRHASHIV-1 | HIV 1 | Gag Polyprotein | QAISPRT |
| MRHASHIV-2 | | Env Polyprotein Precursor | QNQQEKN |
| MRHASHI-1 | Hemophilus Influenzas | Lipoprotein E Precursor | QVQNNKP |
| MRHASNM-1 | Nisseria meningitidis | Opacity-Related Protein POPM3 | IQPPKN |
| MRHASSP-1 | Streptococcas pneumoniae | Pneumococcal Surface Protein A | QQQPPKA |
| MRHASLM-1 | *Listeria* | Protein P60 | PTQEVKK |
| MRHASLM-2 | *monocytogenes* | Precursor | TTpAPKV |
| MRHASLM-3 | | | NTATPKA |
| MRHASLM-4 | | | QQTAPKA |
| MRHASMV-1 | MUMPS VIRUS | CORE (422) | QQQQPAA |
| MRHASMV-2 | MUMPS VIRUS | CORE (533), | QTIPIKT |
| MRHASMV-3 | MUMPS VIRUS | FUSION PROTEIN | QAQTNAR |
| MRHASMES-1 | MEASLES VIRUS | FUSION PROTEIN (44) | YTTVPKY |
| MRHASMES-2 | MEASLES VIRUS | FUSION PROTEIN (271) | LTGTSKS |
| MRHASREO-2 | REOVIRUS TYPE 1 | LAMBDA 3 (239) | LQQTAGL |
| MRHASREO-1 | REOVIRUS TYPE 3 | SIGMA 3 (203) | QTQFSRT |
| MRHASRHINO=1 | RHINOVIRUS 14 | CORE PROTEIN P3A (1512) | QTQGPYS |
| MRHASRHINO-2 | RHINOVIRUS 2 | COAT PROTEIN VP3 (529) | PPQTPPT |
| MRHASRSV-1 | RESPIRATORY | G SURFACE (14D) | QAQPNKS |
| MRHASRSV-2 | SYNCYTIAL VIRUS | PROTEIN G PROTEIN VARIENT | QTQPSKP |
| MRHASHLCV-1 | HUMAN | CORE (186) | QSQTPLN |
| MRHASHLCV-1 | LYMPHOCYTIC CHORIO-MENINGITIS VIRUS | SURFACE (385) | ETSVPKC |
| MRHASCOX-1 | COXSACKIE A24 | PROTEIN RNA (18871 | QTRDTKE |
| MRHASCOX-2 | VIRUS | COAT PROTEIN (4) | QVSTQKT |
| MRHASCOX-3 | COXSACKIE A21 VIRUS COXSACKIE A9 VIRUS | PROTEIN RNA (2143) | WTKDPKN |
| MRHASENT-1 | ENTEROVIRUS 70 | GENOME-LINKED PROTEIN (1539) | PNQKPKV |
| MRHASEB-5 | EBOLA VIRUS | ENV CLYAPROTEIN (18) | QSLTTKP |
| MRHASEB-1 | | VP35 (72) | QTQTDPI. : |
| MRHASEB-2 | | VP35 (329) | QLQDGKT |
| MRHASEB-3 | | VP35 (136) | QEEGPKI |
| MRHASEB-4 | | ENV GLYCOPROTEIN (76) | NTNTSKS |
| MRHASTB-1 | TUBERCULOSIS | MPT64 PROTEIN (21) | ATAAPKT |
| MRHASLY-1 | *BORRELIA* | 80 K ANTIGEN (233) | QGETHKA |

TABLE 1-continued

| NAME | VIRUS/BACTERIUM | PROTEIN (& POSITION) | SEQUENCE |
|---|---|---|---|
| MRHASLY-2 | BURGDORFERI (LYME DISEASE) | FLAGELLIN (221) | QQPAPAT |
| MRHASMAL-1 | PLAOMODIUM | SURFACE AG (41) | STQSAKN |
| MRHASMAL-2 | FALCIPASUM | 45Kd AG (85) | QTTTPTA |
| MRHASCMV-1 | CYTOMEGALOVIRUS | PHOSPHOPROTEIN (615) | QTQTPVN |
| MRHASCMV-2 |  | PHOSPHOPROTEIN (822) | QPASSKT |
| MRHASCMV-3 |  | PHOSPHOPROTEIN PP28 (160) | RPDTPRT |
| MRHASCMV-4 |  | 45kD EARLY (281) | VTHPPKV |
| MRHASNM-1 | NISSERIA MENINGITIDIS | PROTEIN POPM3 | *IQPPKN |
| MRHASNM-2 |  | PROTEIN POPM1 (1) | *IQPPKT |
| MRHASNM-3 |  | PROTEIN CLASS 2 (276) | QTQVAAT |

It is noted that within the Structural Polyprotein of Rubella virus, there are three proteins that can be ultimately derived. Therefore, when a reference is made 25 to either the Core protein portion or the E2 membrane-associated protein portion (from either the M33 or Therien strains), this reference denotes the portion of the Structural Polyprotein from which the final mature protein will be derived. A similar nomenclature with respect to precursor versus mature protein was also used in connection with the Gag Polyprotein of HIV-1, the Envelope Polyprotein Precursor of HIV-1, the Lipoprotein E Precursor, and the Protein P60 Precursor. For example the Protein P60 Precursor has, at a minimum, a 27 amino acid leader sequence that is removed during processing to mature protein.

Members of the MRHAS family were also found to appearin two variants of the chemokine, human Monocyte Chemoattractant Factor (hMCF). These two are hMCP-1 and hKCP-3, as indicated in Table 2. (Seq ID Nos: 37 and 40, respectively) The sequences of the factors listed in Table 2 are found in FIGS. 9 and 10. (Seq ID Nos: 35 and 38, respectively)

TABLE 2

| NAME | FACTOR | I POSITION | SEQUENCE |
|---|---|---|---|
| MRHASMCP-1 | hMCP-1 | 70-76 | QTQT P KT |
| MRHASMCP-3 | hMCP-3 | 61-67 | KTQTPKL |

It is surprising that bacteria, viruses and spirochetes as diverse as *Hemophilus influenzae, Neisseria meningitidis, Streptococcus pneumoniae, Listeria monocytogenes*, RV, HIV-1, *P. fallcipar* and *B. burgdorferi* share a common feature, namely the placement of MRHAS, a highly conserved sequence, on the outer membrane. However, some of these etiological agents of meningitis do share specific features. For example, Williams and Blakemore have shown that bacteria can be carried into the CNS in association with monocytes migrating into the CSF compartment to maintain populations of resident macrophages (Cordy, 1984, Vet. Pathol., 21:593-597). This method of entry for bacteria would be analogous to that by which some viruses (HIV, Maaedi-Visna-caprine arthritis encephalitis virus) invade the CNS (Peluso, et al., 1985, Virology, 147:231-236; Narayan and Cork, 1985, Rev. Infec. Dis., 7:899; Roy and Wainberg, 1988, J. Leukoc. Clol., 43:91-97; Westervelt et al., 1991, Vaccines, 91:71-76). Moreover, available information for HIV-1 indicates that significant alterations in proteins carrying the MRHAS alters virulence, or invasiveness of the organisms.

Since the MRHAS that appear on bacteria, viruses and spirochetes are significantly homologous to sequences found in monocyte attracting chemokines, it is apparent that these agents have incorporated these sequences into their proteins to attract monocytes to aid in infection.

The unexpected discovery of monoclonal antibody cross-reactivity over various viral and bacterial species known to cause meningitis provides novel means for therapeutic and prophylactic treatments of meningitis. Moreover the utility of this invention is extended by the significant homology of these antigenic sites with amino acid sequences in monocyte attracting chemokines. These novel means may be applied to diseases as diverse as meningitis and atherosclerosis, wherein the pathogen or pathogenic mechanism includes one or more of these MRHAS.

More specifically, a hybridoma is used to produce cross-reacting monoclonal antibodies that bind MRHAS in vivo and in vitro. These antibodies are useful as a diagnostic tool to detect the presence of MRHAS. One such diagnostic use is to detect the presence of bacterial and viral agents of meningitis in biological samples. Such Mabs are also useful for treating a patient to prevent and/or treat infection due to a meningitis etiologic virus and/or bacteria. A bacterial and/or viral meningitis infection can also be detected using peptides mimicking MRHAS in a diagnostic test. in vivo, peptides mimicking MRHAS can also be used as a novel vaccine for meningitis, in addition to use as blocking agents (therapeutics) to prevent the accumulation of monocytes involved in CNS infection and diseases such as atherosclerosis.

In one aspect, the novel peptides, typically less than about 30 amino acids, contain seven or more contiguous amino acids forming epitopes substantially similar to epitopes located on viruses and/or bacteria known to cause meningitis and/or on chemokines known to attract monocytes. Of particular interest are the regions extending from about amino acid residue: 102 to 108 (core protein portion), 89 to 95 (core protein portion), and 313 to 319 (E2 membrane portion) of the Structural Polyprotein of the M33 strain of Rubella virus; from about 314 to 320 (E2 membrane portion) of the Structural Polyprotein of the Therien strain of Rubella virus; from about 145 to 151 of the Gag Polyprotein of the LV isolate of HIV-1; from about 655 to 661 of the Envelope Polyprotein Precursor of the LAV-1a isolate of HIV-1; from about 99 to 105 of the Lipoprotein E Precursor of *Haemophilus influenzae*; from about 1 to 5 of the Opacity-Related Protein POPM3 of *Neisseria meningitidis*; from about 423 to 429 of the Pneumococcal Surface Protein A of *Streptococcus pneumoniae*; from about 151 to 157, 181 to 187, 249 to 255, and 292 to 298 of the Protein P60 Precursor of *Listeria monocytogenes*; from about 93 to 99 of the chemokine hMCP-1; and from about 61 to 67 of the chemokine hMCP-3.

Those skilled in the art will appreciate that additional analogous regions ("homologs") from other infectious agents (viruses, bacteria, etc.) or chemokines may be identified based upon their sequence homology with members of the MRHAS family. In practice, such homologs may be identified by reference to the MRHAS occurring in hMCP-1 QTQTPKT (Seq ID No: 37).

This method can be applied to other infectious agents (viruses, bacteria, etc.) or chemokines that are yet to be discovered. For example, as new viruses or bacteria are identified that use monocytes to infect various regions of the body such as the CNS, their protein amino acid sequences may be aligned with that of the MRHAS in 20 hMCP-1 to obtain maximum homology. The methods by which the sequences are aligned are known to those skilled in the art. The amino acid sequence of an infectious agent not listed herein, which corresponds to members of the MRHAS family specifically disclosed herein can be synthesized and used in accordance with the invention.

It is not necessary to the present invention that the epitopes contained within such sequences be cross-reactive with antibodies to all infectious agents of meningitis, or all chemokines that attract monocytes. Peptides encompassing immunological epitopes which distinguish between types of monocytes or between epitopes for a particular type of Monocyte will find utility in identifying different pathogenic mechanisms of infection and disease. For example, such utility will include infectious agents that use different modes of infectivity to enter the CNS. These peptides may also be useful in combination with other peptides representing other members of the MRHAS family in therapeutic composition.

3. Generation of Monoclonal Antibodies

Monoclonal antibodies were prepared by immortalizing the expression of nucleic acid sequences that encode for antibodies or binding fragments thereof specific for members of the MRHAS family. See Godding, 1980, "Antibody Production by Hybridomas", J. Immunol. Meth., 39:285-308. In brief, spleen cells from an immunized vertebrate that illustrate the desired antibody response are immortalized.

Immunization protocols are well established and though such protocols can be varied considerably, they still remain effective. Also see, Goding, 1986, Monoclonal Antibodies: Principles and Practice, Academic Press, 2nd edition. Cell lines that produce the antibodies are most commonly made by cell 15 fusion between suitably drug-marked human or mouse myeloma or human lymphoblastoid cells with human B-lymphocytes to yield the hybrid cell lines. Other methods include Ebstein-Barr Virus transformation of lymphocytes, transformation with bare DNA (such as oncogenes or retroviruses), or any other method which provides for stable maintenance of the cell line and the production of monoclonal antibodies. The general methodology followed for obtaining monoclonal antibodies is described in Kohler & Milstein, 1975, Nature, 256:495-496. The transformation or fusion can be carried out in conventional ways, the fusion technique being described in a number of patents: U.S. Pat. Nos. 4,172,124; 4,350,683; 4,363,799; 4,381,292; and 4,423,147. The procedure is also described by Kennett et al., Monoclonal Antibodies (1980) and references therein, as well as Goding, infra. Human monoclonal antibodies are acquired by fusion of the spleen cells with the appropriate human fusion partner, such as W1-L2 and as described in European Application No. 8,2, 301103.6, the relevant portions of such a procedure incorporated herein by reference. A detailed technique' for producing mouse X mouse monoclonal antibodies is taught by Oi & Herzenberg, in Mishell & Shiigi, 1980, Selected Methods in Cellular Immunology, 351-372. The resulting hybridomas are screened to isolate individual clones, where each clone secretes a single monoclonal antibody to a given MRHAS.

The antibodies generated herein can be used without modification or may be modified in a number of ways. For example, such modification can be by way of labeling. (meaning joining), either covalently or non-covalently, a moiety which directly or indirectly provides for some means of detection. A variety of such labels are known and include: substrates, enzymes, co-factors, inhibitors, chemiluminescers, fluorescers, radionuclides, magnetic particles, and the like.

Moreover, fragments of such monoclonal antibodies can exist that continue to possess notable specificity for a given MRHAS. As such, all aptibody binding fragments or reference to such 'fragment(s) thereof' refers to a lesser portion of a complete antibody that retains some, if not all, of its binding specificity and capacity for a given MRHAS.

Therefore, one preferred embodiment of this invention involves a composition comprising a monoclonal antibody or binding fragment thereof which binds to one or more members of a group of homologous antigenic amino acid sequences comprising MRHAS.

A further embodiment of this invention involves a cell line that produces a monoclonal antibody or binding fragment thereof which binds to members of a family comprising MRHAS.

As yet another embodiment of this invention involves a cell line that produces a monoclonal antibody or binding fragment thereof which binds to members of a family comprising MRHAS.

As yet another embodiment of this invention involves' a cell line that produces a monoclonal antibody or binding fragment thereof which binds to an epitope shared by bacterial and viral meningitis etiologic agents, wherein said cell line is RV-1 which is deposited under American Type Tissue Collection (ATCC) accession number HB 11362.

Another embodiment of this invention is a monoclonal antibody produced by the cell line RV-1 (ATCC HE 11362).

It is also a preferred embodiment of this invention that there be a monoclonal antibody capable of reacting with a MRHAS, wherein the monoclonal antibody specifically blocks the binding of an antibody produced by a cell line that produces a monoclonal antibody or binding fragment thereof which binds to members of a family comprising MRHAS, and where such cell line can be RV-1 (vriac HB 11362).

Another embodiment involves a monoclonal antibody capable of reacting with an antigenic determinant, or homologs 'thereof, wherein the monoclonal antibody specifically blocks the binding of an antibody produced by a cell line that produces a monoclonal antibody or binding fragment thereof which binds to members of a family comprising MRHAS, and where said cell line can be RV-1 (ATCC HE 11362) and wherein said antigenic determinant is selected from the amino acid sequences presented in Table 3 (Seq ID Nos: 2, 4, 6, 9, 12, 15, 18, 21, 24, 27, 29, 31, 33, 36, and 39, respectively).

TABLE 3

| VIRUS/ BACTERIUM/ CHEMOKENE | PROTEIN | AMINO ACID REGION | AMINO ACID SEQUENCE |
|---|---|---|---|
| Rubella virus | Structural Polyprotein | 95-115 | PSRAPPQQPQPPRMQTGRGGS |
| Rubella virus | Structural Polyprotein | 82-102 | ERQESRSQTPAPKPSRAPPQQ |
| Rubella virus | Structural Polyprotein | 306-326 | DMAAPPMPPQPPRAHGQHYGH |
| Rubella virus | Structural Polyprotein | 306-326 | DMAAPPTLPQPPCAHGQHYGH |
| HIV-1 | Gag Polyprotein | 138-158 | IQGQMVHQAISPRTLNAWVKV |
| HP/-1 | Envelope Polyprotein Precursor | 648-668 | HSLIEESQNQQEKNEQELLEL |
| Haemophilus influenzae | Lipoprotein E Precursor | 92-111 | NSPYAGWQVQNNICPFDGICDWT |
| Neisseria meningitidis | Opacity-Related Protein POPM3 | 1-13 | IQPPKNLLFSSLL |
| Streptococcus pneumoniae | Pneumococcal Surface Protein A | 416-436 | EEYNRLTQQQPPICAEICPAPAP |
| Listeria monocytogenes | Protein P60 Precursor | 144-164 | AVSTPVAPTQEVICKETITQQA |
| Listeria monocytogenes | Protein P60 Precursor | 174-194 | VKQTTQATIPAPKVAETKETP |
| Listeria monocytogenes | Protein P60 Precursor | 242-262 | LAIKQTANTATPICAEVKTEAP |
| Listeria monocytogenes | Protein P60 Precursor | 285-305 | IUCETATQQQTAPICAPTEAAKP |
| Chemokine hMCP-1 | | 86-99 | SMDHLDKQTQTPKT |
| Chemoldne hMCP-3 | | 54-67 | FMKHLDICKTQTPICL |

Yet another embodiment of this invention is a monoclonal antibody capable of reacting with an antigenic determinant of the proteins presented in Table 4 (Seq ID Nos: 3, 5, 7, 10, 13, 16, 19, 22, 25, 28, 30, 32, 34, 37 and 40, respectively).

TABLE 4

| VIRUS/ BACTERIUM/ CHEMOKINE | PROTEIN | AMINO ACID REGION | AMINO ACID SEQUENCE |
|---|---|---|---|
| Rubella virus | Structural Polyprotein | 102-108 | QPQPPRM |
| Rubella virus | Structural Polyprotein | 89-95 | QTPAPICP |
| Rubella virus | Structural Polyprotein | 313-319 | PPQPPRA |
| Rubella virus | Structural Polyprotein | 313-319 | LPQPPCA |
| HIV-1 | Gag Polyprotein | 145-151 | QAISPRT |
| HIV-1 | Envelope Polyprotein Precursor | 655-661 | QNQQEICN QVQNNICP |
| Haemopbilus influenzae | Lipoprotein E Precursor | 99-105 | IQPPICN |
| Neisseria meningitidis | Opacity-Related Protein POPM3 | 1-5 | QQQPPKA PTQEVKIC |
| Streptococcus Pneumonia | Pneumococcal Surface Protein A | 423-429 | TTPAPKV NTATPKA |
| Listeria monocytogenes | Protein P60 Protein | 151-157 | QQTAPICA |
| Listeria monocytogenes | Protein P60 Protein | 181-187 | QTQTPKT |
| Listeria monocytogenes | Protein P60 Protein | 249-255 | KTQTPKL |
| Listeria monocytogenes | Protein P60 Protein | 292-298 | |
| Chemokine hMCP-1 | | 93-99 | |
| Chemokine hMCP-3 | | 61-67 | |

4. Pharmaceutical Formulations and Use

The monoclonal antibodies, peptides and pharmaceutical compositions thereof, of the present invention can be incorporated as components of pharmaceutical compositions. The composition should contain a therapeutic or prophylactic amount of at least one of the monoclonal antibodies or peptides of the present invention with a carrier that is pharmaceutically effective. Such a pharmaceutical carrier should be any compatible, non-toxic substance that is suitable to deliver the monoclonal antibodies or peptides to the patient. Such carriers can be sterile water, alcohols, fats waxes, and inert solids. The pharmaceutical composition may also be incorporate pharmaceutically acceptable adjuvants (e.g. buffering agents or dispersing agents). Hence, the monoclonal antibodies of the present invention can be employed as separately administered compositions given in conjunction with other anti-bacterial or anti-viral agents.

The monoclonal antibodies, peptides, and pharmaceutical compositions thereof, of the present. invention are particularly useful for oral or parenteral administration. It is preferred that the pharmaceutical compositions be administered parenterally: i.e., subcutaneously, intramuscularly, or intravenously. Therefore, this invention is providing compositions for parenteral administration that comprises a solution of the monoclonal antibody, peptide, or a cocktail thereof dissolved in an suitable carrier (which is preferably an aqueous carrier). Examples 9f the aqueous carriers that can be used are water, buffered water, 0.4% saline, 0.3% glycine, or the like. These solutions are to be sterile and generally free of particulate matter. Moreover, these compositions may be sterilized by conventional and well known sterilization techniques. The compositions may also contain pharmaceutically acceptable auxiliary substances. These substances are required to approximate physiological conditions such as pH adjusting and buffering agents, toxicity adjusting agents, and the like. Examples of these auxiliary substances are sodium acetate, sodium chloride, potassium chloride, calcium chloride, sodium lactate, etc. The concentration of antibody and/or peptide in these formulations can widely vary depending on its ultimate use, activity, and mode of administration of the composition. The concentration of antibody and/or peptide in these formulations will be selected primarily based on such factors as fluid volumes, viscosities, etc. It is preferable that such factors be chosen for the particular mode of administration selected. The actual methods used for preparing parenterally administrable compositions will be known or is apparent to those skilled in the art and are described in Remington's Pharmaceutical Science, 15th Ed. (Easton: Mack Publishing Company, 1980).

The monoclonal antibodies, vaccines and peptides of this invention can be lyophilized for storage and can be reconstituted in a suitable carrier prior to their use. Such techniques have been shown to be effective with conventional immunoglobulins and lyophilization and reconstitution techniques that are known in the art can be applied. It also will be appreciated by those skilled in-the art however, that lyophilization and reconstitution can lead to varying degrees of antibody activity loss (e.g., with conventional immunoglobulins, IgM antibodies tend to have greater activity loss than IgG antibodies). As such, the use levels may have to be adjusted to compensate for any possible loss of activity.

The compositions containing the present monoclonal antibodies, or vaccines or cocktails thereof can be dispensed for the prophylactic and/or therapeutic treatment of such diseases as meningitis or other maladies that may involve monocytes, monocyte-attracting chemokines or MRHAS (such as arteriosclerosis). In such therapeutic application, compositions are administered to patients who have contracted or begun to davelop a disease involving MRHAS, chemokines, or chemokine recognizing monocytes in the pathogenic mechanism. The administration of such composition is in an amount sufficient to bind the chemical signal, i.e. to the MRHAS or chemokine. For example, a composition comprising the present monoclonal antibody is administered in a therapeutic application to a patient—already infected with a meningitis etiologic agent(s)—in an amount sufficient to cure, arrest, or at least partially arrest the infection and its complications.

In prophylactic applications, compositions containing the present antibodies, vaccine or a cocktail thereof are administered to a patient not already infected by a disease-causing agent bearing an antigen that contains a MRHAS (i.e., a meningitis-causing agent), but perhaps such patient has recently been exposed to or thought to have been exposed to, or was at risk of being exposed to such agent, to enhance the patient's resistance to such potential infection or to vaccinate against such agent. The compositions containing the present peptides or cocktails thereof can be administered •not only for the prophylactic and/or therapeutic treatment of meningitis, but also possibly for arteriosclerosis, or such related disease involving monocyte-s, monocyte-attracting chemokines or MRHAS. In therapeutic application, compositions are administered to a patient who has contracted or begun to develop a disease involving MRHAS, or homologs thereof, or chemokine recognizing monocytes in the pathogenic mechanism, in an amount sufficient to block the MRHAS signal recognition by monocytes. For example, a composition containing such a peptide may be administered in a therapeutic application to a patient already infected with a meningitis etiologic agent(s), in an amount sufficient to block MRHAS recognition sites on monocytes by interfering with the ability of said agents to attract and infect monocytes (and thus interfere with the infectivity of the CNS by said agent(s).

In prophylactic applications, compositions containing one or more peptides mimicking members of the MRHAS family or a cocktail thereof are also useful as the active component of vaccines capable of inducing protective immunity against both bacterial and viral meningitis causing agents. The possible routes of administration, the antigen doses, and the number and frequency of injections will vary from individual to individual and may parallel those currently being used in providing immunity to other viral infections. For example the vaccines of the present invention are pharmaceutically acceptable compositions that contain at least one peptide of this invention, its analogues or mixtures or combinations thereof, in an amount that is effective in a mammal (including humans) treated with that composition to raise antibodies sufficient to protect such mammal from viral or bacterial meningitis for a period of time.

The vaccines of the present invention are prepared in accordance with known methods and are conveniently and conventionally combined with physiologically acceptable carrier materials, such as pharmaceutical grade saline, tetanus toxoid, and keyhole limpet hemocyanin. The vaccine compositions of the present invention may also include adjuvants or other enhancers of immune response, such as liposomes, alum preparations, or immunomodulators. Furthermore, these vaccine compositions may comprise other antigens to provide immunity against other viruses and bacteria. The amount of these other antigens is again dependent on the mammal to be treated, the type of disease, and the actual course of the disease. A single or multiple administration of the compositions can be done Nith dose levels and pattern being selected by the administering physician. However, the antigen should be present in an amount effective to raise antibodies sufficient to protect the treated mammal from that pathogen or virus for a period of time.

Furthermore, the monoclonal antibodies of the present invention may find use as a target-specific carrier molecule. Such use would involve binding an antibody to either a toxin to form an immunotoxin, or radioactive material or drug to form a radiopharmaceutical or pharmaceutical. Methods for producing immunotoxins, radiopharmaceuticals, or such pharmaceuticals are well known as set out in 1984, Cancer Treatment Reports, 68:317.

It is also possible that heteroaggregates of the monoclonal antibodies from the present invention and human T-cell activators (such as monoclonal antibodies to the CD3 antigen or to the Fc gamma receptor on T-cells) may enable human T-cells or Fc-gamma bearing cells (such as K cells or neutrophils) to kill meningitis etiologic agent infected cells via antibody dependent cell-mediated cytolysis. By way of example, such heteroaggregates may be assembled by covalently cross-linking the anti-MRHAS antibodies to the anti-CD3 antibodies using the heterobifunctional reagent Nsuccinimidyl-3-(2-pyridyldithiol)-propionate, as described by Karpowsky et al., 1984, J. Exp. bled., 160:168.

It is therefore, a preferred embodiment of this invention that there be a monoclonal antibody composition specifically reactive with an epitope selected from one the bacterial or viral sequences listed in Table 3, wherein the sequence or homolog of said sequence is within the region listed in Table 3, and wherein said monoclonal antibody is capable of blocking the infectivity of the virus or bacteria.

A further embodiment of this invention involves a monoclonal antibody composition specifically reactive with an epitope of a chemokine selected from one of the chemokine sequences listed in Table 4, wherein the sequence or homolog of said sequence is within the region listed in Table 3, and wherein said monoclonal antibody is capable of binding said chemokine in vivo to significantly reduce CNS infectivity of meningitis etiologic agents.

Yet another embodiment of this invention is a vaccine formulation comprising an immunogenic peptide comprising one or more members of the MRHAS family or an immunogenic portion thereof.

Another embodiment of this invention is a method for protecting against CNS infection of bacterial and/or viral meningitis etiologic agents by blocking a recognition site on monocytes that recognizes MRHASs.

A further embodiment of this invention is a method of treating a patient to prevent an infection due to a meningitis etiologic virus and/or bacteria, said method comprising administering a prophylactically effective amount of a composition useful in the prophylactic or therapeutic treatment of viral and/or bacterial meningitis, said composition comprising a monoclonal antibody or binding fragment thereof which binds to MRHAS shared by viral and/or bacterial meningitis etiologic agents.

Yet another embodiment of this invention is a method of treating a patient infected with a meningitis etiologic virus and/or bacteria, said method comprising administering a therapeutically effective amount of a composition useful in the prophylactic or therapeutic treatment of viral and/or bacterial meningitis, said composition comprising a monoclonal antibody or binding fragment thereof which binds to MRHAS shared by viral and/or bacterial meningitis etiologic agents.

Another embodiment of this invention entails an article of manufacture adapted for use in an immunoassay for antibodies to bacterial and/or viral meningitis etiologic agents comprising a solid support having bound thereto a peptide comprising one or more members of a group of peptides based on MRHASs, wherein said peptide having the formula a-X-b, wherein X is a sequence of at least 7 amino acids taken as a block selected from the group comprised in Table 5 below, with said block maintaining the sequence in the N terminus to C terminus direction of the native amino acid sequence and analogue thereof, said analogues resulting from conservative substitutions in or modifications to the native amino acid sequence block;
  a is selected from the group consisting of:
  (i) an amino terminus;
  (ii) one to eight amino acids taken as a block from said maintaining the sequence and N terminus to C terminus direction of that portion of the native amino acid sequence of the protein immediately N-terminal to said X or conservative substitutions in or modifications thereto; and
  (iii) a substituent effective to facilitate coupling of the peptide to another moiety; and
  b is selected from the group consisting of:
  (i) a carboxy terminus;
  (ii) one to eight amino acids taken as a block from and maintaining the sequence and N terminus to C terminus direction of that portion of the native amino acid sequence of the protein immediately C-terminal to said X or conservative substitutions in. or modifications thereto; and
  (iii) a substituent effective to facilitate coupling of the peptide to another moiety.

In certain instances, X may have as few as 6 amino acids. For example, when comparing all MRHAS sequences, it was observed that N. meningitis was an anomaly because the strain tested has a MRHAS containing 6 amino acid residues. In addition, this strain had the MRHAS sequence at the amino-terminal end of the protein. None of the other meningitis-causing organisms have the MRHAS sequence at the amino-terminal end of the protein in which they are located.

A further embodiment of. the present invention is a composition useful in the prophylactic or therapeutic treatment of viral and/or bacterial meningitis, said composition comprising peptides selected from the MRHAS family and/or the peptides described in the preceding paragraph.

One particular embodiment comprises a carrier molecule, the amino acid sequence thereof is based on the terminal 32 amino acid residues of hMCP-1 or murine JE, and containing a peptide comprising one or more members of a group of peptides based on MRHASs, wherein said peptide having the formula a-X-b, wherein X is a sequence of at least 7 amino acids taken as a block selected from the group comprised in Table 5 below, with said block maintaining the sequence in the N terminus to C terminus direction of the native amino acid sequence and analogue thereof, said analogues resulting from conservative substitutions in or modifications to the native amino acid sequence block;
  a is selected from the group consisting of: (1) an amino terminus;
  (ii) one to eight amino acids taken as a block from and maintaining the sequence and N terminus to C terminus direction of that portion of the native amino acid sequence of the protein immediately N-terminal to said X or conservative substitutions in or modifications thereto; and
  (iii) a substituent effective to facilitate coupling of the peptide to another moiety; and
  b is selected from the group consisting of:
  (i) a carboxy terminus;
  (ii) one to eight amino acids taken as a block from and maintaining the sequence and N terminus to C terminus direction of that portion of the native amino acid sequence of the protein immediately C-terminal to said X or conservative substitutions in or modifications thereto; and
  (iii) a substituent effective to facilitate coupling of the peptide to another moiety.

5. Diagnostic Uses of Monoclonal Antibodies

The monoclonal antibodies and peptides of the present invention are also useful for diagnostic purposes and can be either labeled or unlabeled. Diagnostic assays typically entail the detection of a complex formation through the binding of the monoclonal antibody to a MRHAS. When unlabeled, the antibodies can find use, for example, in agglutination assays. Moreover, unlabeled antibodies can be used in combination with other labeled antibodies (second antibodies) that are reactive with the monoclonal antibody of the present invention. An example of this is antibodies specific for immunoglobulin. Alternatively, the monoclonal antibodies can be directly labelled. A wide variety of labels may be employed, such as enzymes, enzyme substrates, enzyme cofactors, enzyme inhibitors, radionuclides, fluorescers, ligands (particularly haptens), etc. In addition, numerous types of immunoassays are available and, by way of example, some assays include those described in U.S. Pat. Nos. 3,817,827; 3,850,752; 3,901,654; 3,935,074; 3,984,533; 3,996,345; 4,034,074.

It is common for the monoclonal antibodies and peptides of the present invention to be employed in enzyme immunoassays, where for example, the subject antibodies (or second antibodies from a different species) are conjugated to an enzyme. When a biological sample containing MRHAS antigens, such as human blood serum, saliva, cerebrospinal fluid or bacterial and/or viral infected cell culture suspension, is combined with the subject antibodies, binding occurs between the antibodies and those molecules exhibiting the desired epitope. It should be noted that the biological sample may require concentration in order to detect organisms of low, titer. Such proteins, bacterial or viral particles may then be separated from any unbound reagents and a second antibody (labeled with an enzyme) added. The presence of the antibody-enzyme conjugate specifically bound to the antigen can then be determined. Other conventional techniques well known to those skilled in the art may also be used.

Kits can also be equipped with the subject monoclonal antibodies of the present invention, for detection of meningitis etiologic agents or for the presence of MRHASs. Hence, the subject monoclonal antibody compositions of the present invention May be provided, usually in a lyophilized form, either alone or in conjunction with additional antibodies specific for other epitopes of meningitis etiologic agents. The antibodies, which may be conjugated to a label, or unconjugated, are included in such kits along with buffers such as Trig, phosphate, carbonate, and the like, along with the requisite stabilizers, biocides, inert proteins (e.g., bovine serum albumin) that are standard to those skilled in the art.

It is therefore, a preferred embodiment of this invention that there be a monoclonal antibody composition specifically reactive with an epitope selected from one the bacterial or viral sequences listed in Table 3, wherein the sequence or homolog of said sequence is within the region listed in Table 3, and wherein said monoclonal antibody is capable of detecting the infectivity of the virus or bacteria. As a note, that use of the said antibodies with biological samples containing low titer meningitis etiologic agents may require concentrating said samples before the diagnostic procedure is performed.

A further embodiment involves a monoclonal antibody composition specifically reactive with an epitope selected from one of the chemokine sequences listed in Table 3, wherein the sequence or homolog of said sequence is within the region listed in Table 3, and wherein said monoclonal antibody is capable of detecting said chemokine in vivo to indicate CNS infectivity of meningitis causing agents.

Yet another embodiment of this invention entails a method of diagnosing the presence of bacterial and/or viral meningitis etiologic agents in a biological sample, said method comprising the steps of forming an antibody/antigen complex wherein the antibody portion of said complex comprises a monoclonal antibody capable of binding to both bacterial and viral meningitis etiologic agents, and detecting the presence of the antibody/antigen complex formed.

A further embodiment of this invention involves an immunoassay to detect the presence of antibodies to bacterial and/or viral meningitis etiologic agents in a biological sample comprising contacting said sample with one or more immunogenic peptide(s), where said peptide is selected from one or more members of the MRHAS family, the improvement comprising the method of screening for bacterial and/or viral meningitis etiologic agents in one test.

A further embodiment of this invention involves an immunoassay to detect the presence of antibodies to bacterial and/or viral meningitis etiologic agents in a biological sample comprising contacting said sample with 35 one or more immunogenic peptide(s), where said peptide is selected from one or more members of the MRHAS family comprising a peptide having the formula

*a*-X-*b* wherein:

X is a sequence of at least 7 amino acids taken as a block selected from the group comprised in Table 5:

TABLE 5

(i) the amino acid sequence of the Structural Polyprotein of a strain of Rubella virus that corresponds to $AA_{102}$-$AA_{108}$ of said protein of the M33 strain of Rubella virus as set forth in FIG. 1 (Seq ID No: 1);
(ii) the amino acid sequence of the Structural Polyprotein of a strain of Rubella virus that corresponds to $AA_{89}$-$AA_{95}$ of said protein of the M33 strain of Rubella virus as set forth in FIG. 1 (Seq ID No: 1);
(iii) the amino acid sequence of Structural Polyprotein of a strain of Rubella virus that corresponds to $AA_{313}$-$AA_{319}$ of said protein of the 133 strain of Rubella virus as set forth in FIG. 1 (Seq ID No: 1);
(iv) the amino acid sequence of Structural Polyprotein of a strain of Rubella virus that corresponds to $AA_{103}$-$A_{109}$ of said protein of the Therien strain of Rubella virus as set forth in FIG. 2 (Seq ID No: 8);
(v) the amino acid sequence of Structural Polyprotein of a strain of Rubella virus that corresponds to $AA_{90}$-$AA_{96}$ of said protein of the Therien strain of Rubella virus as set forth in FIG. 2 (Seq ID No: 8);
(vi) the amino acid sequence of Structural Polyprotein corresponds of a strain to $AA_{314}$-$AA_{320}$ of Rubella virus that of said protein of the Therien strain of Rubella virus as set forth in FIG. 2 (Seq ID No: 8);
(vii) the amino acid sequence of the Gag Polyprotein of an isolate of the HIV-1 that corresponds to $A_{145}$-$A_{151}$ of the Gag Polyprotein of the LV isolate of HIV-1 as set forth in FIG. 3 (Seq ID No: 11);
(viii) the amino acid sequence of the Envelope Polyprotein Precursor of an isolate of the HIV-1 that corresponds to $AA_{655}$-$AA_{661}$ of the Envelope Polyprotein Precursor of the LAV-la isolate of HIV-1 as set forth in FIG. 4 (Seq ID No: 14);
(ix) the amino acid sequence that corresponds to $AA_{99}$-$AA_{105}$ of the Lipoprotein E Precursor of *Haemophilus influenzae* as set forth in FIG. 5 (Seq ID No: 17);
(x) the amino acid sequence that corresponds to $A_1$-$A_5$ of the Opacity-Related protein POPM3 of *Neissera meningitidis* as set forth in FIG. 6 (Seq ID No: 20);
(xi) the amino acid sequence that corresponds to $AA_{423}$ to $AA_{429}$ of the Pneumococcal Surface Protein A of *Streptococcus pneumoniae* as set forth in FIG. 7 (Seq ID No: 7);
(xii) the amino acid sequence that corresponds to $A_{151}$-$AA_{157}$ of the Protein P60 Precurzor of *Listeria monocytogenes* as set forth in FIG. 8 (Seq ID No: 26);
(xiii) the amino acid sequence that corresponds to $AA_{181}$-$AA_{187}$ of the Protein P60 Precursor of *Listeria monocytogenes* as set forth in FIG. 8 (Seq ID No: 26);
(xiv) the amino acid sequence that corresponds to $AA_{249}$-$AA_{255}$ of the Protein P60 Precursor of *Listeria monocytogenes* as set forth in FIG. 8 (Seq ID No: 26);
(xv) from the amino acid sequence that corresponds to $AA_{292}$-$AA_{298}$ of the Protein P60 Precursor of *Listeria monocytogenes* as set forth in FIG. 8 (Seq ID No: 26);
(xvi) from the amino acid sequence of a variant of the chemokine human Monocyte Chemoattractant Protein hMCP-1, that corresponds to $AA_{93}$-$AA_{99}$ of hMCP-1 as set forth in FIG. 9 (Seq ID No: 35);

TABLE 5-continued (xvii) from the amino acid sequence of the chemokine hMCP-3, that corresponds to $AA_{61}$-$AA_{67}$ of hMCP-3 as set forth in FIG. 10 (Seq ID No: 38);
(xviii) from any amino acid sequence present within a protein that is homologous to members of the MRHAS family;

with said block maintaining the sequence in the N terminus to C terminus direction. of the native amino acid sequence and analogue thereof, said analogues resulting from conservative substitutions in or modifications to the native amino acid sequence block;

a is selected from the group consisting of:
(i) an amino terminus;
(ii) one to eight amino acids taken as a block from and maintaining the sequence and N terminus to C terminus direction of that portion of the native amino acid sequence of the protein immediately N-terminal to said X or conservative substitutions in or modifications thereto; and
(iii) a substituent effective to facilitate coupling of the peptide to another moiety; and b is selected from the Group consisting of:
(i) a carboxy terminus;
(ii) one to eight amino acids taken as a block from and maintaining, the sequence and N terminus to C terminus direction of that portion of the native amino acid sequence of the protein immediately C-terminal to said X or conservative substitutions in or modifications thereto; and
(iii) a substituent effective to facilitate coupling of the peptide to another moiety, the improvement comprising the method of screening for bacterial and/or viral meningitis etiologic agents in one test.

Yet a further embodiment of the present invention is a method for analyzing a sample of a biological fluid with regard to the presence of anti-X antibodies therein, where X is selected from one or more members of the group comprising:

(i) Rubella virus;
(ii) HIV-1;
(iii) *Haemophilus influenzae;*
(iv) *Nisseria meningiticUs;*
(v) *Streptococcus pneumoniae;*
(vi) *Listeria monocytocenes*, and comprising the steps of:

A) providing a solid support having bound thereto a peptide selected from one or more members of the MRHAS family, or said peptide is selected from one or more members of the MRHAS family comprising a peptide having the formula a-X-b wherein:

X is a sequence of at least 7 amino acids taken as a block selected from the group comprised in Table 5, and with said block maintaining the sequence in the N terminus to C terminus direction of the native amino acid sequence and analogue thereof, said analogues resulting from conservative substitutions in or modifications to the native amino acid sequence block; a is selected from the group consisting of:
(i) an amino terminus;
(ii) one to eight amino acids taken as a block from and maintaining the sequence and N terminus to C terminus direction of that portion of the native amino acid sequence of the protein immediately N-terminal to said X or conservative substitutions in or modifications thereto; and
(iii) a substituent effective to facilitate coupling of the peptide to another moiety; and b is selected from the group consisting of:
(i) a carboxy terminus;
(ii) one to eight amino acids taken as a block from and maintaining the sequence and N terminus to C terminus direction of that portion of the native amino acid sequence of the protein immediately C-terminal to said X or conservative substitutions in or modifications thereto; and
(iii) a substituent effective to facilitate 15 coupling of the peptide to another moiety, B) contacting said solid support with said human sample to provide a sample-contacted support;
C) washing said sample-contacted support to provide a washed support; and
D) determining whether human antibodies are bound to said support.

6. Preparation and Use of Synthetic Peptides

Novel peptides are provided in the present invention which immunologically mimic protein epitopes encoded by infectious agents that cause meningitis and by monocyte-attracting chemokines. To accommodate variations among different infectious agents, adjustments for conservative substitutions, and selection among the alternatives where non-conservative substitutions are involved, maybe made. There are many uses for these peptides which include, for example, use as: immunogens for a vaccine; blockers of MRHAS recognition sites on monocytes, interfering with the ability of meningitis etiologic agents to attract and infect monocytes and thereby block access of the infectious agent to the CNS; blockers of MRHAS recognition sites on monocytes involved in plaque build-up that occurs during atherosclerosis; and as antigens in diagnostic kits to detect antibodies in biological fluid as indication of infection by meniningitis etiologic agents. Depending upon the nature of the protocol, the peptides may be conjugated to a carrier or other compounds, unlabeled or labeled, bound to a solid surface, or the like. Preferably, the peptides are. chemically synthesized by methods well known in the art. See E. Ahterton and R. C. Sheppard, SOLID PRASE PEPTIDE SYNTHESIS: A PRACTICAL APPROACH, IRL Press, Oxford (1989).

Embodiments of the present invention include peptides of interest derived from MRHAS family members listed in Table 1. Further embodiments include peptides of interest derived from MRHAS family members and their parent monocyte-attracting chemokines listed in Table 2. Other possible embodiments include MRHAS family members found on proteins listed in Table 3.

The peptides of interest will include at least five, sometimes six, sometimes seven, sometimes eight, sometimes 15, sometimes 21, usually fewer than about 50 and preferably fewer than about 25 amino acids included within a sequence homologous to a member of the MRHAS family. It is desired that a given peptide be as small as possible while still maintaining all of the immunoreactivity or monocyte attracting activity of the larger corresponding peptide. Furthermore, it may be desirable in some instances to join two or more oligopeptides which are non-overlapping to form a single peptide structure or to use them as individual peptides at the same time, which separately or together provide equivalent sensitivity to the parent.

A given peptide may be modified by introducing conservative or non-conservative substitutions in the peptide, usually fewer than 50 number percent, and more 35 usually fewer than 30 number percent, more usually with fewer than 15 number percent of the amino acids being exchanged (Waterman, 1986, Nucleic Acids Res., 14:9095; Hitachi, HIBIO MacDNASIS Pro: DNA and Protein Sequence Analysis Software System Reference Manual). In those situations where amino acid regions are found to be polymorphic, it may be desirable to vary one or more particular amino acids to more effectively mimic the differing epitopes of the different meningitis etiologic infectious agents, or monocyte attracting chemokines.

It is important that it be understood that the. polypeptide employed in the present invention need not be identical to any particular MRHAS family member, so long as the subject peptide is able to provide for immunological competition with proteins of at least one of the members of the MRHAS family and/or demonstrate monocyte recognition and/or attracting activity. Therefore, the subject peptide may be subject to various changes, such as substitutions, insertions, and deletions, either conservative or nonconservative, where such chances may provide for certain advantages in their use.

It is also important to point out that one, two, or more amino acids may be added to the termini, an oligopeptide, or peptide to provide for ease of linking peptides one to another, for coupling to a support, or larger peptide and for reasons to be discussed subsequently,' for modifying the physical or chemical properties of the peptide or oligopeptide, or the like.

In the present invention, the term amino acid is used to include, but not limited to, all natural occurring amino acids and all synthetic or non-natural amino acids such as homocysteine. The term 'amino acids selected as a block' (or other similar statements) means a linear sequence of a set number of amino acids that taken together form a group. The term 'antigenic determinant' means the structural component of an antigen molecule responsible for its specific interaction, with antibody molecules elicited by the same or related antigen as defined by Dorland's Pocket Medical Dictionary 23 ed., (Philadelphia: Saunders, 1982) at 198; Morris, ed., Academic Press Dictionary of Science and Technology (San Diego: Academic Press, 1992).

A given peptide or oligopeptide sequence may differ from the natural sequence by that sequence being modified by terminal —NH2 acylation (e.g., by acetylation, or• thioglycolic acid amidation, terminalcarboxy amidation, e.g., with ammonia or methylamine) to provide stability, increased hydrophobicity for linking or binding to a support or either molecule, or for purposes of polymerization.

Of particular interest to the present invention is the use of the mercaptan group of cysteines or thioglycolic acids used for acylating terminal amino groups, of the like, for linking two of the peptides or oligopeptides or combinations thereof by a disulfide linkage or a longer linkage to form polymers that contain a number of MRHAS epitopes, Such polymers have the advantage of increased immunological reaction. Furthermore, where different peptides are used to make up the polymer, they possess the additional ability to induce antibodies that immunoreact with several antigenic determinants of the different meningitis etiologic agents.

In order to achieve the formation of antigenic polymers (i.e., synthetic multimers), compounds may be utilized having bishaloacetyl groups, nitroarylhalides, or the like, where the reagents being specific for this groups. Therefore, the link between two mercapto groups of the different peptides or oligopeptides may be a single bond or may be composed of a linking group of at least two, typically at least four, and not more than about 16, but usually not more than about 14 carbon atoms.

To prepare the novel peptides of the present invention, any of the conventional peptides production techniques may be employed. These techniques include synthesis, recombinant DNA technology and combinations thereof. The peptides may be synthesized in solution or on a solid support in accordance with conventional techniques. A variety of automatic synthesizers are commercially available and can be used in accordance with known protocols. For example, see Stewart & Young, 1984, Solid Phase Peptide Synthesis, 2nd ed., Pierce Chemical Co.; Tam et al., 1983, J. Am. Chem. Soc., 105:6442. Recombinant DNA technology may be utilized where a synthetic gene may be prepared by employing single strands which code for the given MRHAS. polypeptide or substantially complementary strands thereof, where the single strands overlap and can be brought together in an annealing medium so as to hybridize. The hybridized strands may then be ligated to form the complete gene, and, by choice of appropriate termini, the gene may be inserted into expression vectors, which are readily, available today. For example, see Maniatis et al., 1982, Molecular Cloning, A Laboratory Manual, Cold Spring Harbor Laboratory. In the alternative, the region of the genome coding for the given MRHAS peptide may be cloned by conventional recombinant DNA techniques and expressed (See Maniatis, infra).

EXAMPLE 1

Generation and Characterization of Monoclonal Antibodies

Example I describes the method for the generation of hybridoma cell lines that produce monoclonal antibodies with a specificity for MRHAS. This method involves the use of purified Rubella virus as the immunogen. The protocols for the generation of the hybridoma cell lines that produce the said monoclonal antibody and the characterization of the antibodies were as follows.

Rubella virus, strain M33, was obtained as the first passage after primary isolation. The RV strain was obtained from the laboratories of the Vancouver, British Columbia, Canada Public Health Laboratory. Murine fibroblasts (L cells), used to generate stock virus, were maintained in monolayer cultures and were routinely propagated at 37° C. With minimal Eagle's medium (MEM supplemented with 5% fetal calf serum (FCS, Grand Island Biological Company, GIBCO), 10011 g/ml streptomycin, and 100 IU/ml penicillin. Stock virus was routinely prepared by inoculating semiconfluent monolayers of L cells with RV at a multiplicity of infection (m.o.i.) of 0.01. After adsorption at 34° C. in a humid atmosphere containing 5% CO2 for 1 hour, additional medium was added and the flask was incubated at 34° C. for 6 days, at which time the culture supernatant was collected and frozen at –80° C.

Virus purification was accomplished as follows. L cell monolayers were infected at an m.o.i. of 0.01 and incubated at 34° C. for 6 days as described. The culture supernatants were collected and centrifuged at 3000×g for 20 min. All procedures were carried out at 4° C. unless otherwise stated. The supernatant obtained was recentrifugated at 100,000×g for 3 hours and the resulting pellet was resuspended in 0.2 ml TNE buffer (0.15 M NaCl, 50 Mm Tris-HCl, and 1 mM EDTA, pH 7.8), This sample was layered onto a 16 ml 25-45% discontinuous Renografin-60 (Reno M-60, Diatrisoate Meglumine, 60%, Squibb) gradient prepared with TNE buffer and centrifuged in an SW 27 Rotor at 55,000×g for 2 hours. The single, sharp band at the interface was collected, pelleted as described previously, resuspended in 0.5 ml TNM buffer (0.15 M NaCl, 50 mM Tris-HCl, 1 mM MgCl2, pH 7.8), and layered on a 12 ml 30-45% continuous Renografin gradient prepared with TNM buffer. After centrifugation at 200,000×g for 3 hours, 0.5 ml fractions were collected. An aliquot was removed from each fraction for ELISA and infectivity tests (both described below). Appropriate fractions were then pooled, diluted with TNM buffer, and centrifuged at 100,000×g for 3 hours to remove the Renographin. Rubella antigen, prepared in this way, was used to immunize mice for the construction of hybridomas.

The ELISA was performed according to the procedure described by Voller in Rose & Freidman, eds., 1976, Manual of Clinical Immunology, 506-512. Viral samples were diluted into coating buffer and duplicate 200 Al aliquots were adsorbed to microtiter plate wells (Cooke Laboratory Products, Dynatech Laboratories Inc., Alexandria, Va.). After coating, a predetermined 1/16 dilution of human anti-Rubella antiserum (HI titer=1/128) was added to each well. Antibody binding was measured using a previously determined 1/2,000 dilution of rabbit antihuman IgG (Flow Laboratories) linked to alkaline phosphatase. The A400. was determined after 30 minutes incubation at room temperature.

The infectivity test is a technique used to titer RV and was based on the ability of RV-infected cells to adsorb erythrocytes. It employs, in principle, the procedure of Hotchin et al., 1960, Virology, 10:275-280 for measuring the infectivity of noncytopathic viruses. Serial doubling dilutions of RV suspensions were used to infect confluent monolayers of L2 cells grown in tissue culture chamber slides (Lab Tek Products, Division of Miles Laboratories, Inc., Illinois). Two-chamber slides were used. Each chamber received a 50 pl aliquot of the appropriate RV dilution. Virus was allowed to adsorb for 1 hour at 34° C. and 2.5 ml of medium and 50 pa of a 20% suspension of heparinized sheep erythrocytes in Alserver's solution were added directly to each chamber. The slides were then incubated for 24 hours at 34° C. The chambers were removed and each slide was washed gently by immersion if pH 7.4 Dulbecco phosphate-buffered saline (PBS) at room temperature and examined microscopically for hemadsorbing cells. Uninfected control monolayers were treated in an identical fashion.

Mice were immunized using the following procedure. A Balb/c mouse was inoculated intraperitoneally (IP) with 250 pg of M. tuberculosis and 15 pg. of purified RV 30 suspended in 45% Renograf in. Approximately 4 weeks later, 4 booster doses of 10 pg of virus each were given intravenously at day minus 5, minus 4, minus 3 and minus 2, prior to fusion. The final boost was accompanied by an additional injection of the same dose IV. Serum was taken from the immunized mouse throughout to monitor antibody production against RV proteins.

A Balb/c mouse was immunized as previously described and one day after the final booster doses of Purified virus, the mouse was sacrificed and a suspension of spleen cells was prepared and fused with myeloma cells (P3X63Ag8) in a ratio of 5.1 using 50% polyethylene glycol according to the procedure described by Koprowski et al., 1977, Proc. Natl. Acad. Sci., 74:2985-298. Cultures containing 1×105 cells in 100 Al were established in 96-2311 Linbro plastic plates (Flow. Laboratories, McLean, Va., USA) where each well contained a feeder layer of 4×103 murine peritoneal exudate cells (macrophages). Colonies appeared in 2 to 3 weeks and culture medium in appropriate well were screened for anti-Rubella antibody in the ELISA, employing infected and uninfected L cell lysates as antigen. Cells that were producing antibody were subcloned and retested.

ELISA screening of clones was performed according to the procedure described by Vpller, infra, as previously described. Infected L cell monolayers were detached by scraping, sonicated and diluted in coating buffer to give a final protein concentration of 100 Ag protein/100 Al of lysate. Each microwell was coated with 200 Al of lysate. After coating overnight at 4° C., 100 Al of each test supernatant was added. After a 90 minute incubation at 37° C., and washing, 100 it of rabbit anti-mouse IgG, linked to alkaline phosphatase (Flow Laboratories) was added, and the plate was reincubated for one hour at 37° C. After addition of 100 μl of a 10% diethanolamine solution (pH 9.8), containing 1 mg/ml p-nitrophenylphosphate (Sigma), the plate was incubated for one hour at 37° C. and the $A_{400\ nm}$ was determined as before.

The immunoglobulin class of anti-Rubella virus antibodies produced by the positive clones was determined by testing the supernatant from such clones against affinity purified anti-mouse immunoglobulin (South Biotech), using the ELISA methods.

Polyacrylamide slab gel electrophoresis (PAGE) of Rubella virus, proteins was performed according to Laemmli, 1970, Nature, 227:680-685. RV polypeptides in sample buffer (0.062 M Tris-HCl, pH 6.8) containing 2% SDS, 1% 0/116 glycerol, 0.5% (w/v) bromophenol blue and 1% 2-mercaptoethanol were placed in a boiling water bath for 2 minutes prior to electrophoresis at 25 mA for 2 hours on a 10% discontinuous acrylamide slab gel system. Aliquots of 15 Al containing 5 Ag protein were applied to each gel lane. Protein standards used for gel calibration were as follows: bovine serum albumin (66200), ovalbumin (45,000), carbonic anhydrase (28,000), soybean trypsin inhibitor (20,100), and alpha-lactalbumin (14,200) (Bio-Rad). Gels were stained with silver according to the procedure described by Wray et al., 1981, Analyt. Biochem., 118:197203.

Rubella virus proteins separated by PAGE were transferred electrophoretically from the SDS-PAGE gel to nitrocellulose paper (Bio-Rad) by the method described by Towbin et al., 1979, 15roc. Nat. Aced. Sci., 76:4350-4354. A constant current of 35 mA was applied to the gel-nitrocellulose paper sandwich for 1 hour, in an electroblot buffer of 25 mM Tris-HCl, 192 mM glycine and 20% (1,11) methanol at pH 8.3. The proteins transferred onto the blot were either stained with amino black or detected by enzyme immunoassay. The latter was performed by soaking the paper in PBS containing 1% milk for 30 minutes in order to clock non-specific protein binding sites. The paper was then incubated with monoclonal antibody at 37° C. for 1 hour., washed 3 times with PBS followed by an hour incubation at 37° C. with peroxidase-conjugated goat anti-mouse immunoglobulin (Cappel, Cochranville, Pa.) diluted 1/1000 in PBS containing 3% BSA. After 3 additional washes, the blots were soaked in a solution of Odianisidine prepared as described by Towbin, infra.

One fusion yielded 268 clones. After initial screening, 12 (4.5%) of the 266 clones were positive against infected cell lysates. The 12 clones were recloned and only 4 of these remained stable antibody producers. The 4 clones as listed in Table 6 were designed RV1-RV4 and further characterized according to Ig class and molecular weight of the antigen recognized.

TABLE 6

Summary of Mab characteristics of 4 stable hybridoma clones obtained

| Original Clone | Cell line Designation | Immuno-globulin Class/subclass | A 410 nm | Molecular weight of antigen recognized (Kd) |
|---|---|---|---|---|
| 101 BI | RV1 | IgG1 | 0.248 | p30, gp45-48 |
| 201 A5 | RV2 | IgG2A | 0.126 | p30, gp45-48 |

TABLE 6-continued Summary of Mab characteristics of 4 stable hybridoma clones obtained

| Original Clone | Cell line Designation | Immunoglobulin Class/subclass | A 410 nm | Molecular weight of antigen recognized (Kd) |
|---|---|---|---|---|
| 6C6 | RV3 | IgG2B | 0.241 | p30, gp45-48 |
| 1A1 | RV4 | IgG3 | 0.174 | p30, gp45-48 |

The first band to appear on immunoblotting was consistently the p30 core protein. However, a second band was observed at approximately 40,000 Kd and was clear after 30 minutes incubation. The larger 40 Kd protein has been designated E2 and has been shown to have a molecular weight of 35-38 Kd (vaccine strain and wild type 349). The E2 membrane protein is glycosylated and is detected in mature virions as a protein with a molecular weight of approximately 40,000-43,000 daltons. These results are summarized in FIG. 11.

The four hybridomas were isolated from a single fusion, but can be seen to be independent isolates from the differences observed in the immunoglobulin class determinations. In spite of their obvious differences, the clones were all directed against the same (cross-reacting) epitopes which appears to be on the RV core protein having a molecular weight of approximately 30,000. (Sal T.16 NY-3)

A comparison of nucleotide sequences for the p30 core (Seq ID No: 3) and p35-38 E2 (Seq ID No: 7) Sequences contained in the 24S subgenomic messenger RNA of RV (Zheng, 1989, infra) in Table 7 revealed that one core sequence was homologous with one E2 sequence as follows:

TABLE 7

| COMPARISON OF SEQUENCE HOMOLOGIES BETWEEN p30 AND p38 IN THE RUBELLA VIRUS GENOME | | |
|---|---|---|
| ORIGIN | AMINO ACID POSITION | SEQUENCE |
| RV (p30) core | 102 | Q-P-Q-P-P-R-M |
| RV (E2) membrane | 313 | P-P-Q-P-P-R-A |

In view of the core/outer membrane cross-reactivity of the RV monoclonal antibodies, it was certain that these antibodies would detect the presence of both p30 core and E2 membrane proteins, thereby limiting their use in any diagnostic system which would attempt to define the status of RV invention in the CNS as permissive, or non-permissive, for growth.

However, the significance of the external placement of the internal core sequence in the membrane-associated E2 protein represents an important viral strategy as noted the amino acid changes in the E2 protein of several alpha-viruses have been founa in Sindbis Virus (Davis et al., 1986, Proc. Natl. Acad. Sci., 83: 6771-6775), Ross River virus (Faragher et al., 1988, Virology, 163:509-526) and Venezuelan equine encephalitis virus (Johnson et al., 1986, T. Gne. Viral., 67:1951-1960), to be implicated in the modulation of viral virulence.

EXAMPLE 2

The Use of RV1 Mab to Detect and Define Homologous Meningitis-Specific Antigenic Sequences In the course of RVI Mab Characterization, it was observed that the RVI Mab cross-reacted with bacterial antigens in *N. meningitidis, S. pneumoniae, H. influenzae, L. monocytogenes* as well as antigens in HIV-1. Immunoblots-were performed as previously described using bacterial antigens and HIV-1 antigens and RV-1 Mab.

The bacterial strains were obtained from the American Type Culture Collection (ATCC), Washington, D.C. (*Neisseria meningitidis* and *Streptococcus pneumoniae*) and from the Caribbean Epidemiology Centre (CAREC), Port of Spain, Trinidad (*Streptococcus pneumoniae*). All strains were grown on chocolate agar overnight at 37° C. in an atmosphere containing 5% CO2, Cultures were stored in brain heart infusion broth containing 20% glycerol at −70° C.

Antigens present in the outer membrane protein fraction of *Neisseria meningitidis* were prepared using lithium chloride as previously described by Johnston et al., 1976, J. Exp. Med., 143: 741-758. Whole cells were suspended in lithium chloride buffer (200 mM lithium chloride, 100 mM lithium acetate, 10 mM EDTA, pH 6.0), transferred to a 250 ml erlenmeyer flask containing 3-5 mm glass beads and shaken at 300 rpm in a G24 Environmental incubator shaker for 2 hours at 45° C. The suspension was centrifuged at 8,000 rpm for 20 minutes using a Sorvall SS034 fixed angle rotor with R max=10.70 cm. Collected-supernatant was transferred to a rigid wall polycarbonate tube and centrifuged at 35,000 rpm for 2 hr at 10° C. using, a 50.2 Beckman rotor. The supernatant was discarded and pellet resuspended in a 1 ml of phosphate buffered saline (PBS). The protein content was determined by the Lowry method.

Sonicated antigen preparations of *S. pneumoniae* and *H. influenzae* were prepared using the following procedure. Approximately 10" bacterial were suspended in 5 ml PBS and heat-killed for 20 min at 56° C. Using a Branson 350 Sonifier Cell disrupter (Branson Cleaning Equipment Co.) cells were sonicated 3 times, with a 50% pulse setting, for 5 minutes each time. The sample was kept at 4° C. with ice throughout. The suspensions were then centrifuged for 20 min at 25,000 rpm, using a Beckman 70 Ti.1 rotor at 10° C. The protein concentration of the resulting supernatant was determined using the Lowrey protein assay.

HIV-1 antigen was purchased from ABI (Advanced Biotechnologies, Inc., Columbia, Md.). Antigen was contained in viral lysate with specifications given in catalog number 10-119000 with Lot number 54-040 containing a particle count of 1.09×1010 vp/ml active virus. The preparation was treated with Triton X-100 added to a final concentration of 1%, and heated to 56° C. for one hour with mixing. The final protein concentration of lysate was 0.78 mg/ml. Each lane or PAGE contained 10 pg of antigen.

PAGE was carried out as previously described using 15 μl samples of bacterial antigen, containing 5 μg protein per well. Immunoblots were performed on the transferred antigens using RVI Mab in tissue culture supernatants as previously described.

The results of immunoblots of bacterial antigen using RV1 Mab are contained in FIG. 12. The RV Mab clearly detected crossreacting epitopes in *N. meningitidis, H. influenzae, S. pneumoniae* and protease k treatment eliminated all of these bands, indicating that the antigens detected with the RV Mab are protein in nature. Control Streptococcus A and *M. tuberculosis* (p60) antigen preparations were negative using the RV1 Mab.

The results of immunoblots of HIV antigens using RV1 Mab are contained in FIG. 13. The RV1 Mab clearly detected two membrane protein antigens indicating that HIV employs a strategy identical to that of RV which places a portion of the inner core protein on the outside of the virion.

Since the likely sequences of the corresponding RV1 Mab antigens are QPQPPRM (Seq ID No:3) and PPQPIDA (Seq ID No:7) in the core and E2 proteins, respectively, a search was undertaken to find similar, crossreacting sequences in the available bacterial and HIV sequences. The search results the data are presented in TABLE 4.

FIG. 12 illustrates a cross-reactivity, with the RV1 Mab detecting a major band of approximately 26-28,000 daltons and 2 minor bands at approximately 45,000 daltons. An outer membrane protein with a molecular weight of about 28,000, expressed on the cell surface, and existing as a lipoprotein in association with the outer membrane-cell wall complex of *H. influenzae* has been identified and designated Protein E. It is capable of eliciting a bactericidal immune response against non-typable *H. influenzae* and is highly conserved among *H. influenzae* strains: Protein E has been sequenced and the sequences listed in Table 4 are closely homologous to the membrane and core sequences of RV shown in that table.

FIG. 12 also illustrates that the RV1 Mab detected one band at approximately 60,000 daltons with *L. monocytogenes*. All virulent *L. monocytogenes* stains secrete as SH-activated cytolysin called listeriolysin (Kuhn & Goebel, 1988, Infect. Immun. 56:79-82). This protein, termed p60, is an essential virulence factor as nonhemolytic mutants have reduced rates of survival in the mouse infection model (Gaillard, et al., 1986, Infect. Immun. 52:50-55) and in mouse peritoneal macrophages. The sequence of the p60 has been determined (Kohler, et al., 1990, Infec. Immun. 58:1943-1950) and the sequences identified at the positions listed in Table 4 are closely homologous to the RV core and membrane sequence.

Finally, FIG. 13 illustrates that the RV Mab detected two bands at approximately 24,000 (p24) and 61,000 (p61) daltons. The p24 has been shown to be a major core protein and p61a transmembrane protein in the HIV virion, and the complete nucleotide sequence of the HIV1 genome is available (Ratner et al., 1985, Nature 313:277-280). A number of septapeptide sequences were identified which are closely homologous to the RV core and membrane sequences, and these sequences are.listed in Table 4.

EXAMPLE 3

Immunologic Properties of a Peptide Mimicking Antigenic Determinants Corresponding to the *Streptococcus* pneumoniae MRHAS Sequence A polypeptide vaccine was synthesized comprising the MRHAS sequence found in *S. pneumoniae* and 32 amino acid residues found at the C-terminal end of murine MCP-1 (JE).

The polypeptide has the amino acid sequence KEAVVFVT KLKREVCADPKKEWVQTYIKNLDR-QQQPPKA. This 39 amino acid peptide is referred to herein as $JE_{12}$-QQQPPKA (Seq ID No:75). The dose-response of this peptide antigen was tested in mice along with the specificity of the antibody produced in the two tests described as follows. The overview of this analysis entails immunization of the mice four times, at two week intervals. At the fifth week, one week after the third immunization, sera was collected to determine whether any antibody was made, and if so, its specificity. The seventh week, one week after the fourth immunization, sera was collected to determine antibody specificity.

The $JE_{32}$-QQQPPKA (Seq ID No:75) peptide vaccine was prepared by AnaSpec Inc., San Jose, Calif. The peptide chemokines, hMCP-1 and hMCP-2, were purchased from PeproTech Inc., Rocky Hill, N. J. The adjuvant system (MPL+TDM) was purchased from Sigma Immunochemicals, St. Louis, Mo.

The Enzyme-Linked Immunosorbent Assay (ELISA) was performed according to the procedure described previously (Voller, A., et al. 1976, in Manual of Clinical Immunology, Rose, N. R. and Friedman, H., eds., Chapter 69, American Society for Microbiology, pp. 506-512). 20Each microwell was coated with 1.0 Ag of antigen in a 0.05 M carbonate buffer at pH 9.6 and incubated overnight at room temperature to absorb the antigen. The plate was then washed with PBS containing 0.02% PBS-Tween. Each well then received 100 AL of PBS containing 0.5% bovine serum albumin and the plate was washed 3 times with PBS TWEEN. Each well then received 100 AL of antibody, incubated for one hour at 37° C., and then washed 3 times with PBS-Tween. This was followed by the addition of 100 L of alkaline phosphatase-conjugated goat anti-mouse immunoglobulins (BLR) diluted 1:3,000 in PBS containing 3% BSA. The plate was then incubated for 1 hour at 37° C. and then washed 3 times with BBS-Tween. Each well then received 100 µl of a 10% diethanolamine solution (pH 9.8), containing 1 mg/ml p-nitrophenyl-phosphate (Sigma). The plate was then incubated at room temperature for 30 minutes and the absorbance was then determined spectrophotometrically using a Dynatech microplate reader MR600 at 410 nm.

The Outer Membrane Proteins (OMP) were extracted from *N. meningitidis* and prepared as described herein following method of Johnston et al. (1976, J. Esp. Med. 143:741-758). Briefly, whole cells were suspended in lithium chloride buffer (200 s mM lithium chloride, 100 mM lithium acetate, 10 mM EDTA, pH 6.0), transferred to a 250 ma erlenmeyer flask containing 3-5 mm glass beads and shaken 300 rpm in a G24 Environmental incubator, shaker for 2 hr. at 45° C. The suspension was centrifuged at 8,000 rpm for 20 minutes ‘using a Sorvall SS-34 fixed angle rotor with Rmax=10.70 cm. Collected supernatant was transferred to a rigid wall polycarbonate tube and ultracentrigured at 35.0 K (35,000 rpm) for 2 hours at 10° C. using a 50.2 Ti rotor (Beckman). Supernatant was discarded and the pellet was, resuspended in 1 ml of PBS. Protein content was determined by the method described by Lowry et al., (1951, J. Biol. Chem. 193:265-278).

Antigen was dissolved in saline and added to adjuvant prewarmed to 40° C. The preparation was vortexed for 2 to 3 minutes to form the emulsion. Each mouse received a 200 µL dose containing 100 µg, 50 µg, or 25 µg of antigen intraperitoneally. Each mouse received 4 injections, spaced at 2 week intervals. The mice were bled one week after the 4th injection. Adjuvant (MPL+TDM) was used throughout. Control groups received adjuvant alone, with no antigen. Each group was comprised of 4 animals each.

The monoclonal antibody and accompanying hybridoma is available from the American Type Culture Collection under accession number ATCC HB 11431. The Mab is specific to *N. meningitidis* and is herein referred to as Nm-2.

Experiments were performed to determine if antibody would be made by mice immunized with the substituted murine antigen, murine $MCP_{32}$-QQPPKA ($JE_{32}$-QQQPPKA) (Seq ID No:75) Elisa tests were performed on the first pre-bleed from mice after the second boost. In order to determine the specificity of any polyclonal antiserum made, comparisons were made between:

(a) polyclonal antibody vs. $JE_{32}$-QQQPPKA (Seq ID No:75)

(b) polyclonal antibody vs. OMP from *N. meningitidis*

(c) Nm-2 antibody vs. $JE_{32}$-QQQPPKA (Seq ID No:75)

(d) Nm-2 vs. OMP from *N. meningitidis*

(e) polyclonal antibody vs. hMCP-1 (control).

Sera from all injected mice were pooled and used to perform ELISA tests.

The results are shown in Table 8 and demonstrate that the polyclonal antibody (Ab) detects the antigen, murine $JE_{32}$-QQQPPKA (Seq ID No:75) nize the mice. The antibody i<also detects a cross-reacting antigen in the OMP from *N. meningitidis*, another meningitidis etiologic agent. However, the polyclonal antibody does not detect an identical concentration of the human chemokine, hMCP-1, a very close analogue to the JE-MCP. Moreover, the highly specific Nm-2 monoclonal antibody detects the *N. meningitidis* antigen in the gimp preparation, but does not detect the murine $JE_{32}$-QQQPPKA (Seq ID No:75)

These results show that since the $JE_{32}$-QQQPPKA (Seq ID No:75) antigen produces antibody that is less specific than the monoclonal antibody, it will provide a vaccine for more than one meningitis-causing organism with one immunization and is therefore a universal immunization.

TABLE 8

| polyclonal serum dilution | Antigen: OMP | | | | |
|---|---|---|---|---|---|
| | Antibody: | | | | |
| | Nm2 | polyclonal | $JE_{32}$-QQQPPKA (Seq ID No: 75) Nm2 | polyclonal | polyclonal |
| 20× | 1.042 | 1.007 | 0.009 | 1.398 | 0.101 |
| 40× | 1.136 | 1.029 | 0.025 | 1.377 | 0.113 |
| 80× | 1.179 | 0.972 | 0.008 | 1.375 | 0.0986 |
| 160× | 1.154 | 1.151 | 0.002 | 1.368 | 0.0988 |
| 320× | 1.168 | 1.151 | 0.001 | 1.401 | 0.0975 |
| 640× | 1.186 | 1.155 | 0.004 | 1.327 | |
| 1280× | 1.120 | 1.157 | −0.002 | 1.274 | |
| 2560× | 1.190 | 1.180 | −0.003 | 1.097 | |
| 5120× | 1.160 | 1.134 | −0.004 | 0.829 | |

The OMP, considered a vaccine for Meningitis, generated the Mab Nm-2 as discussed above. This Mab binds its OMP antigen but not the JE-MRHAS. It is therefore, considered a specific Mab. In contrast, the polyclonal Ab generated with the JE-MRHAS antigen binds to both its native antigen and OMP. Since OMP is considered a vaccine that gives rise to a very specific Mab, and JE-MRAHS gives rise to a less specific polyclonal Ab that recognizes meningitis etiologic agent, as well as the MRHAS antigen, but not the naturally occurring hMCP, the JE-MRHAS antigen would make an excellent universal vaccine. The fact it does not bind the hMCP-1 supports its safe use as it will not cause an autoimmune reaction.

Experiments were performed to determine if the antibody response was dose-dependent. A second bleed was taken, one week after the fourth injection. Serum from each of the 4 mice in each group was pooled and used to perform ELISA tests as described.

TABLE 9

| | 25 μg | 50 μg | 100 μg | Control #1 | Control #2 |
|---|---|---|---|---|---|
| 200× | 0.580 | 0.666 | 0.725 | 0.055 | 0.056 |
| 400× | 0.578 | 0.696 | 0.786 | 0.043 | 0.052 |
| 800× | 0.504 | 0.652 | 0.714 | 0.043 | 0.051 |
| 1600× | 0.494 | 0.628 | 0.718 | 0.041 | 0.046 |
| 3200× | 0.376 | 0.514 | 0.616 | | |
| 6400× | 0.143 | 0.440 | 0.520 | | |

As is apparent from the results shown in Table 9, the antibody response is dose-dependent. The ideal dose appears to be approximately 40-50 μg of antigen per immunization per mouse.

For human immunizations the vaccines are designed to contain the MRHAS from any meningitis-causing organism. For example, the antigenic sequence from the *S. pneumoniae* septapeptide is QQQPPKA (Seq ID No:25). This sequence is synthesized at the carboxy terminus of a polypeptide that contains a portion of the amino sequence of the human chemokine hMCP-1. The synthetic vaccine therefore has the amino acid sequence KEAVVFVTKLICREVCADP-KKEWVQTYIKNLDR-QQQPPKA (Seq ID No:75).

EXAMPLE 4

Protective Effect of Monoclonal Antibody Directed Against S. Pneomoniae Antigen "QQQPPKA" In Vivo An experiment was undertaken to determine whether a monoclonal antibody directed against the *S. pneumoniae* MRHAS amino acid sequence QQQPPKA (Seq ID No:25) protected baby rats from infection with *H. influenzae*. The *H. influenzae* MRHAS amino acid sequence is QVQNNKP (Seq ID No: 19) and therefore the MRHAS of *S. pneumoniae* and IL influenzae are different.

The SP8 Mab was used in this experiment. The SP8 Mab is de6cribed in U.S. patent application Ser. No. 081/262,463, entitled "Monoclonal Antibody to Cell Surface Protein of the Bacterium *Streptococcus*," which is incorporated herein by reference. This Mab is directed to the amino acid sequence QQPPKE and is produced by cell line 11E-1. The cell line 11E-1 was deposited at the American Type Culture Collection and accorded accession No. HB11262.

The SP8 Mab was employed in a standard "clearance" assay designed to measure the level of bacteremia in baby rats challenged with infection by the meningitis-causing organism *H. influenzae*. See Weller et al., J. Infec. Di. 135(1): 34-41 (1977); Rubin et al., J. Infec. Dis. 160(3): 476-482 (1989) and Karp et al., J. Ped. Surgery 24(1): 112-117 (1989). *H. influenzae* exists as six distinct encapsulated types, designated a to f, as well as unencapsulated-strains. Pittman, M., J. Exp. Med. 53:471-492 (1931). Type b is the primary cause of meningitis in young children and is designated Hib. The distinguishing antigen In the Hib capsule is polyrdbosylribitol phosphate (PRP). Rosenberg, E. and Zamenhof, S., J. Biol. Chem. 236: 2845-2849 (1961).

The experiment was conducted by making serial dilutions of SP8 antibody and administering these dilutions subcutaneously to infant rats. Ten day old Sprague-Dawley rats (COBS/CD, Charles River Breeding Laboratories) were used after they were shown to be negative for antibodies for Hib. Twenty four hours following administration of the specific antibody, Hib was inoculated intraperitoneally at a concentration of 6,000 bacteria per animal. More specifically, cultures of *H. influenzae* type b Eag, designated strain b (Hib), were grown to midlog phase in brain-heart infusion (BHI) broth supplemented with serum and nicotinamide adenine dinucleotide. Cultures were prepared for inoculation in cold phosphate buffered saline containing 0.1 W gelatin (PBS-G).

Blood samples were taken 24 hours after inoculation of the rats with Rib and plated to determine the number of organisms contained per unit volume. More specifically, blood samples were taken from the left femoral tail vein, heparinized and dilutions of 0.10 Al aliquots were plated on chocolate agar.

Positive and negative controls were included in the experiment. The positive control consisted of an antibody directed against the Hib capsular antigen and designated BPIG. The negative control consisted of a Mab directed against human choriogonadotropin (hCG), an antigen unrelated to Hib. Each antibody was evaluated at 3 serial decimal dilutions as indicated in Table 9.

TABLE 10

| Antibody | Dose, μg | Geometric mean colonies/ 0.1 μl blood @ 24 hours post | Survivors at 5 days post/ # injected |
|---|---|---|---|
| Positive control (BPIG) | 0.84 | <0.01 | 3/3 |
|  | 0.084 | 114. | 2/3 |
|  | 0.008 | 85 | 3/3 |
| Negative Control | 358 | 33 | 4/4 |
|  | 35.8 | 85 | 3/4 |
|  | 3.6 | 205 | 2/3 |
| SP8 | 2.10. | 1.67 | 4/4 |
|  | 21 | 10 | 3/3 |
|  | 2.1 | 45 | 3/3 |

These data indicate that the positive control antibody was effective at a concentration of 0.8 ug, while the SP8 Mab was effective at a concentration of 200 μg. There was significant, detectable clearance of Hib organisms by the SP8 antibody. These data demonstrate that antibody directed against the *S. pneumoniae* MRHAS amino acid sequence QQQPPKA (Seq ID No:25) has some protective effect in vivo against challenge by another meningitis-causing organism *H. influenzae* type b. Since the amino acid sequence of MRHAS from *H. influenzae* type b differs from the MRHAS in *S. pneumoniae*, the data demonstrate that an antibody directed to an MRHAS, such as SP8, can be used in vivo to protect the animal from infection from a diverse array of meningitis-causing organisms. The protective effect may block the common MRHAS-mediated entry of the meningitis-causing organisms into carrier monocytes.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

The invention claimed is:

1. A method for promoting clearance in vivo against challenge by a meningitis causing bacteria, said method comprising administering an effective amount of a composition, said composition comprising a monoclonal antibody which binds a peptide consisting of the amino acid sequence ase set forth in SEQ ID NO:25.

2. A method according to claim 1, wherein said composition is administered intravenously.

3. The method of claim 1 wherein said bacteria is *H. influenzae* type b.

* * * * *